US006639062B2

(12) United States Patent
Manoharan et al.

(10) Patent No.: US 6,639,062 B2
(45) Date of Patent: Oct. 28, 2003

(54) AMINOOXY-MODIFIED NUCLEOSIDIC COMPOUNDS AND OLIGOMERIC COMPOUNDS PREPARED THEREFROM

(75) Inventors: Muthiah Manoharan, Carlsbad; Phillip Dan Cook, Fallbrook; Thazha P. Prakash; Andrew M. Kawasaki, both of Carlsbad, all of CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 20 days.

(21) Appl. No.: 09/370,541

(22) Filed: Aug. 9, 1999

(65) Prior Publication Data

US 2003/0088079 A1 May 8, 2003

Related U.S. Application Data

(63) Continuation-in-part of application No. 09/344,260, filed on Jun. 25, 1999, and a continuation-in-part of application No. 09/130,973, filed on Aug. 7, 1998, which is a continuation-in-part of application No. 09/016,520, filed on Jan. 30, 1998.
(60) Provisional application No. 60/037,143, filed on Feb. 14, 1997.

(51) Int. Cl.$^7$ .......................... C07H 21/00; C07H 21/02; C07H 21/04
(52) U.S. Cl. .................... 536/23.1; 536/24.3; 536/24.5; 514/44
(58) Field of Search .............................. 536/23.1, 24.3, 536/24.5; 514/44

(56) References Cited

U.S. PATENT DOCUMENTS

| | | | |
|---|---|---|---|
| 3,687,808 A | | 8/1972 | Merigan et al. ............... 195/28 |
| 5,118,800 A | | 6/1992 | Smith et al. .................... 536/23 |
| 5,124,047 A | | 6/1992 | Quach et al. ................. 210/699 |
| 5,132,418 A | | 7/1992 | Caruthers et al. .............. 536/27 |
| 5,134,066 A | | 7/1992 | Rogers et al. ................. 435/91 |
| 5,210,264 A | | 5/1993 | Yau ............................ 558/167 |
| 5,223,618 A | * | 6/1993 | Cook et al. .................. 544/276 |
| 5,264,562 A | * | 11/1993 | Matteucci et al. ......... 536/23.1 |
| 5,378,825 A | * | 1/1995 | Cook et al. ............... 536/25.34 |
| 5,571,902 A | * | 11/1996 | Ravikumar et al. ........ 536/25.3 |
| 5,578,718 A | * | 11/1996 | Cook et al. ............... 536/27.21 |
| 5,596,086 A | * | 1/1997 | Matteucci et al. ......... 536/22.1 |
| 5,627,053 A | | 5/1997 | Usman et al. .............. 435/91.1 |
| 5,639,873 A | | 6/1997 | Barascut et al. ........... 536/25.3 |
| 5,646,265 A | | 7/1997 | McGee .................... 536/25.34 |
| 5,658,873 A | | 8/1997 | Bertsch-Frank et al. .... 510/375 |
| 5,670,633 A | | 9/1997 | Cook et al. ................. 536/23.1 |
| 5,681,941 A | | 10/1997 | Cook et al. ................. 536/23.1 |
| 5,700,920 A | | 12/1997 | Altmann et al. |
| 5,792,608 A | * | 8/1998 | Swaminathan et al. ........ 435/6 |
| 5,817,781 A | * | 10/1998 | Swaminathan et al. .... 536/22.1 |

FOREIGN PATENT DOCUMENTS

| | | | |
|---|---|---|---|
| WO | WO 92/03464 | | 3/1992 |
| WO | 9639531 | * | 12/1996 |
| WO | 9835978 | * | 8/1998 |

OTHER PUBLICATIONS

Agrawal et al. (eds.), "Methods of Molecular Biology", in *Protocols for Oligonucleotide Conjugates*, Humana Press, New Jersey, 1994, vol. 26, 1–72.

Albert, P.R. et al., "Antisense knockouts: molecular scalpels for the dissection of signal transduction", *Trends Pharmacol. Sci.*, 1994, 15, 250–254 (Jul., 1994).

Albretson, C. et al., "Applications of Magnetic Beads with Covalently Attached Oligonucleotides in Hybridization: Isolation and Detection of Specific Measles Virus mRNA from a Crude Cell Lysate," *Anal. Biochem.*, 1990, 189, 40–50.

Azhayev, A. et al., "Analogues of Oligonucleotides Containing 3'–Deoxy–Psicothymidine," *Tetra. Lett.*, 1993, 34(40), 6435–6438.

Beaucage, S.L. et al., "Advances in the Synthesis of Oligonucleotides by the Phosphoramidite Approach", *Tetrahedron*, 1992, 48, 2223–2311.

Bischoff, R. "Introduction of 5'–Terminal Functional Groups into Synthetic Oligonucleotides for selective Immobilization", *Analyt. Biochem.*, 1987, 164, 336–344.

Chee, M. et al., "Accessing Genetic Information with High–Density DNA Arrays," *Science*, 1996, 274, 610–614 (Oct. 25, 1996).

Cohen, G. et al., "Covalent attachment of DNA oligonucleotides to glass," *Nucl. Acids Res.*, 1997, 25(4), 911.

Cook, P.D., "Medicinal Chemistry of Antisense Oligonucleotides—future opportunities", *Anti–Cancer Drug Design*, 1991, 6, 585–607.

Cronin, M.T. et al., "Cystic Fibrosis Mutation Detection by Hybridization to Light–Generated DNA Probe Arrays," *Human Mat.*, 1996, 7, 244–255.

Damha, M.J. et al., "An improved procedure for derivatization of controlled–pore glass beads for solid–phase oligonucleotides synthesis," *Nucl. Acids Res.*, 1990, 18(13), 3813–3821.

Delgado, C. et al., "The Uses and Properties of PEG–Linked Proteins", *Crit. Rev. in Therapeutic Drug Carrier Sys.*, 1992, 9, 249–304.

Ducray, P. et al., "Enantioconvergent Formal Synthesis of Brefeldin A via Sakai–Catalyzed Cyclization," *J. Org. Chem.*, 1999, 64, 3800–3801 (Issue No. 11).

(List continued on next page.)

Primary Examiner—Johann Richter
Assistant Examiner—L. Eric Crane
(74) Attorney, Agent, or Firm—Woodcock Washburn LLP

(57) ABSTRACT

Nucleosidic monomers and oligomeric compounds prepared therefrom are provided which have increased nuclease resistance, substituent groups (such as 2'-aminooxy groups) for increasing binding affinity to complementary strand, and regions of 2'-deoxy-erythro-pentofuranosyl nucleotides that activate RNase H. Such oligomeric compounds are useful for diagnostics and other research purposes, for modulating the expression of a protein in organisms, and for the diagnosis, detection and treatment of other conditions susceptible to oligonucleotide therapeutics.

83 Claims, 35 Drawing Sheets

OTHER PUBLICATIONS

Englisch, U. et al., "Chemically Modified Oligonucleotides as Probes and Inhibitors", *Angew. Chem. Int. Ed. Eng.,* 1991, 30, 613–629 (Jun., 1991).

Erout, M–N. et al., "Preparation of Conjugates between Oligonucleotides and N–Vinylpyrrolidone/N–Acryloxysuccinimide Copolymers and Applications in Nucleic Acid Assays to Improve Sensitivity," *Bioconjugate Chem.,* 1996, 7, 568–575 (Is. No. ).

Fahy, E. et al., "Design and synthesis of polyacrylamide-based oligonucleotide supports for use in nucleic acid diagnostics", *Nuc. Acids. Res.,* 1993, 21, 1819–1826 (No. 8).

Ghosh, S.S. et al., "Covalent attachment of oligonucleotides to solid supports", *Nucl. Acids Res.,* 1987, 15, 5353–5373 (Issue No. 13).

Gibson, U.E.M. et al., "A Novel Method for Real Time Quantitative RT–PCR," *Genome Res.,* 1996, 6, 995–1001.

Glasser, "ISIS Pharmaceuticals Demonstrates Efficacy in Crohn's Disease with its Antisense Drug," *Genetic Eng. News,* 1997, 17, 1 and 34 (Mar. 1, 1997).

Guo, Z. et al., "Direct fluorescence analysis of genetic polymorphisms by hybridization with oligonucleotide arrays on glass supports", *Nucl. Acids Res.,* 1994, 22, 5456–5465 (Issue No. 24).

Hacia, J.G. et al., "Two color hybridization analysis using high density oligonucleotide arrays and energy transfer dyes," *Nucl. Acids Res.,* 1998, 26(16), 3865–3866.

Hakala, H. et al., "Detection of Oligonucleotide Hybridization on a Single Microparticle by Time–Resolved Fluorometry: Quantitation and Optimization of a Sandwich Type Assay," *Bioconjugate Chem.,* 1998, 9, 316–321 (Issue No. 3).

Hakala, H. et al., "Time–Resolved Fluorescence Detection of Oligonucleotide Hybridization on a Single Microparticle: Covalent Immobilization of Oligonucleotides and Quantitation of a Model System," *Bioconjugate Chem.,* 1997, 8, 232–237 (Issue No. 2).

Hakala, H. et al., "Detection of Oligonucleotide Hybridization on a Single Microparticle by Time–Resolved Fluorometry: Hybridization Assays on Polymer Particles Obtained by Direct Solid Phase Assembly of the Oligonucleotide Probes," *Bioconjugate Chem.,* 1997, 8, 378–384 (Issue No. 3).

Hamm, M. L. et al., "Incorporation of 2'–Deoxy–2'–mercaptocytidine into Oligonucleotides via Phosphoramidite Chemistry," *J. Org. Chem.,* 1997, 62, 3415–3420 (Issue No. 10).

Hovinen, J. et al., "Novel Solid Supports for the Preparation of 3'–Derivatized Oligonucleotides: Introduction of 3'–Alkylphosphate Tether Groups Bearing Amino, Carboxy, Carboxamido, and Mercapto Functionalities," *Tetrahedron,* 1994, 50, 7203–7218(#24).

Kawasaki, A.M. et al., "Synthesis, Hybridization, and Nuclease Resistance Properties of 2'–O–Aminooxyethyl (2'–O–AOE) Modified Oligonucleotides," *Tetra. Lett.,* 1999, 40, 661–664.

Kozal, M.J. et al., "Extensive polymorphisms observed in HIV–1 clade B protease gene using highly–density oligonucleotide arrays," *Nat. Med.,* 1996, 2(7), 753–759 (Jul. 1996).

Kremsky, J.N. et al., "Immobilization of DNA via oligonucleotides containing an aldehyde or carboxylic acid group at the 5' terminus," *Nucl. Acids Res.,* 1987, 15(7), 2891–2909.

Kroschwitz, J.I., "Polynucleotides", Concise Encyclopedia of Polymer Science and Engineering, 1990, John Wiley & Sons, New York, 858–859.

Kung, P–P. et al., "One–Flask Syntheses of 6–Thioguanosine and 2'–Deoxy–6–Thioguanosine," *Tetra. Lett.,* 1991, 32(32), 3919–3922.

Kwoh, D. Y. et al., "Transcription–based amplification system ad detection of amplified human immunodeficiency virus type 1 with a bead–based sandwich hybridization format," *Proc. Natl. Acad. Sci. USA,* 1989, 86, 1173–1177 (Feb., 1989).

Lamture, J.B. et al., "Direct detection of nucleic acid hybridization on the surface of a charge coupled device," *Nucl. Acids Res.,* 1994, 22(11), 2121–2125.

Lemieux, G.A. et al., "Exploiting Differences in Sialoside Expression for Selective Targeting of MRI Contrast Reagents," *J. Am. Chem. Soc.,* 1999, 121, 4278–4279 (#17).

Lövgren, T. et al., "Sensitive bioaffinity assays with individual microparticles and time–resolved fluorometry," *Clin. Chem.,* 1997, 43(10), 1937–1943.

Lund, V. et al., "Assessment of methods for covalent binding of nucleic acids to magnetic beads, Dynabeads™, and the characteristics of the bound nucleic acids in hybridization reactions", *Nucl. Acids Res.,* 1988, 16, 10861–10880 (Issue No. 22).

Maskos, U. et al., "Oligonucleotide hybridisations on glass supports: a novel linker for oligonucleotide synthesis and hybridisation properties of oligonucleotides synthesised in situ", *Nucl. Acids Res.,* 1992, 20, 1679–1684.

Mitsunobu,O., "The Use of Diethyl Azodicarboxylate and Triphenylphosphine in Synthesis and Transformation of Natural Products," *Synthesis,* 1981, 1–28 (Jan., 1981).

Mukkala, V–M. et al., "85. Development of Luminescent Europium(III) and Terbium(III) Chelates of 2,2':6', 2"–Terpyridine Derivatives for Protein Labelling," *Helv. Chim. Acta.,* 1993, 76, 1361–1378.

O'Donnell, M.J. et al., "High–Density, Covalent Attachment of DNA to Silicon Waferes for Analysis by MALDI–TOF Mass Spectrometry," *Anal. Chem.,* 1997, 69, 2438–2443 (Jul. 1, 1997).

Ouchi, T. et al., "Synthesis and Antitumor Activity of Poly(Ethylene Glycol)s Linked to 5'–Fluorouracil via a Urethane or Urea Bond", *Drug. Des. & Disc.,* 1992, 9, 93–105.

Pirrung, M.C. et al., "Comparison of Methods for Photochemical Phosphoramidite–Based DNA Synthesis," *J. Org. Chem.,* 1995, 60, 6270–6276 (Issue No. 20).

Polushin, N. N. et al., "Synthesis of Oligonucleotides Containing 2'–Azido–and 2'–Amino–2'–deoxyuridine Using Phosphotriester Chemistry," *Tetrahedron Letts.,* 1996, 37(19), 3227–3230.

Ravasio, N. et al., "Selective Hydrogenations Promoted by Copper Catalysts. 1. Chemoselectivity, Regioselectivity, and Stereoselectivity in the Hydrogenation of 3–Substituted Steroids", *J. Org. Chem.,* 1991, 56, 4329–4333 (Issue No. 13).

Saiki, R.K. et al., "Genetic analysis of amplified DNA with immobilized sequence–specific oligonucleotide probes," *Proc. Natl. Acad. Sci. USA,* 1989, 86, 6230–6234 (Aug. 1989).

Southern, E.M. et al., "Discovering antisense reagents by hybridization of RNA to oligonucleotide arrays," in *Oligonucleotides as Therapeutic Agents,* Ciba Foundation Symposium, 1997, 209, 38–46.

Tang, K. et al., "Matrix–assisted lasere desorption/ionization mass spectrometry of immobilized duplex DNA probes," *Nucl. Acids Res.*, 1995, 23(16), 3126–3131.

Thomson, J. B. et al., "Synthesis and Properties of Diuridine Phosphate Analogues Containing Thio and Amino Modifications," *J. Org. Chem.*, 1996, 61, 6273–6281 (#18).

Timofeev, E.N. et al., "Regioselective immobilization of short oligonucleotides to acrylic copolymer gels," *Nucl. Acids Res.*, 1996, 24(16), 3142–3148 (Iss. No. 16).

Van Ness, J. et al.,"A versatile solid support system for oligodeoxynucleotide probe–based hybridization assays", *Nucl. Acids Res.*, 1991, 19, 3345–3350 (Issue No. 12).

Williams,M.A. et al., "Synthesis of Enantiomerically Pure Diethylenetriaminepentaacetic Acid Analogues. L–Phenylalanine as the Educt for Substitution at the Central Acetic Acid," *J. Org. Chem.*, 1993, 58, 1151–1158 (Issue No. 5).

Yarden, R.I. et al., "BRCA1 interacts with components of the histone deacetylase complex," *Proc. Natl. Acad. Sci. USA*, 1999, 96, 4938–4988 (Apr., 1999).

Yershov, G. et al., "DNA analysis and diagnostics on oligonucleotide microchips," *Proc. Natl. Acad. Sci USA*, 1996, 93, 4913–4918 (May, 1996).

Zhang et al., "Single–base mutational analysis of cancer and genetic diseases using membrane bound modified oligonucleotides," *Nucl. Acids Res.*, 1991, 19(14), 3929–3933.

Alul, R.H. et al., "Oxalyl–CPG: a labile support for synthesis of sensitive oligonucleotide derivatives",*Nucl. Acid Res.*, 1991, 19, 1527–1532 (Issue No. 7).

Crooke, S.T. et al., "Pharmacokinetic Properties of Several Novel Oligonucleotide Analogs in mice", *J. Pharmacol. Exp. Therapeutics*, 1996, 277, 923–937 (Iss. No. 2).

Kabanov, A.V., "A new class of antivirals: antisense olgonucleotides combined with a hydrophobic substituent effectively inhibit influenza virus reproduction and synthesis of virus–specific proteins in MDCK cells", *FEBS Letts.*, 1990, 259, 327–330 (Jan., 1990).

Letsinger, R.L. et al., "Cholesteryl–conjugated oligonucleotides: Synthesis, properties and activity as inhibitors of replication of human immunodeficiency virus in cell culture", *Proc. Natl. Acad. Sci.*,1989, 86, 6553–6556 (Sep., 1989).

Manoharan M. et al., "Cholic Acid–Oligonucleotide Conjugates for Antisense Applications", *Bioorganic Med. Chem. Letts.*, 1994, 4, 1053–1060 (Issue No. 8).

Manoharan, M. et al., "Chemical Modifications to Improve Uptake and Bioavailability of Antisense Oligonucleotides", *Annals NY Acad. Sciences*, 1992, 660, 306–309.

Manoharan, M. et al., "Introduction of a Lipophilic Thioether Tether in the Minor Groove of Nucleic Acids for Antisense Applications", *Bioorg. Med. Chem. Letts.*, 1993, 3, 2765–2770 (Issue No. 12).

Manoharan, M. et al., "Lipidic Nucleic Acids", *Tetrahedron Letts.*, 1995, 36, 3651–3654 No.

Manoharan M. et al., "Oligonucleotide Conjugates: Alteration of the Pharmacokinetic Properties of Antisense Agents", *Nucleosides and Nucleotides*, 1995, 14, 969–973 (#3–5).

Mishra, R.K. et al., "Improved leishmanicidal effect of phosphorotioate antisense oligonucleotides by LDL–medicated delivery", *Biochim. Et Biophyhsica*, 1995, 1264, 229–237.

Oberhauser, B. et al., "Effective incorporation of 2'–O–methyl–oligonucleotides into liposomes and enhanced cell association through modification with thiocholesterol", *Nucl. Acids Res.*, 1992, 20, 533–538 (Issue No. 3).

Sanghvi, Y.S., "Heterocyclic Base Modifications in Nucleic acids and their Applications in Antisense Oligonucleotides", *Antisense Research and Applications*, 1993, Chapter 15, CRC Press, Boca Raton, 2733–288.

Secrist, J.A. et al., "Synthesis and Biological Activity of 4'–Thionucleosides", 10th International Roundtable: Nucleosides, Nucleotides and their Biological Applications, Sep. 16–20, 1992, Abstract 21, Park City, Utah, 40.

Shea, R.G. et al., "Synthesis hybridization properties and antiviral activity of lipid–oligodeoxynucletide conjugates", *Nucl. Acids Res.*, 1990, 18, 3777–3783.

Svinarchuk, F.P. et al., "Inhibition of HIV proliferation in MT–4 cells by antisense oligonucleotide conjugated to lipophilic groups", *Biochime*, 1993, 79, 49–54.

Wright, P. et al., "Large Scale Synthesis of Oligonucleotides via phosphoramidite Nucleosides and a High–loaded Polystyrene Support", *Tetrahedron Letts.*, 1993, 34, 3373–3376.

* cited by examiner

Nuclease Resistance of Oligonucleotides Capped at the 3'-end with 2'-modified Nucleotides Resistance of 2'-modified Oligonucleotides to
Phosphodiesterase I. Half Life of Intact Oligonucleotide.

5' TTT TTT TTT TTT TTT* T*T*T* T 3'

Where T* is 2'-modified nucleotide (DMAOE or MOE)

Amino-Oxy Precursursors:

X = NH, O, S, N-alkyl

AMINOOXY-MODIFIED NUCLEOSIDIC COMPOUNDS AND OLIGOMERIC COMPOUNDS PREPARED THEREFROM

RELATED APPLICATION DATA

This patent application is a continuation-in-part of application Ser. No. 09/130,973 filed on Aug. 7, 1998, and application Ser. No. 09/344,260 filed on Jun. 25, 1999, which is a continuation-in-part of application Ser. No. 09/016,520, filed on Jan. 30, 1998, which claims priority benefit of U.S. Provisional Application Ser. No. 60/037,143, filed on Feb. 14, 1997. The contents of each of the foregoing applications are incorporated herein by reference in their entirety.

FIELD OF THE INVENTION

This invention is directed to aminooxy-modified nucleosides and oligonucleotides, to oligonucleotides that elicit RNase H for cleavage in a complementary nucleic acid strand, and to oligonucleotides wherein at least some of the nucleotides are functionalized to be nuclease resistant, at least some of the nucleotides of the oligonucleotide including a substituent that potentiates hybridization of the oligonucleotide to a complementary strand of nucleic acid, and at least some of the nucleotides of the oligonucleotide include 2'-deoxy-erythro-pentofuranosyl sugar moiety. The inclusion of one or more aminooxy moieties in such oligonucleotide provides, inter alia, for improved binding of the oligonucleotides to a complementary strand. The oligonucleotides and macromolecules are useful for therapeutics, diagnostics and as research reagents.

BACKGROUND OF THE INVENTION

Oligonucleotides are known to hybridize to single-stranded RNA or single-stranded DNA. Hybridization is the sequence specific base pair hydrogen bonding of bases of the oligonucleotides to bases of target RNA or DNA. Such base pairs are said to be complementary to one another.

In determining the extent of hybridization of an oligonucleotide to a complementary nucleic acid, the relative ability of an oligonucleotide to bind to the complementary nucleic acid may be compared by determining the melting temperature of a particular hybridization complex. The melting temperature ($T_m$), a characteristic physical property of double helices, denotes the temperature in degrees centigrade, at which 50% helical (hybridized) versus coil (unhybridized) forms are present. $T_m$ is measured by using the UV spectrum to determine the formation and breakdown (melting) of the hybridization complex. Base stacking which occurs during hybridization, is accompanied by a reduction in UV absorption (hypochromicity). Consequently, a reduction in UV absorption indicates a higher $T_m$. The higher the $T_m$, the greater the strength of the bonds between the strands.

Oligonucleotides can be used to effect enzymatic cleavage of a target RNA by using the intracellular enzyme, RNase H. The mechanism of such RNase H cleavage requires that a 2'-deoxyribofuranosyl oligonucleotide hybridize to a target RNA. The resulting DNA-RNA duplex activates the RNase H enzyme and the activated enzyme cleaves the RNA strand. Cleavage of the RNA strand destroys the normal function of the RNA. Phosphorothioate oligonucleotides operate via this type of mechanism. However, for a DNA oligonucleotide to be useful for cellular activation of RNase H, the oligonucleotide must be reasonably stable to nucleases in order to survive in a cell for a time period sufficient for RNase H activation. For non-cellular uses, such as use of oligonucleotides as research reagents, such nuclease stability may not be necessary.

Several publications of Walder et al. describe the interaction of RNase H and oligonucleotides. Of particular interest are: (1) Dagle et al., *Nucleic Acids Research* 1990, 18, 4751; (2) Dagle et al., *Antisense Research And Development* 1991, 1, 11; (3) Eder et al.,*J. Biol. Chem.* 1991, 266, 6472; and (4) Dagle et al., *Nucleic Acids Research* 1991, 19, 1805. According to these publications, DNA oligonucleotides having both unmodified phosphodiester internucleoside linkages and modified phosphorothioate internucleoside linkages are substrates for cellular RNase H. Since they are substrates, they activate the cleavage of target RNA by RNase H. However, the authors further note that in Xenopus embryos, both phosphodiester linkages and phosphorothioate linkages are also subject to exonuclease degradation. Such nuclease degradation is detrimental since it rapidly depletes the oligonucleotide available for RNase H activation.

As described in references (1), (2) and (4), to stabilize oligonucleotides against nuclease degradation while still providing for RNase H activation, 2'-deoxy oligonucleotides having a short section of phosphodiester linked nucleotides positioned between sections of phosphoramidate, alkyl phosphonate or phosphotriester linkages were constructed. Although the phosphoramidate-containing oligonucleotides were stabilized against exonucleases, in reference (4) the authors noted that each phosphoramidate linkage resulted in a loss of 1.6° C. in the measured $T_m$ value of the phosphoramidate containing oligonucleotides. Such a decrease in the $T_m$ value is indicative of an decrease in hybridization between the oligonucleotide and its target strand.

Other authors have commented on the effect such a loss of hybridization between an oligonucleotide and its target strand can have. Saison-Behmoaras et al., *EMBO Journal* 1991, 10, 1111, observed that even though an oligonucleotide could be a substrate for RNase H, cleavage efficiency by RNase H was low because of weak hybridization to the mRNA. The authors also noted that the inclusion of an acridine substitution at the 3' end of the oligonucleotide protected the oligonucleotide from exonucleases.

U.S. Pat. No. 5,013,830, issued May 7, 1991, discloses mixed oligomers comprising an RNA oligomer, or a derivative thereof, conjugated to a DNA oligomer via a phosphodiester linkage. The RNA oligomers also bear 2'-O-alkyl substituents. However, being phosphodiesters, the oligomers are susceptible to nuclease cleavage.

European Patent application 339,842, filed Apr. 13, 1989, discloses 2'-O-substituted phosphorothioate oligonucleotides, including 2'-O-methylribooligonucleotide phosphorothioate derivatives. The above-mentioned application also discloses 2'-O-methyl phosphodiester oligonucleotides which lack nuclease resistance.

U.S. Pat. No. 5,149,797, issued Sep. 22, 1992, discloses mixed phosphate backbone oligonucleotides which include an internal portion of deoxynucleotides linked by phosphodiester linkages, and flanked on each side by a portion of modified DNA or RNA sequences. The flanking sequences include methyl phosphonate, phosphoromorpholidate, phosphoropiperazidate or phosphoramidate linkages.

U.S. Pat. No. 5,256,775, issued Oct. 26, 1993, describe mixed oligonucleotides that incorporate phosphoramidate linkages and phosphorothioate or phosphorodithioate linkages.

Although it has been recognized that cleavage of a target RNA strand using an oligonucleotide and RNase H would be useful, nuclease resistance of the oligonucleotide and fidelity of hybridization are of great importance in the development of oligonucleotide therapeutics. Accordingly, there remains a long-felt need for methods and materials that could activate RNase H while concurrently maintaining or improving hybridization properties and providing nuclease resistance. Such oligonucleotides are also desired as research reagents and diagnostic agents.

BRIEF DESCRIPTION OF THE INVENTION

In accordance with one embodiment of this invention there are provided compounds of the structure:

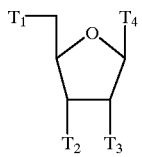

wherein:
$T_4$ is Bx or Bx—L where Bx is a heterocyclic base moiety;
one of $T_1$, $T_2$ and $T_3$ is L, hydrogen, hydroxyl, a protected hydroxyl or a sugar substituent group;
another one of $T_1$, $T_2$ and $T_3$ is L, hydroxyl, a protected hydroxyl, a connection to a solid support or an activated phosphorus group;
the remaining one of $T_1$, $T_2$ and $T_3$ is L, hydrogen, hydroxyl or a sugar substituent group provided that at least one of $T_1$, $T_2$, $T_3$ and $T_4$ is L or Bx—L;
said group L having one of the formulas;

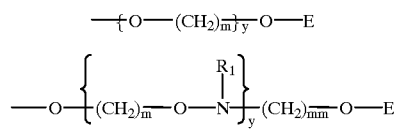

wherein:
each m and mm is, independently, from 1 to 10;
y is from 1 to 10;
E is $N(R_1)(R_2)$ or $N=C(R_1)(R_2)$;
each $R_1$ and $R_2$ is, independently, H, a nitrogen protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein said substitution is $OR_3$, $SR_3$, $NH_3^+$, $N(R_3)(R_4)$, guanidino or acyl where said acyl is an acid, amide or an ester;
or $R_1$ and $R_2$, together, are a nitrogen protecting group or are joined in a ring structure that optionally includes an additional heteroatom selected from N and O; and
each $R_3$ and $R_4$ is, independently, H, $C_1$–$C_{10}$ alkyl, a nitrogen protecting group, or $R_3$ and $R_4$, together, are a nitrogen protecting group;
or $R_3$ and $R_4$ are joined in a ring structure that optionally includes an additional heteroatom selected from N and O.

In some preferred embodiments, one of $T_1$, $T_2$ or $T_3$ is L. In further preferred embodiments $T_3$ is L.

In further preferred embodiments L is —O—$(CH_2)_2$—O—$N(R_1)(R_2)$. In another preferred embodiment $R_1$ is H or $C_1$–$C_{10}$ alkyl or $C_1$–$C_{10}$ substituted alkyl and $R_2$ is $C_1$–$C_{10}$ substituted alkyl, preferably wherein $R_1$ is $C_1$–$C_{10}$ alkyl and/or $R_2$ is $NH_3^+$ or $N(R_3)(R_4)$ $C_1$–$C_{10}$ substituted alkyl. In another preferred embodiment $R_1$ and $R_2$ are both $C_1$–$C_{10}$ substituted alkyl, with preferred substituents being independently, $NH_3^+$ or $N(R_3)(R_4)$.

In some preferred embodiments Bx is adenine, guanine, hypoxanthine, uracil, thymine, cytosine, 2-aminoadenine or 5-methylcytosine.

In some preferred embodiments $R_1$ and $R_2$ are joined in a ring structure that can include at least one heteroatom selected from N and O, with preferred ring structures being imidazole, piperidine, morpholine or a substituted piperazine wherein the substituent is prefereably $C_1$–$C_{12}$ alkyl.

In some preferred embodiments $T_1$ is a protected hydroxyl. In other preferred embodiments $T_2$ is an activated phosphorus group or a connection to a solid support. In some preferred embodiments, the solid support is microparticles. In further preferred embodiments the solid support material is CPG.

In some preferred embodiments L is bound to an exocyclic amino functionality of Bx. In other preferred embodiments, L is bound to a cyclic carbon atom of Bx.

In further preferred embodiments $T_4$ is Bx—L. In still further preferred embodiments, Bx is adenine, 2-aminoadenine or guanine. In further preferred embodiments Bx is a pyrimidine heterocyclic base and L is covalently bound to C5 of Bx. In still further preferred embodiments Bx is a pyrimidine heterocyclic base and L is covalently bound to C4 of Bx. In yet further preferred embodiments Bx is a purine heterocyclic base and L is covalently bound to N2 of Bx. In still further preferred embodiments Bx is a purine heterocyclic base and L is covalently bound to N6 of Bx.

In accordance with some preferred embodiments, there are provided oligomeric compounds which incorporate at least one nucleosidic compound that is functionalized to increase nuclease resistance of the oligomeric compounds. In a further embodiment oligomeric compounds are functionalized with a substituent group to increase their binding affinity to target RNAs.

The oligomeric compounds preferably comprise a plurality of nucleoside units of the structure:

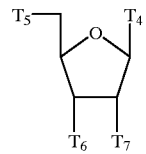

wherein:
$T_4$ of each nucleoside unit is, independently, Bx or Bx—L where Bx is a heterocyclic base moiety;
one of $T_5$, $T_6$ and $T_7$ of each nucleoside unit is, independently, L, hydroxyl, a protected hydroxyl, a sugar substituent group, an activated phosphorus group, a connection to a solid support, a nucleoside, a nucleotide, an oligonucleoside or an oligonucleotide;
another of $T_5$, $T_6$ and $T_7$ of each nucleoside unit is, independently, a nucleoside, a nucleotide, an oligonucleoside or an oligonucleotide;
the remaining one of $T_5$, $T_6$ and $T_7$ of each nucleoside unit is, independently, is L, hydrogen, hydroxyl, a protected hydroxyl, or a sugar substituent group;
provided that on at least one of said nucleoside units $T_4$ is Bx—L or at least one of $T_5$, $T_6$ and $T_7$ is L;
said group L having one of the formulas;

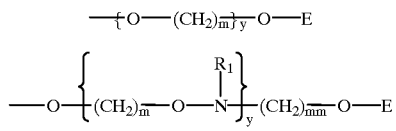

wherein:
each m and mm is, independently, from 1 to 10;
y is from 1 to 10;
E is $N(R_1)(R_2)$ or $N=C(R_1)(R_2)$
each $R_1$ and $R_2$ is, independently, H, a nitrogen protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein said substitution is $OR_3$, $SR_3$, $NH_3^+$, $N(R_3)(R_4)$, guanidino or acyl where said acyl is acid, amide or ester,
or $R_1$ and $R_2$, together, are a nitrogen protecting group or are joined in a ring structure that optionally includes an additional heteroatom selected from N and O; and
each $R_3$ and $R_4$ is, independently, H, $C_1$–$C_{10}$ alkyl, a nitrogen protecting group, or $R_3$ and $R_4$, together, are a nitrogen protecting group or wherein $R_3$ and $R_4$ are joined in a ring structure that optionally includes an additional heteroatom selected from N and O.

In some preferred embodiments of the oligomeric compounds of the invention, at least one of $T_1$, $T_2$ or $T_3$ is L. In further preferred embodiment, at least one $T_3$ is L.

In further preferred embodiments of the oligomeric compounds of the invention, at least one L is —O—$(CH_2)_2$—O—$N(R_1)(R_2)$. In further preferred embodiments of the oligomeric compounds of the invention, $R_1$ is H or $C_1$–$C_{10}$ alkyl or $C_1$–$C_{10}$ substituted alkyl and $R_2$ is $C_1$–$C_{10}$ substituted alkyl, preferably wherein $R_1$ is $C_1$–$C_{10}$ alkyl and/or $R_2$ is $NH_3^+$ or $N(R_3)(R_4)$ $C_1$–$C_{10}$ substituted alkyl. In still further preferred embodiments of the oligomeric compounds of the invention, $R_1$ and $R_2$ are both $C_1$–$C_{10}$ substituted alkyl, with preferred substituents being independently, $NH_3^+$ or $N(R_3)(R_4)$ In some preferred embodiments of the oligomeric compounds of the invention, Bx is adenine, guanine, hypoxanthine, uracil, thymine, cytosine, 2-aminoadenine or 5-methylcytosine.

In some preferred embodiments of the oligomeric compounds of the invention, $R_1$ and $R_2$ are joined in a ring structure that can include at least one heteroatom selected from N and O, with preferred ring structures being imidazole, piperidine, morpholine or a substituted piperazine wherein the substituent is preferably $C_1$–$C_{12}$ alkyl.

In some preferred embodiments of the oligomeric compounds of the invention, $T_1$ is a protected hydroxyl. In other preferred embodiments of the oligomeric compounds of the invention, $T_2$ is an activated phosphorus group or a connection to a solid support. In some preferred embodiments of the oligomeric compounds of the invention, the solid support is microparticles. In further preferred embodiments the solid support material is CPG.

In some preferred embodiments of the oligomeric compounds of the invention, L is bound to an exocyclic amino functionality of Bx. In other preferred embodiments of the oligomeric compounds of the invention, L is bound to a cyclic carbon atom of Bx.

In further preferred embodiments of the oligomeric compounds of the invention, $T_4$ is Bx—L. In still further preferred embodiments, Bx is adenine, 2-aminoadenine or guanine. In further preferred embodiments of the oligomeric compounds of the invention, Bx is a pyrimidine heterocyclic base and L is covalently bound to C5 of Bx. In still further preferred embodiments of the oligomeric compounds of the invention, Bx is a pyrimidine heterocyclic base and L is covalently bound to C4 of Bx. In yet further preferred embodiments of the oligomeric compounds of the invention, Bx is a purine heterocyclic base and L is covalently bound to N2 of Bx. In still further preferred embodiments of the oligomeric compounds of the invention, Bx is a purine heterocyclic base and L is covalently bound to N6 of Bx.

In some preferred embodiments of the oligomeric compounds of the invention, the oligomeric compounds are from 5 to 50 nucleoside units in length. In further preferred embodiments of the oligomeric compounds of the invention, the oligomeric compounds are from 8 to 30 nucleoside units in length, with 15 to 25 nucleoside units in length being more pporeferred.

In some preferred embodiments, chimeric oligomeric compounds are provided that are specifically hybridizable with DNA or RNA comprising a sequence of linked nucleoside units. Preferably, the sequence is divided into a first region having linked nucleoside units and a second region being composed of linked nucleoside units having 2'-deoxy sugar moieties. The linked nucleoside units of at least one of the first or second regions are connected by phosphorothioate linkages and at least one of the linked nucleoside units of the first region bears a group L that is covalently attached to the heterocyclic base or the 2', 3' or 5' position of the sugar moiety wherein the group L has one of the formulas:

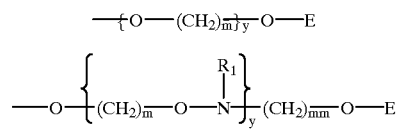

where
each m and mm is, independently, from 1 to 10;
y is from 1 to 10;
E is $N(R_1)(R_2)$ or $N=C(R_1)(R_2)$;
each $R_1$ and $R_2$ is, independently, H, a nitrogen protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein the substitution is $OR_3$, $SR_3$, $NH_3^+$, $N(R_3)(R_4)$, guanidino or acyl where the acyl is an acid, amide or an ester;
or $R_1$ and $R_2$, together, are a nitrogen protecting group or are joined in a ring structure that optionally includes an additional heteroatom selected from N and O; and
each $R_3$ and $R_4$ is, independently, H, $C_1$–$C_{10}$ alkyl, a nitrogen protecting group, or $R_3$ and $R_4$, together, are a nitrogen protecting group; and
or $R_3$ and $R_4$ are joined in a ring structure that optionally includes an additional heteroatom selected from N and O.

In some preferred embodiments, the nucleoside units of the first and second regions are connected by phosphorothioate internucleoside linkages. In further preferred embodiments, the nucleoside units of the first region are connected by phosphodiester internucleoside linkages and the nucleoside units of the second region are connected by phosphorothioate internucleoside linkages. In still further preferred embodiments, the nucleoside units of the first region are connected by phosphorothioate internucleoside linkages and the nucleoside units of the second region are connected by phosphodiester internucleoside linkages.

In some preferred embodiments, the second region has at least three nucleoside units. In further preferred embodiments, the second region has at least five nucleoside units.

In some preferred embodiments, the chimeric oligomeric compound has a third region having 2'-O-alkyl substituted nucleoside units, wherein the second region is positioned between the first and third regions. In further preferred embodiments, the nucleoside units of the first, second and third regions are connected by phosphorothioate linkages. In further preferred embodiments, the nucleoside units of the first and third regions are connected by phosphodiester linkages and the nucleoside units of the second region are connected by phosphorothioate linkages. In another preferred embodiment, the nucleoside units of the first and third regions are connected by phosphorothioate linkages and the nucleoside units of the second region are connected by phosphodiester linkages.

In some preferred embodiments, the second region has at least three nucleoside units. In further preferred embodiments, the second region has at least five nucleoside units.

In some preferred embodiments, at least one of the 2'-O-alkyl substituted nucleoside units of the third region bears an L group.

The nucleotides forming oligonucleotides of the present invention can be connected via phosphorus linkages. Preferred phosphorous linkages include phosphodiester, phosphorothioate and phosphorodithioate linkages, with phosphodiester and phosphorothioate linkages being particularly preferred.

BRIEF DESCRIPTION OF THE DRAWINGS

The numerous objects and advantages of the present invention may be better understood by those skilled in the art by reference to the accompanying figures, in which.

DETAILED DESCRIPTION OF PREFERRED EMBODIMENTS

Figure 1:
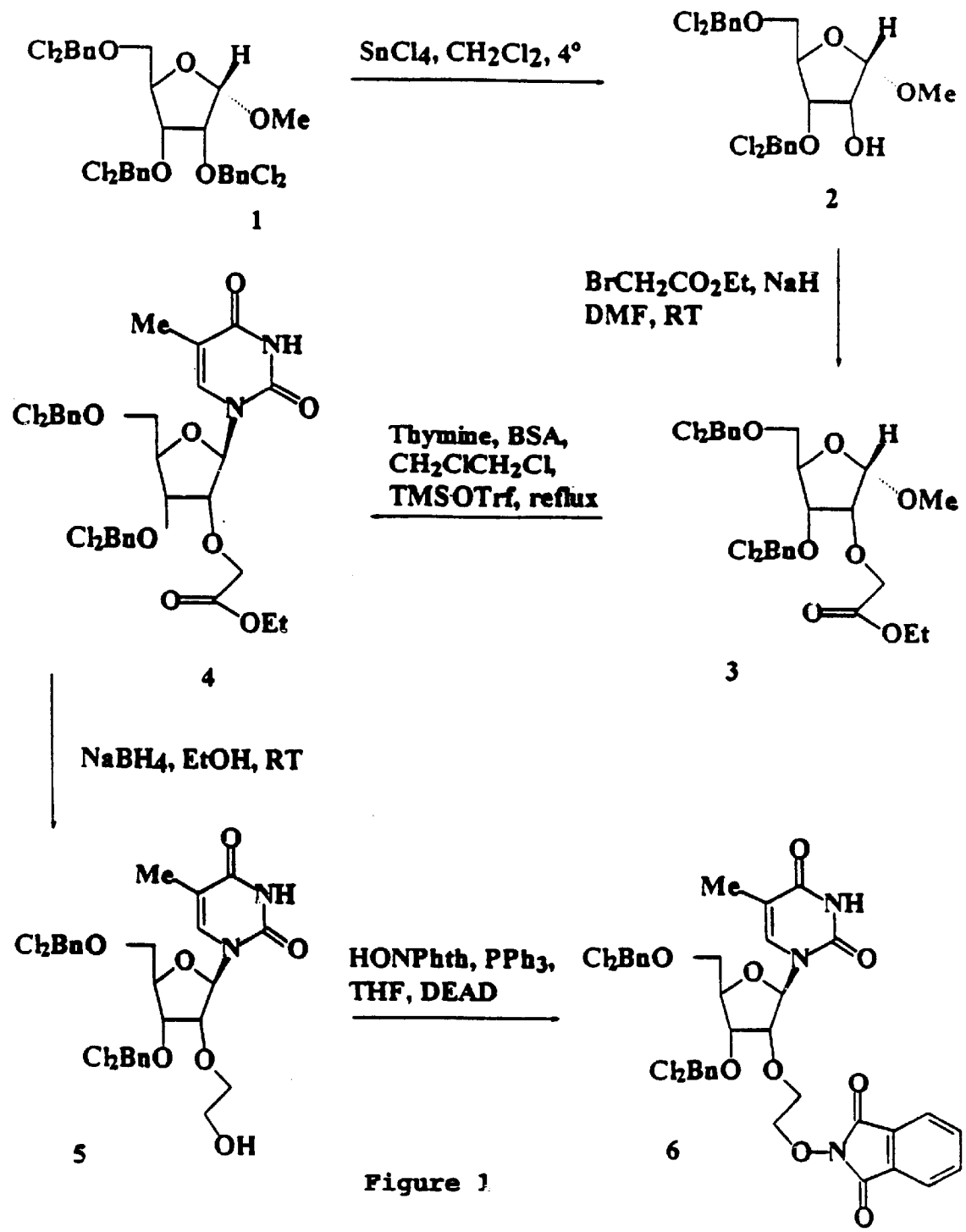
FIG. 1 shows a synthesis of certain intermediates of the invention.

The present invention presents modified nucleosidic monomers and oligomers prepared therefrom. The monomers each comprise a nucleoside having at least one modification which is at a 2', 3' or 5'-sugar position or which can be at a heterocyclic base position. More than one position can be modified in either the nucleosidic monomers or oligomers of the invention. The oligomeric compounds of the invention are useful for identification or quantification of an RNA or DNA or for modulating the activity of an RNA or DNA molecule. The oligomeric compounds having a modified nucleosidic monomer therein are preferably prepared to be specifically hybridizable with a preselected nucleotide sequence of a single-stranded or double-stranded target DNA or RNA molecule. It is generally desirable to select a sequence of DNA or RNA which is involved in the production of a protein whose synthesis is ultimately to be modulated or inhibited in its entirety or to select a sequence of RNA or DNA whose presence, absence or specific amount is to be determined in a diagnostic test.

The nucleosidic monomers (monomers) of the invention are prepared having one or more aminooxy modifications. The sites for modification can be the 2', 3' and/or 5' positions on the sugar portion, and/or in the heterocyclic base moiety of the monomers. In preferred embodiments, the nucleosidic monomers are of the formula:

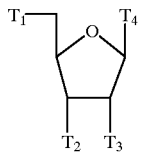

wherein:

$T_4$ is Bx or Bx—L where Bx is a heterocyclic base moiety;

one of $T_1$, $T_2$ and $T_3$ is L, hydrogen, hydroxyl, a protected hydroxyl or a sugar substituent group;

another one of $T_1$, $T_2$ and $T_3$ is L, hydroxyl, a protected hydroxyl, a connection to a solid support or an activated phosphorus group;

the remaining one of $T_1$, $T_2$ and $T_3$ is L, hydrogen, hydroxyl or a sugar substituent group provided that at least one of $T_1$, $T_2$, $T_3$ and $T_4$ is L or Bx—L;

said group L having one of the formulas;

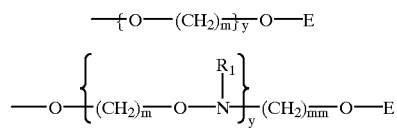

wherein:

each m and mm is, independently, from 1 to 10;

y is from 1 to 10;

E is $N(R_1)(R_2)$ or $N=C(R_1)(R_2)$;

each $R_1$ and $R_2$ is, independently, H, a nitrogen protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein said substitution is $OR_3$, $SR_3$, $NH_3^+$, $N(R_3)(R_4)$, guanidino or acyl where said acyl is an acid, amide or an ester;

or $R_1$ and $R_2$, together, are a nitrogen protecting group or are joined in a ring structure that optionally includes an additional heteroatom selected from N and O; and each $R_3$ and $R_4$ is, independently, H, $C_1$–$C_{10}$ alkyl, a nitrogen protecting group, or $R_3$ and $R_4$, together, are a nitrogen protecting group;

or $R_3$ and $R_4$ are joined in a ring structure that optionally includes an additional heteroatom selected from N and O.

While not wishing to be bound by a specific theory, the design of aminooxy-modified oligomeric compounds is focused on a number of factors that include: an electronegative atom at the 2'-connecting site, which is believed to be necessary for $C_{3'}$-endo conformation via $O_{4'}$—$O_{2'}$ gauche effect (increase in binding affinity); gauche effect of the 2'-substituent —O—$CH_2$—$CH_2$—O— (increase in binding affinity/nuclease resistance); restricted motion around N—O bond, as in calichiamycin, which is believed to lead to conformational constraints in side chain; lipophilicity of the modification (which relates to protein binding/absorption); and fusogenic properties of aminooxy side chains.

One of the factors believed to be related to the 2'-O-dimethylaminooxyethyl (DMAOE) substituent is the potential fusogenic property or "proton sponge hypothesis." The nitrogen of the DMAOE is expected to have pKa between 4.5 and 5.0. Thus, it is believed that this nitrogen probably will not be protonated outside the cell or in cell membranes, but is likely to be protonated inside the endosomes where pH is around 5.0. Such a protonation is expected to prevent the endosomal degradation of the oligonucleotide by lysosomal nucleases having an acidic optimal pH. Such a "proton sponge" is expected to alter the osmolarity of the endosomal vesicle. The accumulation of protons brought in by the endosomal ATPase is coupled to an influx of chloride anions. Concentration of DMAOE oligonucleotide in the endosome should cause an increase in the ionic concentration within the endosome, resulting in osmotic swelling of the endosome. Moreover, DMAOE protonation is believed to cause internal charge repulsion. Both of these effects are believed to cause endosomal fusion to release the oligonucleotide to the cytoplasm. Once the oligonucleotide is in the cytoplasm, it should be easily transported to the nucleus.

It is preferred that the oligonucleotides of the invention be adapted to be specifically hybridizable with the nucleotide sequence of the target RNA or DNA selected for modulation. Oligonucleotides particularly suited for the practice of one or more embodiments of the present invention comprise 2', 3', or 5'-sugar modified or heterocyclic base modified oligonucleotides wherein the modification is an aminooxy moiety. For example, the oligonucleotides are modified to contain substitutions including but not limited incorporation of one or more nucleoside units modified as shown in the formula defining "L" above. The modified nucleosidic compounds can be positioned internally in the oligonucleotide via linking in the oligonucleotide backbone or they can be located on one or both of the 3' and 5' terminal ends of the oligonucleotide.

The nucleosidic monomers of the present invention can include appropriate activated phosphorus groups such as activated phosphate groups and activated phosphite groups. As used herein, the terms activated phosphate and activated phosphite groups refer to activated monomers or oligomers that are reactive with a hydroxyl group of another monomeric or oligomeric compound to form a phosphorus-containing internucleotide linkage. Such activated phosphorus groups contain activated phosphorus atoms in $P^{III}$ or $P^V$ valency states. Such activated phosphorus atoms are known in the art and include, but are not limited to, phosphoramidite, H-phosphonate and phosphate triesters. A preferred synthetic solid phase synthesis utilizes phosphoramidites as activated phosphates. The phosphoramidites utilize $P^{III}$ chemistry. The intermediate phosphite compounds are subsequently oxidized to the $P^V$ state using known methods to yield, in preferred embodiments, phosphodiester or phosphorothioate internucleotide linkages. Additional activated phosphates and phosphites are disclosed in Tetrahedron Report Number 309 (Beaucage and Iyer, *Tetrahedron*, 1992, 48, 2223–2311).

The oligomers (oligomeric compounds) of the invention are conveniently synthesized using solid phase synthesis of known methodology, and are preferably designed to be complementary to or specifically hybridizable with a preselected nucleotide sequence of the target RNA or DNA. Standard solution phase and solid phase methods for the synthesis of oligonucleotides and oligonucleotide analogs are well known to those skilled in the art. These methods are constantly being improved in ways that reduce the time and cost required to synthesize these complicated compounds. Representative solution phase techniques are described in U.S. Pat. No. 5,210,264, issued May 11, 1993 and commonly assigned with this invention. Representative solid phase techniques employed for oligonucleotide and oligonucleotide analog synthesis utilizing standard phosphoramidite chemistries are described in, Protocols For Oligonucleotides And Analogs, Agrawal, S., ed., Humana Press, Totowa, N.J., 1993.

The oligomeric compounds of the invention also include those that comprise nucleosides connected by charged linkages, and whose sequences are divided into at least two regions. In some preferred embodiments, the first region includes 2'-aminooxyalkyl substituted-nucleosides linked by a first type of linkage, and the second region includes nucleosides linked by a second type of linkage. In seom preferred embodiments, the oligomers of the invention further include a third region comprised of nucleosides as are used in the first region, with the second region positioned between the first and the third regions. Such oligomeric compounds are known as "chimeras," "chimeric," or "gapped" oligonucleotides. (See, e.g., U.S. Pat. No. 5,623,065, issued Apr. 22, 1997, the contents of which are incorporated herein by reference.)

GAPmer technology has been developed to incorporate modifications at the ends ("wings") of oligomeric compounds, leaving a phosphorothioate Gap in the middle for RNase H activation (Cook, P. D., *Anti-Cancer Drug Des.*, 1991, 6, 585–607; Monia et al., *J. Biol. Chem*., 1993, 268, 14514–14522). In a recent report, the activities of a series of uniformly 2'-O modified 20 mer RNase H-independent oligonucleotides that were antisense to the 5'-cap region of human ICAM-1 transcript in HUVEC cells, were compared to the parent 2'-deoxy phosphorothioate oligonucleotide. See Baker et al., *J. Bio. Chem.*, 1997, 272, 11994–12000). The 2'-MOE/P=O oligomer demonstrated the greatest activity with a $IC_{50}$ of 2.1 nM ($T_m$=87.1° C.), while the parent P=S oligonucleotide analog had an $IC_{50}$ of 6.5 nM ($T_m$=79.2° C.) Correlation of activity with binding affinity was not always seen as the 2'-F/P=S ($T_m$=87.9° C.) was less active than the 2'-MOE/P=S ($T_m$=79.2° C.) by four fold. The RNase H competent 2'-deoxy P=S parent oligonucleotide exhibited an $IC_{50}$=41 nM.

In the context of this invention, the terms "oligomer" and "oligomeric compound" refer to a plurality of naturally occurring or non-naturally occurring nucleosides joined together in a specific sequence. "Oligomer" and "oligomeric compound" include oligonucleotides, oligonucleotide analogs and chimeric oligomeric compounds having non-phosphorus containing internucleoside linkages. In some preferred embodiments, each of the oligomeric compounds of the invention have at least one modified nucleoside where the modification is an aminooxy compound of the invention. Preferred nucleosides of the invention are joined through a sugar moiety via phosphorus linkages, and include those containing adenine, guanine, adenine, cytosine, uracil, thymine, xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydroxyl guanine and other 8-substituted guanines, other aza and deaza uracils, other aza and deaza thymidines, other aza and deaza cytosines, other aza and deaza adenines, other aza and deaza guanines, 5-trifluoromethyl uracil and 5-trifluoro cytosine.

Heterocyclic base moieties (often referred to in the art simply as the "base") amenable to the present invention include both naturally and non-naturally occurring nucleobases and heterocycles. As used herein, "unmodified" or "natural" nucleobases include the purine bases adenine and guanine, and the pyrimidine bases thymine, cytosine and uracil. Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the *Concise Encyclopedia Of Polymer Science And Engineering*, pages 858–859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Chapter 15, *Antisense Research and Applications*, pages 289–302, Crooke, S. T. and Lebleu, B., ed., CRC Press, 1993. Certain of these nucleobases are particularly useful for increasing the binding affinity of the oligonucleotides of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Id., pages 276–278) and are presently preferred base substitutions, even more particularly when combined with 2'-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, certain of which are commonly owned, and each of which is herein incorporated by reference, and commonly owned U.S. patent application Ser. No.08/762,587, now U.S. Pat. No. 5,808,027 filed on Dec. 10, 1996, also herein incorporated by reference.

The preferred sugar moieties are deoxyribose or ribose. However, other sugar substitutes known in the art are also amenable to the present invention.

As used herein, the term "sugar substituent groups" refer to groups that are attached to sugar moieties of compounds or oligomers of the invention. Sugar substituent groups are covalently attached at sugar 2', 3' and 5'-positions. In some preferred embodiments, the sugar substituent group has an oxygen atom bound directly to the 2', 3' and/or 5'-carbon atom of the sugar. Preferably, sugar substituent groups are attached at 2'-positions although sugar substituent groups may also be located at 3' and 5' positions.

Sugar substituent groups amenable to the present invention include fluoro, O-alkyl, O-alkylamino, O-alkylalkoxy, protected O-alkylamino, O-alkylaminoalkyl, O-alkyl imidazole, and polyethers of the formula (O-alkyl)$_m$, where m is 1 to about 10. Preferred among these polyethers are linear and cyclic polyethylene glycols (PEGs), and (PEG)-containing groups, such as crown ethers and those which are disclosed by Ouchi, et al., *Drug Design and Discovery* 1992, 9, 93, Ravasio, et al., *J. Org. Chem.* 1991, 56, 4329, and Delgardo et. al., *Critical Reviews* in *Therapeutic Drug Carrier Systems* 1992, 9, 249. Further sugar modifications are disclosed in Cook, P. D., *Anti-Cancer Drug Design*, 1991, 6, 585–607. Fluoro, O-alkyl, O-alkylamino, O-alkyl imidazole, O-alkylaminoalkyl, and alkyl amino substitution is described in U.S. patent application Ser. No. 08/398,901, allowed, filed Mar. 6, 1995, entitled Oligomeric Compounds having Pyrimidine Nucleotide(s) with 2' and 5' Substitutions, hereby incorporated by reference in its entirety.

Additional sugar substituent groups amenable to the present invention include —SR and —NR$_2$ groups, where each R is, independently, hydrogen, a protecting group or substituted or unsubstituted alkyl, alkenyl, or alkynyl. 2'-SR nucleosides are disclosed in U.S. Pat. No. 5,670,633, issued Sep. 23, 1997, hereby incorporated by reference in its entirety. The incorporation of 2'-SR monomer synthons are disclosed by Hamm et al., *J. Org. Chem.*, 1997, 62, 3415–3420. 2'-NR$_2$ nucleosides are disclosed by Goettingen, M., *J. Org. Chem.*, 1996, 61, 6273–6281; and Polushin et al., *Tetrahedron Lett.*, 1996, 37, 3227–3230.

Further representative sugar substituent groups amenable to the present invention include those having one of formula I or II:

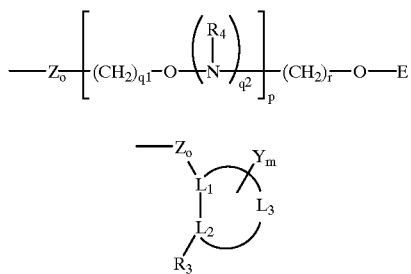

wherein
$Z_0$ is O, S or NH;
E is $C_1$–$C_{10}$ alkyl, N($R_4$)($R_5$) or N=C($R_4$)($R_5$);
each $R_4$ and $R_5$ is, independently, H, a nitrogen protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein said substitution is O$R_6$, S$R_6$, NH$_6^+$, N($R_6$)($R_7$), guanidino or acyl where said acyl is an acid amide or an ester;
or $R_4$ and $R_5$, together, are a nitrogen protecting group or are joined in a ring structure that optionally includes an additional heteroatom selected from N and O; and
each $R_6$ and $R_7$ is, independently, H, $C_1$–$C_{10}$ alkyl, a nitrogen protecting group, or $R_3$ and $R_4$, together, are a nitrogen protecting group;
or $R_6$ and $R_7$ are joined in a ring structure that optionally includes an additional heteroatom selected from N and O;

$R_3$ is OX, SX, or N(X)$_2$;
each X is, independently, H, $C_1$–$C_8$ alkyl, $C_1$–$C_8$ haloalkyl, C(=NH)N(H)Z, C(=O)N(H)Z or OC(=O)N(H)Z;
Z is H or $C_1$–$C_8$ alkyl;
$L_1$, $L_2$ and $L_3$ comprise a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic, or saturated or unsaturated heterocyclic;
Y is alkyl or haloalkyl having 1 to about 10 carbon atoms, alkenyl having 2 to about 10 carbon atoms, alkynyl having 2 to about 10 carbon atoms, aryl having 6 to about 14 carbon atoms, N($R_4$)($R_5$) O$R_4$, halo, S$R_4$ or CN;
each $q_1$ is, independently, from 2 to 10;
each $q_2$ is 0 or 1;
p is from 1 to 10; and
r is from 1 to 10 with the proviso that when p is 0, r is greater than 1.

Representative 2'-O- sugar substituents of formula I are disclosed in U.S. patent application Ser. No. 09/130,973, filed Aug. 7, 1998, entitled Capped 2'-Oxyethoxy Oligonucleotides, hereby incorporated by reference in its entirety.

Representative cyclic 2'-O- sugar substituents of formula II are disclosed in U.S. patent application Ser. No. 09/123, 108, filed Jul. 27, 1998, entitled RNA Targeted 2'-Modified Oligonucleotides that are Conformationally Preorganized, hereby incorporated by reference in its entirety.

Particularly preferred sugar substituent groups include O[(CH$_2$)$_n$O]$_m$CH$_3$, O(CH$_2$)$_n$OCH$_3$, O(CH$_2$)$_n$ $_{NH2}$, O(CH$_2$)$_n$CH$_3$, O(CH$_2$)$_n$ONH$_2$, and O(CH$_2$)$_n$ON[(CH$_2$)$_n$CH$_3$)]$_2$, where n and m are from 1 to about 10.

Some preferred oligomeric compounds of the invention contain at least one nucleoside having one of the following at the 2' position: $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy [2'-O-CH$_2$CH$_2$OCH$_3$, also known as 2'-O-(2-methoxyethyl) or 2'-MOE] (Martin et al., *Helv. Chim. Acta*, 1995, 78, 486), i.e., an alkoxyalkoxy group. A further preferred modification is 2'-dimethylaminooxyethoxy, i.e., a O(CH$_2$)$_2$ON(CH$_3$)$_2$ group, also known as 2'-DMAOE, as described in co-owned U.S. patent application Ser. No. 09/016,520, filed on Jan. 30, 1998, the contents of which are herein incorporated by reference.

Other preferred modifications include 2'-methoxy (2'-O-CH$_3$), 2'-aminopropoxy (2'-OCH$_2$CH$_2$CH$_2$NH$_2$) and 2'-fluoro (2'-F). Similar modifications may also be made at other positions on the oligonucleotide, particularly the 3' position of the sugar on the 3' terminal nucleotide or in 2'–5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920, certain of which are commonly owned, and each of which is herein incorporated by reference, and commonly owned U.S. patent application Ser. No. 08/468,037, now U.S. Pat. No. 5,859,221 filed on Jun. 5, 1995, also herein incorporated by reference.

Sugars having O-substitutions on the ribosyl ring are also amenable to the present invention. Representative substitutions for ring O include, but are not limited to, S, $CH_2$, CHF, and $CF_2$. See, e.g., Secrist et al., *Abstract 21, Program & Abstracts, Tenth International Roundtable, Nucleosides, Nucleotides and their Biological Applications,* Park City, Utah, Sep. 16–20, 1992, Additional modifications may also be made at other positions on the oligonucleotide, particularly the 3' position of the sugar on the 3' terminal nucleotide and the 5'-position of 5' terminal nucleotide. For example, one additional modification of the oligonucleotides of the present invention involves chemically linking to the oligonucleotide one or more moieties or conjugates which enhance the activity, cellular distribution or cellular uptake of the oligonucleotide. Such moieties include, but are not limited to, lipid moieties such as a cholesterol moiety (Letsinger et al., *Proc. Natl. Acad. Sci. USA,* 1989, 86, 6553), cholic acid (Manoharan et al., *Bioorg. Med. Chem. Lett.,* 1994, 4, 1053), a thioether, e.g., hexyl-S-tritylthiol (Manoharan et al., *Ann. N.Y. Acad. Sci.,* 1992, 660, 306; Manoharan et al., *Bioorg. Med. Chem. Let.,* 1993, 3, 2765), a thiocholesterol (Oberhauser et al., *Nucl. Acids Res.,* 1992, 20, 533), an aliphatic chain, e.g., dodecandiol or undecyl residues (Saison-Behmoaras et al., *EMBO J.,* 1991, 10, 111; Kabanov et al., *FEBS Lett.,* 1990, 259, 327; Svinarchuk et al., *Biochimie,* 1993, 75, 49), a phospholipid, e.g., di-hexadecyl-rac-glycerol or triethylammonium-1,2-di-O-hexadecyl-rac-glycero-3-H-phosphonate (Manoharan et al., *Tetrahedron Lett.,* 1995, 36, 3651; Shea et al., *Nucl. Acids Res.,* 1990, 18, 3777), a polyamine or a polyethylene glycol chain (Manoharan et al., *Nucleosides & Nucleotides,* 1995, 14, 969), adamantane acetic acid (Manoharan et al., *Tetrahedron Lett.,* 1995, 36, 3651), a palmityl moiety (Mishra et al., *Biochim. Biophys. Acta,* 1995, 1264, 229), or an octadecylamine or hexylamino-carbonyl-oxycholesterol moiety (Crooke et al., *J. Pharmacol. Exp. Ther.,* 1996, 277, 923).

Compounds of the invention can include ring structures that include a nitrogen atom (e.g., —N($R_1$)($R_2$) and —N($R_3$)($R_4$) where ($R_1$)($R_2$) and ($R_3$)($R_4$) each form cyclic structures about the respective N). The resulting ring structure is a heterocycle or a heterocyclic ring structure that can include further heteroatoms selected from N, O and S. Such ring structures may be mono-, bi- or tricyclic, and may be substituted with substituents such as oxo, acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, ODMT, alkylsulfonyl, nitro, sulfide, sulfone, sulfonamide, thiol and thioalkoxy. A preferred bicyclic ring structure that includes nitrogen is phthalimido.

Heterocyclic ring structures of the present invention can be fully saturated, partially saturated, unsaturated or with a polycyclic heterocyclic ring each of the rings may be in any of the available states of saturation. Heterocyclic ring structures of the present invention also include heteroaryl which includes fused systems including systems where one or more of the fused rings contain no heteroatoms. Heterocycles, including nitrogen heterocycles, according to the present invention include, but are not limited to, imidazole, pyrrole, pyrazole, indole, 1H-indazole, α-carboline, carbazole, phenothiazine, phenoxazine, tetrazole, triazole, pyrrolidine, piperidine, piperazine and morpholine groups. A more preferred group of nitrogen heterocycles includes imidazole, pyrrole, indole, and carbazole groups.

The present invention provides oligomeric compounds comprising a plurality of linked nucleosides wherein the preferred internucleoside linkage is a 3', 5'-linkage. Alternatively, 2', 5'-linkages can be used (as described in U.S. application Ser. No. 09/115,043, filed Jul. 14, 1998). A 2', 5'-linkage is one that covalently connects the 2'-position of the sugar portion of one nucleotide subunit with the 5'-position of the sugar portion of an adjacent nucleotide subunit.

The oligonucleotides of the present invention preferably are about 5 to about 50 bases in length. It is more preferred that the oligonucleotides of the invention have from 8 to about 30 bases, and even more preferred that from about 15 to about 25 bases be employed.

In positioning one of the nucleosidic monomers of the invention in an oligonucleotide, an appropriate blocked and activated monomer is incorporated in the oligonucleotides in the standard manner for incorporation of a normal blocked and active standard nucleotide. for example, a diisopropyl phosphoramidite nucleosidic monomer is selected that has an aminooxy moiety that is protected with, for example, a phthalimido protecting group. In addition, one of the hydroxyl groups of the nucleosidic monomer molecule, for example the 5'-hydroxyl, is protected with a dimethoxytrityl (DMT) protecting group, and the other hydroxyl group, (i.e., the 3'-hydroxyl group), bears a cyanoethyl protecting group. The nucleosidic monomer is added to the growing oligonucleotide by treating with the normal activating agents, as is known is the art, to react the phosphoramidite moiety with the growing oligonucleotide. This is followed by removal of the DMT group in the standard manner, as is known in the art, and continuation of elongation of the oligonucleotide with normal nucleotide amidite units as is standard in the art. If the nucleosidic monomer is an intermediate unit utilized during synthesis of the oligonucleotide, the nucleosidic monomer nucleoside is positioned in the interior of the oligonucleotide. If the nucleosidic monomer is the last unit linked to the oligonucleotide, the nucleosidic monomer will form the 5' most terminal moiety of the oligonucleotide. There are a plurality of alternative methods for preparing oligomeric compounds of the invention that are well known in the art. The phosphoramidite method illustrated above is meant as illustrative of one of these methods.

In the context of this specification, alkyl (generally $C_1$–$C_{10}$), alkenyl (generally $C_2$–$C_{10}$), and alkynyl (generally $C_2$–$C_{10}$) groups include but are not limited to substituted and unsubstituted straight chain, branch chain, and alicyclic hydrocarbons, including methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl and other higher carbon alkyl groups. Further examples include 2-methylpropyl, 2-methyl-4-ethylbutyl, 2,4-diethylbutyl, 3-propylbutyl, 2,8-dibutyldecyl, 6,6-dimethyloctyl, 6-propyl-6-butyloctyl, 2-methylbutyl, 2-methylpentyl, 3-methylpentyl, 2-ethylhexyl and other branched chain groups, allyl, crotyl, propargyl, 2-pentenyl and other unsaturated groups containing a pi bond, cyclohexane, cyclopentane, adamantane as well as other alicyclic groups, 3-penten-2-one, 3-methyl-2- butanol, 2-cyanooctyl, 3-methoxy-4-heptanal, 3-nitrobutyl, 4-isopropoxydodecyl, 4-azido-2-nitrodecyl, 5-mercaptononyl, 4-amino-1-pentenyl as well as other substituted groups.

Further, in the context of this invention, a straight chain compound means an open chain compound, such as an aliphatic compound, including alkyl, alkenyl, or alkynyl compounds; lower alkyl, alkenyl, or alkynyl as used herein include but are not limited to hydrocarbyl compounds from about 1 to about 6 carbon atoms. A branched compound, as used herein, comprises a straight chain compound, such as an alkyl, alkenyl, alkynyl compound, which has further straight or branched chains attached to the carbon atoms of the straight chain. A cyclic compound, as used herein, refers to closed chain compounds, i.e. a ring of carbon atoms, such as an alicyclic or aromatic compound. The straight, branched, or cyclic compounds may be internally interrupted, as in alkoxy or heterocyclic compounds. In the context of this invention, internally interrupted means that the carbon chains may be interrupted with heteroatoms such as O, N, or S. However, if desired, the carbon chain may have no heteroatoms.

In one aspect of the invention the overall length of the alkyl group appended to a nucleosidic monomer will be selected to be less than 11 with the aminooxy group positioned between the ends of the alkyl group. In certain preferred nucleoside monomers of the invention, it is preferred to position the aminooxy group with at least two methylene groups between it and either of the hydroxyl groups of the nucleoside monomer. This can be accomplished by any combination of methylene units in either the alkyl backbone or on the aminooxy side chain. As so positioned the oxygen atom of the aminooxy moiety and the oxygen atoms of the hydroxyl groups do not form acetal type structures. In other embodiments the aminooxy moiety is positioned with only one methylene group between it and one or the other of the hydroxyl groups forming an acetal type structure.

In substituted nucleosidic monomers of the invention, a first preferred group of substituents include 2'-O-aminoxyalkyl substituents. A further preferred group of substituents includes 2'-O-alkylaminooxyalkyl, 2'-O-dialkylaminooxyalkyl and 2'-O-monoalkylaminooxyalkyl, e.g., dimethylaminooxyethyl and ethylaminooxyethyl. An additional preferred group of substituents include precursor or blocked forms of these 2'-O-aminooxyalkyl substituents include phthalimido and formaldehyde adducts, i.e., phthalimido-N-oxy and formaloximyl groups. A more preferred group of substituents includes 2'-aminooxyalkyl where the amino group is substituted with one or more substituted alkyl groups where preferred substitutions are amino and substituted amino.

In certain preferred embodiments of the present invention, oligomeric compounds are linked via phosphorus linkages. Preferred phosphorus linkages include phosphodiester, phosphorothioate and phosphorodithioate linkages. In one preferred embodiment of this invention, nuclease resistance is conferred on the oligonucleotides by utilizing phosphorothioate internucleoside linkages.

As used herein, the term oligonucleoside includes oligomers or polymers containing two or more nucleoside subunits having a non-phosphorous linking moiety. Oligonucleosides according to the invention have monomeric subunits or nucleosides having a ribofuranose moiety attached to a heterocyclic base moiety through a glycosyl bond.

Oligonucleotides and oligonucleosides can be joined to give a chimeric oligomeric compound. In addition to the naturally occurring phosphodiester linking group, phosphorus and non-phosphorus containing linking groups that can be used to prepare oligonucleotides, oligonucleosides and oligomeric chimeric compounds (oligomeric compounds) of the invention are well documented in the prior art and include without limitation the following:

phosphorus containing linkaqes phosphorodithioate (—O—P(S)(S)—O—);

phosphorothioate (—O—P(S)(O)—O—);

phosphoramidate (—O—P(O)(NJ)—O—);

phosphonate (—O—P(J)(O)—O—);

phosphotriesters (—O—P(O J)(O)—O—);

phophosphoramidate (—O—P(O)(NJ)—S—);

thionoalkylphosphonate (—O—P(S)(J)—O—);

thionoalkylphosphotriester (—O—P(O)(OJ)—S—);

boranophosphate (—$R^5$—P(O)(O)—J—);

non-phosphorus containing linkages thiodiester (—O—C(O)—S—);

thionocarbamate (—O—C(O)(NJ)—S—);

siloxane (—O—Si(J)$_2$—O—);

carbamate (—O—C(O)—NH— and —NH—C(O)—O—)

sulfamate (—O—S(O)(O)—N— and —N—S(O)(O)—N—;

morpholino sulfamide (—O—S(O)(N(morpholino)—);

sulfonamide (—O—SO$_2$—NH—);

sulfide (—CH$_2$—S—CH$_2$—);

sulfonate (—O—SO$_2$—CH$_2$—)

N,N'-dimethylhydrazine (—CH$_2$—N(CH$_3$)—N(CH$_3$)—);

thioformacetal (—S—CH$_2$—O—);

formacetal (—O—CH$_2$—O—);

thioketal (—S—C(J)$_2$—O—); and ketal (—O—C(J)$_2$—O—);

amine (—NH—CH$_2$—CH$_2$—)

hydroxylamine (—CH$_2$—N(J)—O—);

hydroxylimine (—CH=N—O—); and hydrazinyl (—CH$_2$—N(H)—N(H)—).

"J" denotes a substituent group which is commonly hydrogen or an alkyl group, but which can be a more complicated group that varies from one type of linkage to another.

In addition to linking groups as described above that involve the modification or substitution of one or more of the —O—P(O)$_2$—O— atoms of a naturally occurring linkage, included within the scope of the present invention are linking groups that include modification of the 5'-methylene group as well as one or more of the atoms of the naturally occurring linkage. Linkages of this type are well documented in the literature and include without limitation the following:

amides (—CH$_2$—CH$_2$—N(H)—C(O)) and —CH$_2$—O—N=CH—; and alkylphosphorus (—C(J)$_2$—P(=O)(OJ)—C(J)$_2$—C(J)$_2$—).

wherein J is as described above.

Synthetic schemes for the synthesis of the substitute internucleoside linkages described above are disclosed in: WO 91/08213; WO 90/15065; WO 91/15500; WO 92/20822; WO 92/20823; WO 91/15500; WO 89/12060; EP 216860; U.S. Pat. Nos. 9,204,294; 9,003,138; 9,106,855; 9,203,385; 9,103,680; U.S. Pat. Ser. Nos. 07/990,848;

07,892,902; 07/806,710; 07/763,130; 07/690,786; U.S. Pat. No. 5,466,677; 5,034,506; 5,124,047; 5,278,302; 5,321,131; 5,519,126; 4,469,863; 5,455,233; 5,214,134; 5,470,967; 5,434,257; Stirchak, E. P., et al., *Nucleic Acid Res.*, 1989, 17, 6129–6141; Hewitt, J. M., et al., 1992, 11, 1661–1666; Sood, A., et al., *J. Am. Chem. Soc.*, 1990, 112, 9000–9001; Vaseur, J. J. et al., *J. Amer. Chem. Soc.*, 1992, 114, 4006–4007; Musichi, B., et al., *J. Org. Chem.*, 1990, 55, 4231–4233; Reynolds, R. C., et al., *J. Org. Chem.*, 1992, 57, 2983–2985; Mertes, M. P., et al., *J. Med. Chem.*, 1969, 12, 154–157; Mungall, W. S., et al., *J. Org. Chem.*, 1977, 42, 703–706; Stirchak, E. P., et al.., *J. Org. Chem.*, 1987, 52, 4202–4206; Coull, J. M., et al., *Tet. Lett.*, 1987, 28, 745; and Wang, H., et al., *Tet. Lett.*, 1991, 32, 7385–7388.

Other modifications can be made to the sugar, to the base, or to the phosphate group of the nucleotide. Representative modifications are disclosed in International Publication Numbers WO 91/10671, published Jul. 25, 1991, WO 92/02258, published Feb. 20, 1992, WO 92/03568, published Mar. 5, 1992, and U.S. Pat. Nos. 5,138,045, 5,218, 105, 5,223,618 5,359,044, 5,378,825, 5,386,023, 5,457,191, 5,459,255, 5,489,677, 5,506,351, 5,541,307, 5,543,507, 5,571,902, 5,578,718, 5,587,361, 5,587,469, all assigned to the assignee of this application. The disclosures of each of the above referenced U.S. patents are herein incorporated by reference.

The attachment of conjugate groups to oligonucleotides and analogs thereof is well documented in the prior art. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, phospholipids, biotin, phenazine, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992, U.S. Pat. No. 5,578,718, issued Jul. 1, 1997, and U.S. Pat. No. 5,218,105. Each of the above U.S. patents of the foregoing is commonly assigned with this application. The entire disclosure of each U.S. patent is incorporated herein by reference.

Other groups for modifying antisense properties include RNA cleaving complexes, pyrenes, metal chelators, porphyrins, alkylators, hybrid intercalator/ligands and photo-crosslinking agents. RNA cleavers include o-phenanthroline/Cu complexes and $Ru(bipyridine)_3^{2+}$ complexes. The $Ru(bpy)_3^{2+}$ complexes interact with nucleic acids and cleave nucleic acids photochemically. Metal chelators are include EDTA, DTPA, and o-phenanthroline. Alkylators include compounds such as iodoacetamide. Porphyrins include porphine, its substituted forms, and metal complexes. Pyrenes include pyrene and other pyrene-based carboxylic acids that could be conjugated using the similar protocols.

Hybrid intercalator/ligands include the photonuclease/intercalator ligand 6-[[[9-[[6-(4-nitrobenzamido)hexyl]amino]acridin-4-yl]carbonyl]amino]hexanoyl-pentafluorophenyl ester. This compound has two noteworthy features: an acridine moiety that is an intercalator and a p-nitro benzamido group that is a photonuclease.

Photo-crosslinking agents include aryl azides such as, for example, N-hydroxysucciniimidyl-4-azidobenzoate (HSAB) and N-succinimidyl-6(-4'-azido-2'-nitrophenyl-amino)hexanoate (SANPAH). Aryl azides conjugated to oligonucleotides effect crosslinking with nucleic acids and proteins upon irradiation. They also crosslink with carrier proteins (such as KLH or BSA), raising antibody against the oligonucleotides.

Vitamins according to the invention generally can be classified as water soluble or lipid soluble. Water soluble vitamins include thiamine, riboflavin, nicotinic acid or niacin, the vitamin $B_6$ pyridoxal group, pantothenic acid, biotin, folic acid, the $B_{12}$ cobamide coenzymes, inositol, choline and ascorbic acid. Lipid soluble vitamins include the vitamin A family, vitamin D, the vitamin E tocopherol family and vitamin K (and phytols). The vitamin A family, including retinoic acid and retinol, are absorbed and transported to target tissues through their interaction with specific proteins such as cytosol retinol-binding protein type II (CRBP-II), Retinol-binding protein (RBP), and cellular retinol-binding protein (CRBP). These proteins, which have been found in various parts of the human body, have molecular weights of approximately 15 kD. They have specific interactions with compounds of vitamin-A family, especially, retinoic acid and retinol.

In the context of this invention, "hybridization" shall mean hydrogen bonding, which may be Watson-Crick, Hoogsteen or reversed Hoogsteen hydrogen bonding, between complementary nucleotides. For example, adenine and thymine are complementary nucleobases which pair through the formation of hydrogen bonds. "Complementary," as used herein, also refers to sequence complementarity between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity such that stable and specific binding occurs between the oligonucleotide and the DNA or RNA target. It is understood that an oligonucleotide need not be 100% complementary to its target DNA sequence to be specifically hybridizable. An oligonucleotide is specifically hybridizable when binding of the oligonucleotide to the target DNA or RNA molecule interferes with the normal function of the target DNA or RNA, and there is a sufficient degree of complementarity to avoid non-specific binding of the oligonucleotide to non-target sequences under conditions in which specific binding is desired, i.e. under physiological conditions in the case of in vivo assays or therapeutic treatment, or in the case of in vitro assays, under conditions in which the assays are performed.

Cleavage of oligonucleotides by nucleolytic enzymes requires the formation of an enzyme-substrate complex, or in particular, a nuclease-oligonucleotide complex. The nuclease enzymes will generally require specific binding sites located on the oligonucleotides for appropriate attachment. If the oligonucleotide binding sites are removed or blocked, such that nucleases are unable to attach to the oligonucleotides, the oligonucleotides will be nuclease resistant. In the case of restriction endonucleases that cleave sequence-specific palindromic double-stranded DNA, certain binding sites such as the ring nitrogen in the 3- and 7-positions have been identified as required binding sites. Removal of one or more of these sites or sterically blocking approach of the nuclease to these particular positions within the oligonucleotide has provided various levels of resistance to specific nucleases.

This invention provides oligonucleotides possessing superior hybridization properties. Structure-activity relationship studies have revealed that an increase in binding ($T_m$) of certain 2'-sugar modified oligonucleotides to an RNA target (complement) correlates with an increased "A" type conformation of the heteroduplex. Furthermore, absolute fidelity of the modified oligonucleotides is maintained. Increased binding of 2'-sugar modified sequence-specific oligonucleotides of the invention provides superior potency and specificity compared to phosphorus-modified oligonucleotides such as methyl phosphonates, phosphate triesters and phosphoramidates as known in the literature.

The only structural difference between DNA and RNA duplexes is a hydrogen atom at the 2'-position of the sugar moiety of a DNA molecule versus a hydroxyl group at the 2'-position of the sugar moiety of an RNA molecule (assuming that the presence or absence of a methyl group in the uracil ring system has no effect). However, gross conformational differences exist between DNA and RNA duplexes.

It is known from X-ray diffraction analysis of nucleic acid fibers (Arnott and Hukins, *Biochem. Biophys. Res. Comm.*, 1970, 47, 1504) and analysis of crystals of double-stranded nucleic acids that DNA takes a "B" form structure and RNA takes the more rigid "A" form structure. The difference between the sugar puckering (C2' endo for "B" form DNA and C3' endo for "A" form RNA) of the nucleosides of DNA and RNA is the major conformational difference between double-stranded nucleic acids.

The primary contributor to the conformation of the pentofuranosyl moiety is the nature of the substituent at the 2'-position. Thus, the population of the C3'-endo form increases with respect to the C2'-endo form as the electronegativity of the 2'-substituent increases. For example, among 2'-deoxy-2'-haloadenosines, the 2'-fluoro derivative exhibits the largest population (65%) of the C3'-endo form, and the 2'-iodo exhibits the lowest population (7%). Those of adenosine (2'-OH) and deoxy-adenosine (2'-H) are 36% and 19%, respectively. Furthermore, the effect of the 2'-fluoro group of adenosine dimers (2'-deoxy-2'-fluoroadenosine-2'-deoxy-2'-fluoroadenosine) is further correlated to the stabilization of the stacked conformation. Research indicates that dinucleoside phosphates have a stacked conformation with a geometry similar to that of A—A but with a greater extent of base-base overlapping than A—A. It is assumed that the highly polar nature of the C2'-F bond and the extreme preference for C3'-endo puckering may stabilize the stacked conformation in an "A" structure.

Data from UV hypochromicity, circular dichroism, and $^1$H NMR also indicate that the degree of stacking decreases as the electronegativity of the halo substituent decreases. Furthermore, steric bulk at the 2'-position of the sugar moiety is better accommodated in an "A" form duplex than a "B" form duplex.

Thus, a 2'-substituent on the 3'-nucleotidyl unit of a dinucleoside monophosphate is thought to exert a number of effects on the stacking conformation: steric repulsion, furanose puckering preference, electrostatic repulsion, hydrophobic attraction, and hydrogen bonding capabilities. These substituent effects are thought to be determined by the molecular size, electronegativity, and hydrophobicity of the substituent.

Studies with a 2'-OMe modification of 2'-deoxy guanosine, cytidine, and uridine dinucleoside phosphates exhibit enhanced stacking effects with respect to the corresponding unmethylated species (2'-OH). In this case, it is believed that the hydrophobic attractive forces of the methyl group tend to overcome the destablilizing effects of its steric bulk.

Melting temperatures (complementary binding) are increased with the 2'-substituted adenosine diphosphates. It is not clear whether the 3'-endo preference of the conformation or the presence of the substituent is responsible for the increased binding. However, greater overlap of adjacent bases (stacking) can be achieved with the 3'-endo conformation.

While we do not wish to be bound by theory, it is believed that the aminooxyalkyl substituents of the present invention also result in the sugar pucker of the nucleoside being C3'-endo puckering.

Compounds of the invention can be utilized as diagnostics, therapeutics and as research reagents and kits. They can be utilized in pharmaceutical compositions by adding an effective amount of an oligonucleotide of the invention to a suitable pharmaceutically acceptable diluent or carrier. They further can be used for treating organisms having a disease characterized by the undesired production of a protein. The organism can be contacted with an oligonucleotide of the invention having a sequence that is capable of specifically hybridizing with a strand of target nucleic acid that codes for the undesirable protein.

The formulation of therapeutic compositions and their subsequent administration is believed to be within the skill of those in the art. In general, for therapeutics, a patient in need of such therapy is administered an oligomer in accordance with the invention, commonly in a pharmaceutically acceptable carrier, in doses ranging from 0.01 μg to 100 g per kg of body weight depending on the age of the patient and the severity of the disease state being treated. Further, the treatment may be a single dose or may be a regimen that may last for a period of time which will vary depending upon the nature of the particular disease, its severity and the overall condition of the patient, and may extend from once daily to once every 20 years. Following treatment, the patient is monitored for changes in his/her condition and for alleviation of the symptoms of the disease state. The dosage of the oligomer may either be increased in the event the patient does not respond significantly to current dosage levels, or the dose may be decreased if an alleviation of the symptoms of the disease state is observed, or if the disease state has been ablated.

In some cases it may be more effective to treat a patient with an oligomer of the invention in conjunction with other traditional therapeutic modalities. For example, a patient being treated for AIDS may be administered an oligomer in conjunction with AZT, or a patient with atherosclerosis may be treated with an oligomer of the invention following angioplasty to prevent reocclusion of the treated arteries.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient.

Persons of ordinary skill can easily determine optimum dosages, dosing methodologies and repetition rates. Optimum dosages may vary depending on the relative potency of individual oligomers, and can generally be estimated based on $EC_{50}$s found to be effective in in vitro and in vivo animal models. In general, dosage is from 0.01 μg to 100 g per kg of body weight, and may be given once or more daily, weekly, monthly or yearly, or even once every 2 to several years.

Following successful treatment, it may be desirable to have the patient undergo maintenance therapy to prevent the recurrence of the disease state, wherein the oligomer is administered in maintenance doses, ranging from 0.01 μg to 100 g per kg of body weight, once or more daily, to once every several years.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for intrathecal or intraventricular administration may include sterile aqueous solutions which may also contain buffers, diluents and other suitable additives.

Formulations for parenteral administration may include sterile aqueous solutions which may also contain buffers, diluents and other suitable additives.

The present invention can be practiced in a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular machinery is susceptible to such therapeutic and/or prophylactic treatment. Seemingly diverse organisms such as bacteria, yeast, protozoa, algae, plant and higher animal forms, including warm-blooded animals, can be treated in this manner. Further, since each of the cells of multicellular eukaryotes also includes both DNA-RNA transcription and RNA-protein translation as an integral part of their cellular activity, such therapeutics and/or diagnostics can also be practiced on such cellular populations. Furthermore, many of the organelles, e.g. mitochondria and chloroplasts, of eukaryotic cells also include transcription and translation mechanisms. As such, single cells, cellular populations or organelles also can be included within the definition of organisms that are capable of being treated with the therapeutic or diagnostic oligonucleotides of the invention. As used herein, therapeutics is meant to include both the eradication of a disease state, killing of an organism, e.g. bacterial, protozoan or other infection, or control of aberrant or undesirable cellular growth or expression.

The current method of choice for the preparation of naturally occurring oligonucleotides, as well as modified oligonucleotides such as phosphorothioate oligonucleotides, is via solid-phase synthesis wherein an oligonucleotide is prepared on a polymer support (a solid support) such as controlled pore glass (CPG); oxalyl-controlled pore glass (see, e.g., Alul, et al., Nucleic Acids Research 1991, 19, 1527); TENTAGEL Support, (see, e.g., Wright, et al., Tetrahedron Letters 1993, 34, 3373); or POROS, a polystyrene resin available from Perceptive Biosystems. Equipment for such synthesis is sold by several vendors including, for example, Applied Biosystems (Foster City, Calif.). Any other means for such synthesis known in the art may additionally or alternatively be employed. Suitable solid phase techniques, including automated synthesis techniques, are described in F. Eckstein (ed.), Oligonucleotides and Analogues, a Practical Approach, Oxford University Press, New York (1991).

Solid-phase synthesis relies on sequential addition of nucleotides to one end of a growing oligonucleotide chain. Typically, a first nucleoside (having protecting groups on any exocyclic amine functionalities present) is attached to an appropriate glass bead support and activated phosphite compounds (typically nucleotide phosphoramidites, also bearing appropriate protecting groups) are added stepwise to elongate the growing oligonucleotide. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069.

Solid supports according to the invention include controlled pore glass (CPG), oxalyl-controlled pore glass (see, e.g., Alul, et al., Nucleic Acids Research 1991, 19, 1527), TentaGel Support—an aminopolyethyleneglycol derivatized support (see, e.g., Wright, et al., Tetrahedron Letters 1993, 34, 3373) or Poros—a copolymer of polystyrene/divinylbenzene.

2'-Substituted oligonucleotides were synthesized by standard solid phase nucleic acid synthesis using an automated synthesizer such as Model 380B (Perkin-Elmer/Applied Biosystems) or MilliGen/Biosearch 7500 or 8800. Triester, phosphoramidite, or hydrogen phosphonate coupling chemistries (Oligonucleotides: Antisense Inhibitors of Gene Expression. M. Caruthers, p. 7, J. S. Cohen (Ed.), CRC Press, Boca Raton, Fla., 1989) are used with these synthesizers to provide the desired oligonucleotides. The Beaucage reagent (J. Amer. Chem. Soc., 1990, 112, 1253) or elemental sulfur (Beaucage et al., Tet. Lett., 1981, 22, 1859) is used with phosphoramidite or hydrogen phosphonate chemistries to provide 2'-substituted phosphorothioate oligonucleotides.

The requisite 2'-substituted nucleosides (A, G, C, T (U), and other nucleosides having modified nucleobases and or additional sugar modifications) are prepared, utilizing procedures as described below.

During the synthesis of nucleosides and oligonucleotides of the invention, chemical protecting groups can be used to facilitate conversion of one or more functional groups while other functional groups are rendered inactive. A number of chemical functional groups can be introduced into compounds of the invention in a blocked form and subsequently deblocked to form a final, desired compound. In general, a blocking group renders a chemical functionality of a molecule inert to specific reaction conditions and can later be removed from such functionality in a molecule without substantially damaging the remainder of the molecule (Green and Wuts, Protective Groups in Organic Synthesis, 2d edition, John Wiley & Sons, New York, 1991). For example, amino groups can be blocked as phthalimido groups, as 9-fluorenylmethoxycarbonyl (FMOC) groups, and with triphenylmethylsulfenyl, t-BOC, benzoyl or benzyl groups. Carboxyl groups can be protected as acetyl groups. Representative hydroxyl protecting groups are described by Beaucage et al., Tetrahedron 1992, 48, 2223. Preferred hydroxyl protecting groups are acid-labile, such as the trityl, monomethoxytrityl, dimethoxytrityl, trimethoxytrityl, 9-phenylxanthine-9-yl (Pixyl) and 9-(p-methoxyphenyl) xanthine-9-yl (MOX) groups. Chemical functional groups can also be "blocked" by including them in a precursor form. Thus, an azido group can be used considered as a "blocked" form of an amine since the azido group is easily converted to the amine. Representative protecting groups utilized in oligonucleotide synthesis are discussed in Agrawal, et al., Protocols for Oligonucleotide Conjugates, Eds, Humana Press; New Jersey, 1994; Vol. 26 pp. 1–72.

Among other uses, the oligonucleotides of the invention are useful in a ras-luciferase fusion system using rasluciferase transactivation. As described in International Publication Number WO 92/22651, published Dec. 23, 1992 and U.S. Pat. Nos. 5,582,972 and 5,582,986, commonly assigned with this application, the entire contents of each of the above U.S. patents are herein incorporated by reference, the ras oncogenes are members of a gene family that encode related proteins that are localized to the inner face of the plasma membrane. Ras proteins have been shown to be highly conserved at the amino acid level, to bind GTP with high affinity and specificity, and to possess GTPase activity. Although the cellular function of ras gene products is unknown, their biochemical properties, along with their significant sequence homology with a class of signaltransducing proteins known as GTP binding proteins, or G proteins, suggest that ras gene products play a fundamental role in basic cellular regulatory functions relating to the transduction of extracellular signals across plasma membranes.

Three ras genes, designated H-ras, K-ras, and N-ras, have been identified in the mammalian genome. Mammalian ras genes acquire transformation-inducing properties by single point mutations within their coding sequences. Mutations in naturally occurring ras oncogenes have been localized to codons 12, 13, and 61. The most commonly detected activating ras mutation found in human tumors is in codon-12 of the H-ras gene in which a base change from GGC to GTC results in a glycine-to-valine substitution in the GTPase regulatory domain of the ras protein product. This single amino acid change is thought to abolish normal control of ras protein function, thereby converting a normally regulated cell protein to one that is continuously active. It is believed that such deregulation of normal ras protein function is responsible for the transformation from normal to malignant growth.

In addition to modulation of the ras gene, the oligonucleotides of the present invention that are specifically hybridizable with other nucleic acids can be used to modulate the expression of such other nucleic acids. Examples include the raf gene, a naturally present cellular gene which occasionally converts to an activated form that has been implicated in abnormal cell proliferation and tumor formation. Other examples include those relating to protein kinase C (PKC) that have been found to modulate the expression of PKC, those related to cell adhesion molecules such as ICAM, those related to multi-drug resistance associated protein, and viral genomic nucleic acids include HIV, herpesviruses, Epstein-Barr virus, cytomegalovirus, papillomavirus, hepatitis C virus and influenza virus (see U.S. Pat. Nos. 5,166, 195, 5,242,906, 5,248,670, 5,442,049, 5,457,189, 5,510,476, 5,510,239, 5,514,577, 5,514,786, 5,514,788, 5,523,389, 5,530,389, 5,563,255, 5,576,302, 5,576,902, 5,576,208, 5,580,767, 5,582,972, 5,582,986, 5,591,720, 5,591,600 and 5,591,623, commonly assigned with this application, the disclosures of which are herein incorporated by reference).

As will be recognized, the steps of the methods of the present invention need not be performed any particular number of times or in any particular sequence. Additional objects, advantages, and novel features of this invention will become apparent to those skilled in the art upon examination of the following examples thereof, which are intended to be illustrative and not intended to be limiting.

EXAMPLE 1

Methyl-2-O-(2-ethylacetyl)-3,5-bis-O-(2,4-dichlorobenzyl)-α-D-ribofuranoside (3, FIG. 1)

Compound 2 (FIG. 1) (multigram quantities of 2 were prepared from 1 via the literature procedure, Martin, P. Helv. Chem. Acta, 1995, 78, 486–504) was dissolved in DMF (86 mL) with cooling to 5° C., and NaH (60% dispersion, 1.38 g, 34.38 mmol) was added. The reaction mixture was stirred at 5° C. for 5 minutes then warmed to ambient temperature and stirred for 20 minutes after which time the reaction mixture was cooled to 5° C. and ethylbromoacetate (3.81 mL, 34.4 mmol) was added dropwise resulting in the evolution of gas. The reaction mixture was allowed to warm to ambient temperature and stirred for 3 hours after which time the mixture was cooled to 5° C. and the pH was adjusted to 3 with saturated aqueous $NH_4Cl$. The solvent was evaporated in vacuo to give a syrup which was dissolved in EtOAc (200 mL), washed with water and then brine. The organic layer was separated, dried with $MgSO_4$, and the solvent was evaporated in vacuo to give an oil. The oil was purified by flash chromatography using hexanes-EtOAc, 60:40, to give the title compound (3) as an oil (15.52 g, 95%). $^1H$ NMR ($CDCl_3$): δ7.58–7.18 (m, 6H), 5.05 (d, J=3.8 Hz, 1H), 4.79 (q, $J_{AB}$=13.7 Hz, 2H), 4.57 (d, J=2.8 Hz, 2H), 4.31–4.16 (m, 5H), 4.03 (m, 2H), 3.62 (d, 2H), 3.50 (s, 3H), 1.28 (t, 3H). $^{13}C$ NMR ($CDCl_3$): δ 170.0, 134.2, 133.6, 133.5, 130.3, 129.8, 129.1, 128.8, 127.1, 102.1, 81.4, 78.9, 76.6, 70.6, 70.0, 69.3, 67.6, 61.0, 55.6, 14.2. Anal. Calcd for $C_{24}H_{26}Cl_4O_7 \cdot H_2O$: C, 49.17; H, 4.81. Found: C, 49.33; H, 4.31.

EXAMPLE 2

1-[2'-O-(2-ethylacetyl)-3',5'-bis-O-(2,4-dichlorobenzyl)-β-D-ribofuranosyl]thymine (4, FIG. 1)

Thymine (6.90 g, 54.6 mmol) was suspended in anhydrous dichloroethane (136 mL) and bistrimethylsilylacetamide (40.5 mL, 164 mmol) was added. The reaction mixture was heated to reflux temperature for 10 minutes to give dissolution. After cooling to ambient temperature, the solution was added to compound 3 with stirring. Trimethylsilyl trifluoromethanesulfonate (6.86 mL, 35.5 mmol) was added and the reaction mixture was heated to reflux for 6 hours. The mixture was cooled to 5° C. and the pH was adjusted to 7 by the slow addition of saturated $NaHCO_3$. The mixture was extracted with $CH_2Cl_2$ (3×150 mL) and the organic extracts were combined, washed with brine, and the solvent was evaporated in vacuo to give an oil. The oil was dissolved in $CH_2Cl_2$ and purified by flash chromatography using hexanes-EtOAc, 45:55, to provide the title compound (4) as an oil (7.92 g, 44%). (The α-anomer was contained in a later fraction). $^1H$ NMR (400 MHZ, $CDCl_3$): δ8.25 (s, 1H), 7.67 (s, 1H), 7.46–7.21 (m, 6H), 5.94 (d, J=1.6 Hz, 1H), 4.80 (q, $J_{AB}$=12.4 Hz, 2H), 4.70–4.18 (m, 9H), 4.02 (d, 1H), 3.75 (d, 1H), 1.58 (s, 3H), 1.26 (t, 3H). $^{13}$C NMR (CDCl$_3$): 5 170.1, 164.3, 150.3, 135.5, 134.5, 134.2, 134.1, 133.8, 133.5, 130.7, 130.2, 129.4, 129.0, 127.1, 110.3, 88.4, 80.8, 80.5, 74.7, 70.1, 68.9, 68.0, 66.2, 60.9, 14.1, 12.1. Anal. Calcd for $C_{28}H_{28}Cl_4N_2O_8 \cdot H_2O$: C, 49.43; H, 4.44; N, 4.12. Found: C, 49.25; H, 4.10; N, 3.94.

EXAMPLE 3

1-[2'-O-(2-hydroxyethyl)-3',5'-bis-O-(2,4-dichlorobenzyl)-β-D-ribofuranosyl]thymine (5, FIG. 1)

Compound 4 (9.92 g, 15.0 mmol) was dissolved in hot EtOH (150 mL) and the solution was cooled to ambient temperature in a water bath. To the solution was cautiously added NaBH$_4$ (1.13 g, 30.0 mmol) over 10 minutes. After 3 hours additional NaBH$_4$ (282 mg, 7.45 mmol) was added the mixture was stirred for 1 hour and left to stand for 8 hours. The pH was adjusted to 4 by addition of Saturated NH$_4$Cl (25 mL) to give a gum. The solvent was decanted and evaporated in vacuo to afford a white solid which was dissolved in CH$_2$Cl$_2$ (250 mL). The gum was dissolved with saturated aqueous NaHCO$_3$ and this solution was gently extracted with the CH$_2$Cl$_2$ containing the product. The organic layer was separated and the aqueous layer was extracted again with CH$_2$Cl$_2$ (2×50 mL). After combining the organic layers, the solvent was dried over MgSO$_4$ and evaporated in vacuo to afford a white foam. The foam was dissolved in CH$_2$Cl$_2$ and purified by flash chromatography using hexanes-EtOAc, 20:80, to give the title compound (5) as a white foam (8.39 g, 90%). $^1$H NMR (CDCl$_3$): δ10.18 (s, 1H), 7.66 (s, 1H), 7.39–7.20 (m, 6H), 5.96 (s, 1H), 4.76–3.62 (m, 14H), 1.58 (s, 3H). $^{13}$C NMR (CDCl$_3$): δ164.0, 150.8, 135.2, 134.6, 134.2, 134.1, 133.5, 133.4, 130.2, 129.4, 129.0, 127.1, 110.6, 88.6, 81.0, 80.7, 75.2, 72.0, 70.1, 68.9, 68.1, 61.9, 12.1.

EXAMPLE 4

1-[2'-O-(2-phthalimido-N-hydroxyethyl)-3',5'-bis-O-(2,4-dichlorobenzyl)-β-D-ribofuranosyl]thymine (6, FIG. 1)

Compound 5 was dried by coevaporation with anhydrous acetonitrile followed by further drying in vacuo (0.1 torr) at ambient temperature for 12 h. The dried material (8.39 g, 13.53 mmol) was dissolved in freshly distilled THF (97 mL), PPh$_3$ (3.90 g, 14.9 mmol), and N-hydroxyphthalimide (2.43 g, 14.9 mmol) was added. The reaction mixture was cooled to −78 ° C., and diethyl azodicarboxylate (2.34 mL, 14.9 mmol) was added. The reaction mixture was warmed to ambient temperature and the solvent was evaporated in vacuo to give a foam. The foam was dissolved in EtOAc (100 mL) and washed with saturated aqueous NaHCO$_3$ (3×30 mL). The organic layer was separated, washed with brine, dried over MgSO$_4$, and the solvent evaporated to give a foam. The foam was purified by flash chromatography using CH$_2$Cl$_2$-acetone, 85:15, to give the title compound (6) as a white foam (3.22 g, 31%). A second chromatographic purification provided additional 6 as a white foam (5.18 g, 50%). $^1$H NMR (400 MHZ, CDCl$_3$): δ9.0 (s, 1H), 7.8 (m, 11H), 5.95 (s, 1H), 4.84–3.70 (m, 13H), 1.60 (s, 3H). $^{13}$C NMR (100 MHZ, CDCl$_3$): δ163.7, 163.5, 150.2, 138.0, 135.6, 134.5, 134.1, 134.0, 133.9, 133.7, 133.6, 130.6. 130.4, 130.1, 129.8, 129.4, 129.1, 129.0, 128.8, 127.2, 123.5, 110.4, 88.2, 81.0, 80.9, 77.6, 75.4, 70.2, 68.9, 68.4, 68.1., 12.1. LRMS (FAB+) m/z: 766 (M+H). LRMS (FAB−) m/z: 764 (M−H).

EXAMPLE 5

Figure 2:
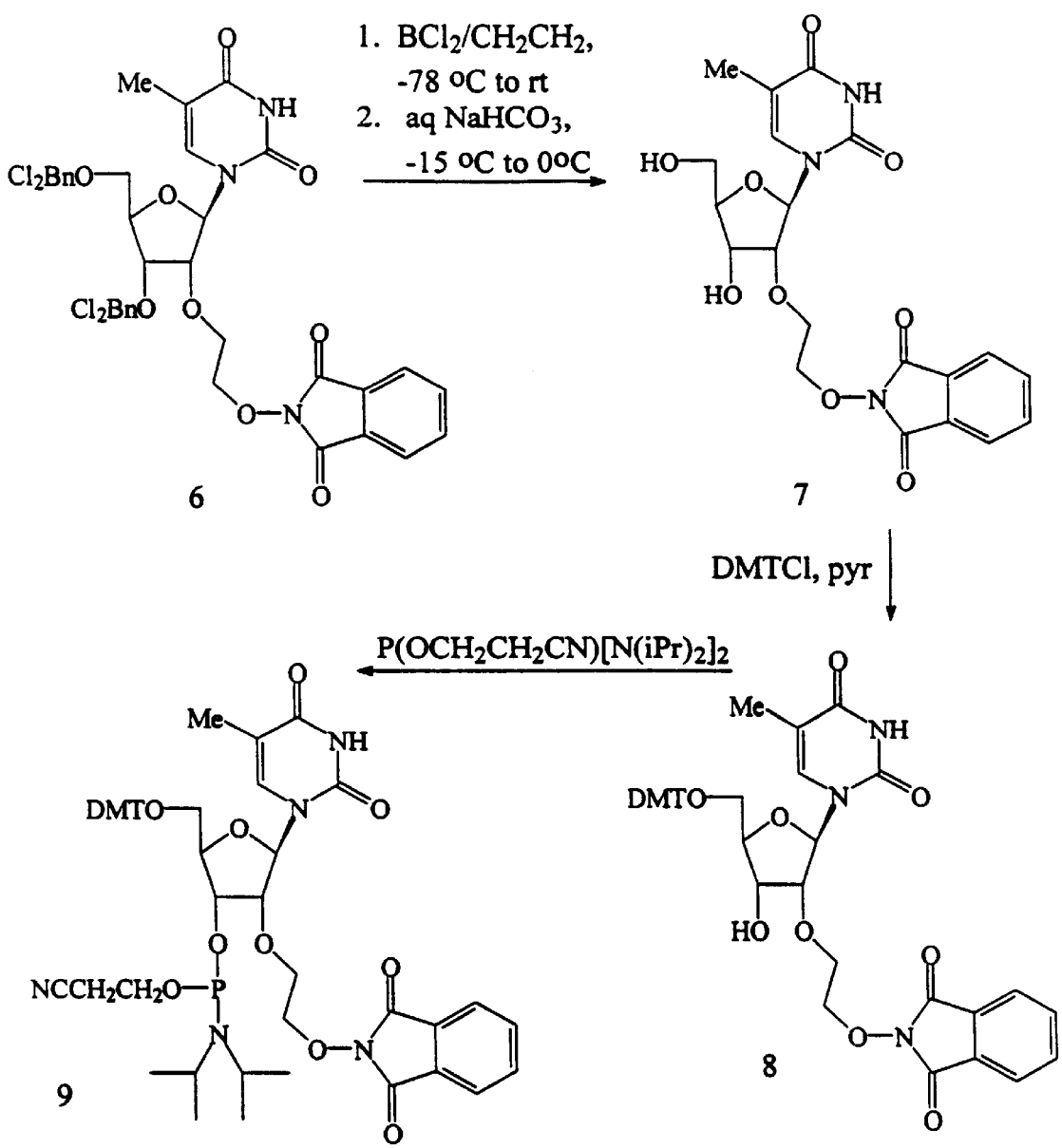
FIG. 2 shows a synthesis of 5-methyluridine DMT-phosphoramidate having a protected aminooxyethyl group at the 2'-O position.

1-[2'-O-(2-phthalimido-N-oxyethyl)-3',5'-bis-O-(2,4-dichlorobenzyl)-β-D-ribofuranosyl]thymine (7, FIG. 2)

Compound 6 (1.79 g, 2.34 mmol) was dissolved in CH$_2$Cl$_2$ (12 mL), the solution was cooled to −78° C. and 1.0 M boron trichloride (5.15 mL, 5.15 mmol) in CH$_2$Cl$_2$ was added and the reaction mixture was kept at 5° C. for 1.5 hours. Additional 1.0 M boron trichloride (5.15 mL, 5.15 mmol) in CH$_2$Cl$_2$ was added and the solution was stirred at 5° for an additional 1.5 hours. The pH was adjusted to 7 with saturated aqueous NaHCO$_3$ (30 mL). After dilution with CH$_2$Cl$_2$ (100 mL), the organic layer was separated, and the aqueous layer was extracted with CHCl$_3$ (5×25 mL) and then EtOAc (3×25 mL). The organic layers were combined, dried over Na$_2$SO$_4$, and evaporated in vacuo to give an oil. The oil was purified by flash chromatography using CH$_2$Cl$_2$-acetone, 45:55, to provide the title compound (7) as a white foam (619 mg, 59%). $^1$H NMR (CDCl$_3$): δ8.8 (br, 1H), 7.88–7.75 (m, 4H), 7.50 (s, 1H), 5.70 (d, J=4 Hz, 1H), 4.45–3.75 (m, 11H), 2.95 (br, 1H), 1.90 (s, 3H). $^{13}$C NMR (100 MHZ, CDCl$_3$): δ164.3, 163.7, 150.6, 137.4, 134.7, 128.5, 123.6, 110.5, 89.7, 84.7, 81.9, 77.6, 68.5, 68.4, 61.0, 12.3. LRMS (FAB+) m/z: 448 (M+H). LRMS (FAB−) m/z: 446 (M−H).

EXAMPLE 6

1-[2'-O-(2-phthalimido-N-oxyethyl)-5'-O-(4,41-dimethoxytrityl)-β-D-ribofuranosyl]thymine (8, FIG. 2)

Compound 7 was dried by coevaporation with anhydrous acetonitrile followed by further drying in vacuo (0.1 torr) at ambient temperature for 12 hours. The dried material (619 mg, 1.38 mmol) was dissolved in anhydrous pyridine (7 mL) and 4,4'-dimethoxytrityl chloride (514 mg, 1.52 mmol) was added. After 2 hours additional 4,4'-dimethoxytrityl chloride (257 mg, 0.76 mmol) was added. The solution was stirred for 2 hours and a final addition of 4,4'-dimethoxytrityl chloride (257 mg, 0.76 mmol) was made. After 12 h MeOH (10 mL) was added to the reaction mixture, it was stirred for 10 min and the solvent was evaporated in vacuo to give an oil which was coevaporated with toluene. The oil was purified by flash chromatography by pre-treating the silica with CH$_2$Cl$_2$-acetone-pyridine, 80:20:1, then using CH$_2$Cl$_2$-acetone, 80:20 to afford the title compound (8) as a yellow solid (704 mg, 68%). $^1$H NMR (CDCl$_3$): δ7.8–6.8 (m, 18H), 5.94 (d, J=2.2 Hz, 1H), 4.57–4.12 (m, 7H), 3.78 (s, 6H), 3.53 (m, 2H), 1.34 (s, 3H). $^{13}$C NMR (CDCl$_3$): δ164.3, 163.8, 158.6, 150.6, 144.4, 135.5, 135.4, 134.7, 130.1, 128.7, 128.2, 128.0, 127.1, 123.7, 113.3, 110.9, 87.9, 86.7, 83.2, 68.7, 68.5, 61.7, 55.2, 11.9. LRMS (FAB+) m/z: 750 (M+H). LRMS (FAB−) m/z: 748 (M−H). Anal. Calcd for $C_{41}H_{39}N_3O_{11} \cdot H_2O$: C, 65.14; H, 5.38; N, 5.47. Found: C, 63.85; H, 5.16; N, 5.14. Anal. Calcd for $C_{41}H_{39}N_3O_{11}$: C, 65.68; H, 5.24; N, 5.60. Found: C, 65.23; H, 5.27; N, 5.45.

EXAMPLE 7

1-[2'-O-(2-phthalimido-N-oxyethyl)-5'-O-(4,4'-dimethoxytrityl)-β-D-ribofuranosyl]thymine-3'-[(2-cyanoethyl)-N,N-diisopropylphosphoramidite] (9, FIG. 2)

Compound 8 was dried by coevaporation with anhydrous pyridine (2×20 mL), then further dried in vacuo (0.1 torr) at ambient temperature for 12 hours. The dried material (704 mg, 0.939 mmol) was dissolved in $CH_2Cl_2$ (9 mL), diisopropylamine tetrazolide (80.4 mg, 0.47 mmol) and 2-cyanoethyl-N,N,N',N'-tetraisopropylphosphorodiamidite (0.33 mL, 1.03 mmol) with stirring. After 2 hours at ambient temperature additional 2-cyanoethyl-N,N,N',N'-tetraisopropylphosphorodiamidite (0.33 mL, 1.03 mmol) was added and the solution was stirred for 20 hours. The solvent was evaporated in vacuo to give an oil which was purified by flash chromatography by pre-treating the silica with $CH_2Cl_2$-acetone-pyridine, 85:15:1, then using $CH_2Cl_2$-acetone, 85:15 to afford the title compound (9) as an oil (704 mg, 68%). The product was coevaporated with anhydrous acetonitrile (2×30 mL) and $CH_2Cl_2$ (2×30 mL) to afford a yellow foam. $^1$H NMR ($CDCl_3$): δ8.6 (br, 1H), 7.78–6.82 (m, 18H), 6.06 (m, 1H), 4.6–3.3 (m, 14H), 3.75 (s, 6H), 2.66 (m, 1H), 2.37 (m, 1H), 1.36 (s, 3H), 1.16 (m, 12H). $^{31}$P NMR ($CDCl_3$): δ150.5, 151.2. LRMS (FAB+) m/z: 950 (M+H). LRMS (FAB−) m/z: 948 (M−H). Anal. Calcd for $C_{50}H_{56}N_5O_{12}P·H_2O$: C, 62.04; H, 6.04; N, 7.24. Found: C, 62.20; H, 5.94; N, 7.34.

EXAMPLE 8

Figure 3:
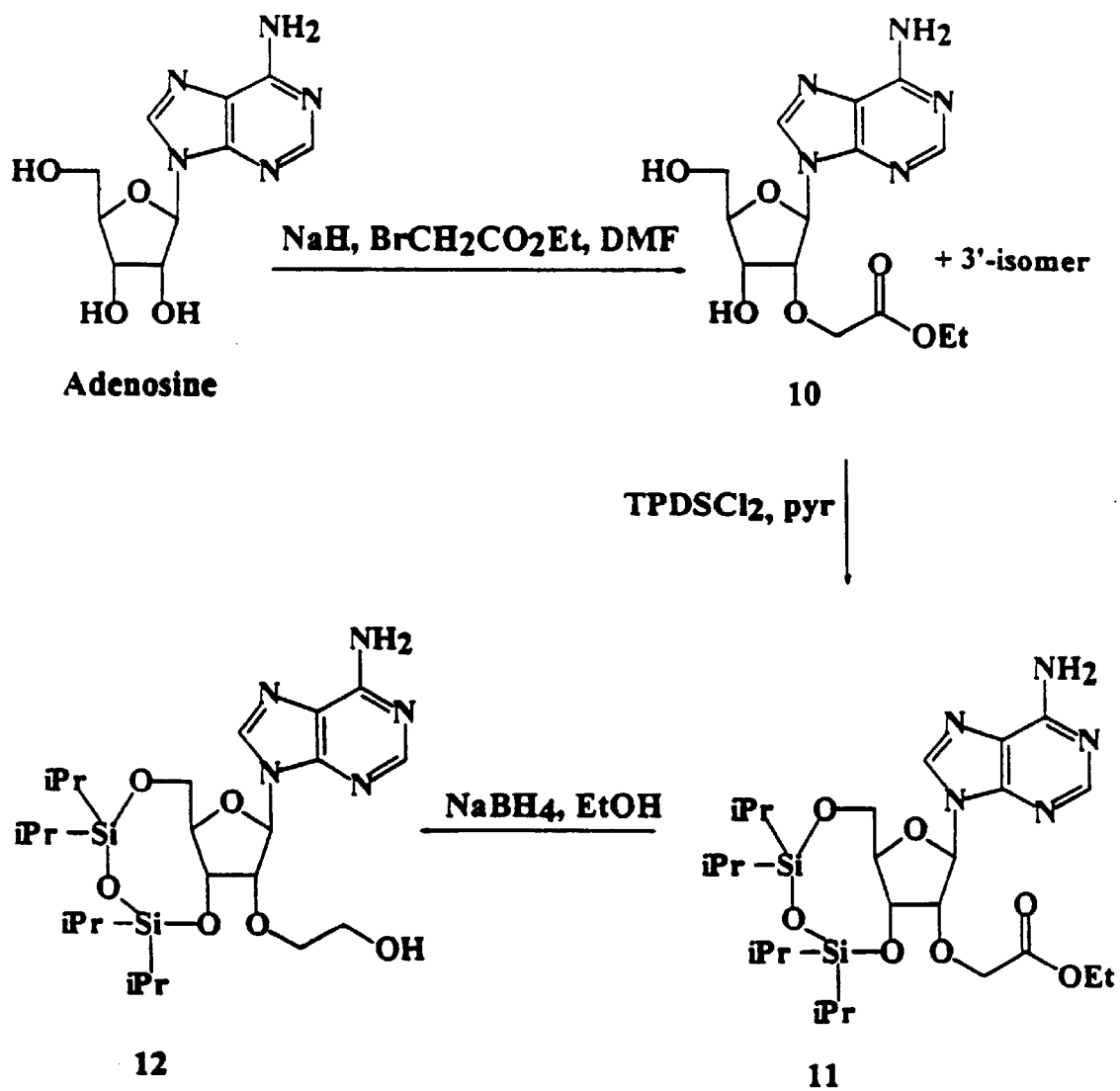
FIG. 3 shows a synthesis of certain intermediates of the invention.

2'-O-(2-ethylacetyl)-3',5'-O-(1,1,3,3-tetraisopropyldisiloxane-1,3-diyl)adenosine (11, FIG. 3)

Adenosine (30.00 g, 112 mmol) was dissolved in hot anhydrous DMF (600 mL) and the solution was cooled to ambient temperature. NaH (60% dispersion oil, 4.94 g, 124 mmol) was added and the mixture was stirred with a mechanical stirrer for 1 hour. The resulting suspension was cooled to 5° C. and ethylbromoacetate (13.7 mL, 124 mmol) was added. The resulting solution was stirred for 12 hours at ambient temperature and the solvent was evaporated in vacuo to give a residue which contained 2'-O-(2-ethylacetyl)adenosine (10) and the putative 3'-O-isomer. This material was coevaporated with pyridine to give a foam which was dissolved in anhydrous pyridine (400 mL). 1,3-Dichloro-1,1,3,3-tetraisopropyldisiloxane (39.52 mL, 124 mmol) was added and the solution was stirred for 24 hours at ambient temperature. The solvent was evaporated in vacuo to give an oil which was dissolved in EtOAc (500 mL) and washed with brine three times. The organic layer was separated, dried over $MgSO_4$, and the solvent was evaporated in vacuo to afford an oil. The oil was purified by flash chromatography using hexanes-EtOAc, 80:20, to give the title compound (11) as an oil (14.63 g, 22%). $^1$H NMR ($CDCl_3$): δ8.26 (s, 1H), 8.07 (s, 1H), 6.20 (br s, 2H), 4.91 (dd, $J_{1',2'}$=4.7 Hz, $J_{2',3'}$=9.3 Hz, 1H), 4.64–3.97 (m, 8H), 1.22 (t, 3H), 1.05 (m, 28 H). $^{13}$C NMR ($CDCl_3$): δ170.0, 155.5, 152.8, 149.0 139.3, 120.2, 88.6, 82.2, 81.1, 69.9, 68.3, 60.8, 60.0, 17.2, 14.0, 12.7. Anal. Calcd for $C_{26}H_{45}N_5O_7Si_2$: C, 52.41; H, 7.61; N, 11.75; Si, 9.43. Found: C, 52.23; H, 7.34; N, 11.69.

EXAMPLE 9

2'-O-(2-hydroxyethyl)-3',5'-O-(1,1,3,3-tetraisopropyldisiloxane-1,3-diyl)adenosine (12, FIG. 3)

Compound 11 (4.175 g, 7.01 mmol) was dissolved in ethanol (95%, 40 mL) and the resulting solution was cooled to 5° C. $NaBH_4$ (60% oil dispersion, 0.64 g, 16.8 mmol) was added, and the mixture was allowed to warm to ambient temperature. After stirring for 12 hours $CH_2Cl_2$ (200 mL) was added and the solution was washed with brine twice and the organic layer was separated. The organic layer was dried over $MgSO_4$, and the solvent was evaporated in vacuo to give an oil. The oil was purified by flash chromatography using EtOAc-MeOH, 95:5, to afford the title compound (12) as an oil (0.368 g, 9.5%). $^1$H NMR ($CDCl_3$): δ8.31 (s, 1H), 8.14 (s, 1H), 6.18 (br s, 2H), 6.07 (s, 1H), 4.62 (dd, $J_{1',2'}$=4.6 Hz, $J_{2',3'}$=9.4 Hz, 1H), 4.3–3.5 (m, 8H), 1.03 (m, 28H). $^{13}$C NMR ($CDCl_3$): δ155.5, 153.0, 148.7, 138.3, 120.3, 89.2, 82.7, 81.4, 73.5, 69.3, 61.8, 59.7, 17.2, 17.0, 16.8, 13.4, 12.9, 12.8, 12.6. LRMS (FAB+) m/z: 554 (M+H), 686 (M+Cs+).

EXAMPLE 10

Figure 4:
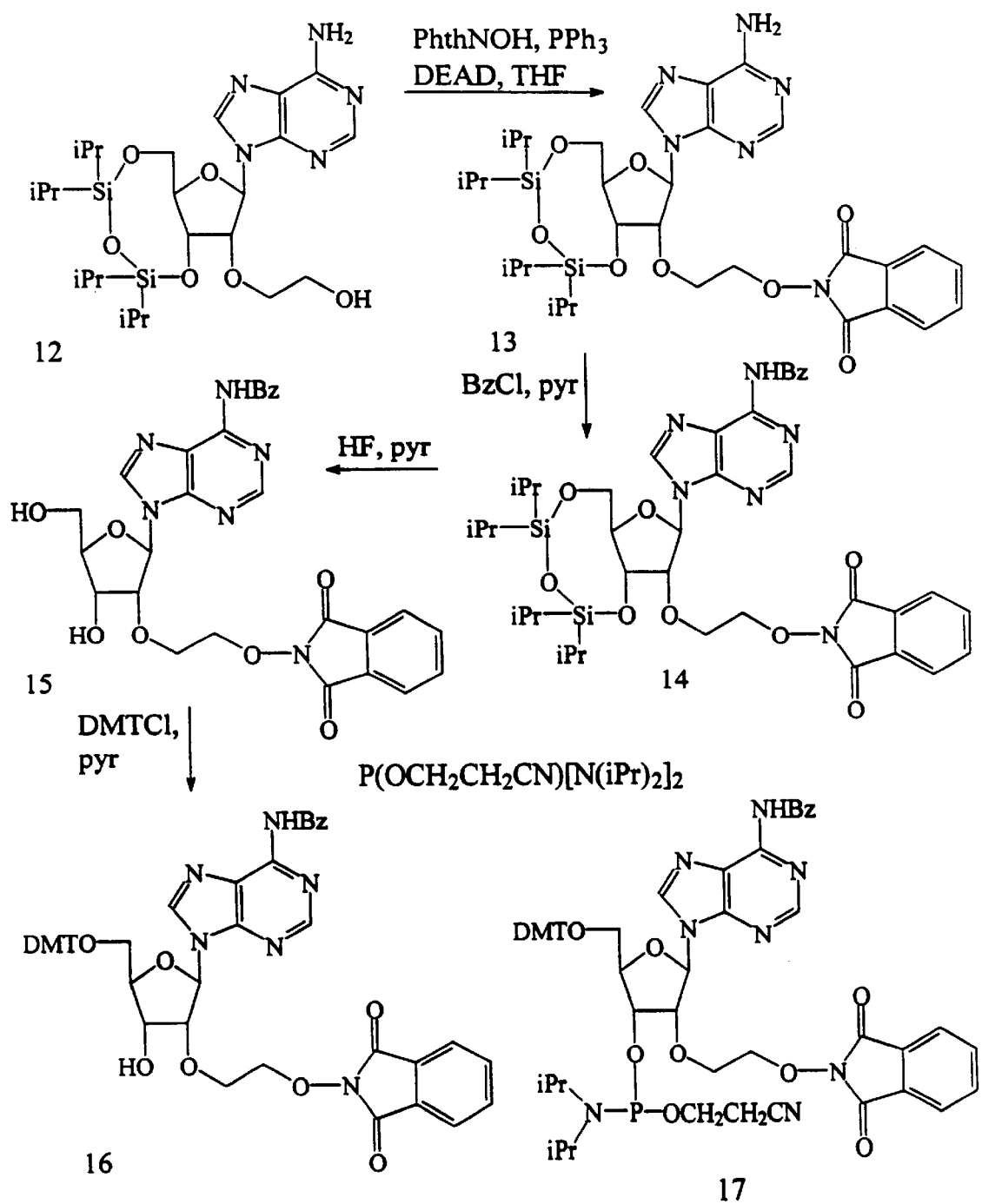
FIG. 4 shows a synthesis of adenosine DMT-phosphoramidate having a protected aminooxyethoxy group at the 2' position.

2'-O-(2-Phthalimido-N-hydroxyethyl)-3',5'-O-(1,1,3,3-tetraisopropyldisiloxane-1,3-diyl)adenosine (13, FIG. 4)

To a solution of compound 12 (0.330 g, 0.596 mmol) in anhydrous THF (10 mL) was added triphenylphosphine (0.180 g, 0.685 mmol) and N-hydroxyphthalimide (0.112 g, 0.685 mmol). To this mixture diethyl azodicarboxylate (0.11 mL, 685 mmol) was added dropwise at 5° C. After stirring for 3 hours at ambient temperature, the solvent was evaporated to give an oil. The oil was dissolved in EtOAc and washed with saturated aqueous $NaHCO_3$ (×3) and brine. The organic layer was separated, dried over $MgSO_4$. The solvent was evaporated in vacuo to give an oil. The oil was purified by flash chromatography using EtOAc-MeOH, 95:5, to give the title compound (13) as an oil (0.285 g, 68%). $^1$H NMR ($CDCl_3$): δ8.21 (s, 1H), 8.05 (s, 1H), 7.8–7.45 (m, 4H), 6.00 (s, 1H), 5.88 (br s, 2H), 4.92 (dd, $J_{1',2'}$=4.6, $J_{2',3'}$=9.0 Hz), 4.5–3.9 (m, 8H), 1.0 (m, 28H). $^{13}$C NMR ($CDCl_3$): δ163, 155.3, 152.8, 149, 139.6, 134.3, 123.4, 120, 88.7, 82.7, 81.1, 77.4, 70.2, 69.5, 60.1, 17.4, 17.2, 17.0, 16.9, 13.3, 12.9, 12.7, 12.6. LRMS (FAB+) m/z: 699 (M+H).

EXAMPLE 11

N6-Benzoyl-2'-O-(2-phthalimido-N-hydroxyethyl)-3',5'-O-(1,1,3,3-tetraisopropyldisiloxane-1,3-diyl)adenosine (14, FIG. 4)

To a solution of compound 13 (1.09 g, 1.97 mmol) in anhydrous pyridine (19 mL) cooled to 5° C. was added benzoyl chloride (1.14 mL, 9.8 mmol) and the resulting mixture was stirred at ambient temperature for 12 hours. After cooling the mixture to 5° C., cold water (3.8 mL) was added, the mixture was stirred for 15 minutes, and conc $NH_4OH$ (3.8 mL) was added. After stirring for 30 minutes at 5° C. the solvent was evaporated to give a residue which was dissolved in water and extracted with $CH_2Cl_2$ three times. The organic extracts were combined, dried over $MgSO_4$, and evaporated in vacuo to afford an oil. The oil was purified by flash chromatography using hexanes-EtOAc, 50:50, then 20:80, to give the title compound (14) as an oil (0.618 g, 48%). $^1$H NMR ($CDCl_3$): δ9.2 (br s, 1H), 8.69 (s, 1H), 8.27 (s, 1H), 8.0–7.4 (m, 9H), 6.12 (s, 1H), 4.95 (dd, $J_{1',2'}$=4.7 Hz, $J_{2',3'}$9.1 Hz, 1H), 4.5–4.0 (m, 8H), 1.06 (m, 28H). $^3$C NMR ($CDCl_3$): δ164.4, 163.3, 152.5, 150.8, 149.3, 142.1, 134.4, 133.7, 132.6, 132.1, 128.7, 128.2, 127.7, 123.4, 88.9, 82.7, 81.3, 77.5, 70.1, 69.6, 60.0, 17.2, 17.0, 16.8, 13.3, 12.8, 12.7, 12.6. LRMS (FAB+) m/z: 803 (M+H).

EXAMPLE 12

$N^6$-Benzoyl-2'-O-(2-phthalimido-N-hydroxyethyl)adenosine (15, FIG. 4)

To a solution of compound 14 (0.680 g, 0.847 mmol) in THF (20 mL) in a polyethylene reaction vessel at 5° C. was added HF-pyridine (70%, 0.48 mL, 16.9 mmol) and the resulting mixture was warmed to ambient temperature. After stirring for 12 hours the solvent was evaporated in vacuo, EtOAc was added, the solution was washed with water, and the aqueous layer was separated and extracted with EtOAc. The organic layers were combined, dried over MgSO$_4$, and the solvent was evaporated in vacuo to give the title compound (15) as a solid (408 mg, 86%). $^1$H NMR (DMSO-d$_6$): δ11.2 (br s, 1H), 8.71 (s, 1H), 8.67 (s, 1H), 8.0–7.5 (m, 9H), 6.11 (d, J 1',2'=5.7 Hz), 5.23 (d, 1H), 5.14 (t, 1H), 4.66 (t, 1H), 4.35 (m, 3H), 3.90 (m, 3H), 3.6 (m, 2H). $^{13}$C NMR (DMSO-d$_6$): δ163.5, 152.0, 143.2, 135.0, 132.6, 131.9, 131.7, 129.3, 128.7, 128.5, 123.4, 86.3, 85.8, 81.3, 76.8, 69.0, 68.7, 61.3. LRMS (FAB+) m/z: 561 (M+H, 583 (M+Na+).

EXAMPLE 13

N$^6$-Benzoyl-2'-O-(2-phthalimido-N-oxyethyl)-5'-O-(4,4'-dimethoxytrityl)adenosine (16, FIG. 4)

To a solution of compound 15 (0.258 g, 0.46 mmol) in anhydrous pyridine (5 mL) was added 4,4'-dimethoxytrityl chloride (0.179 g, 0.53 mmol) and the solution was stirred for 12 hours at ambient temperature. Water was added and the mixture was extracted with EtOAc three times. The organic extracts were combined, evaporated in vacuo, and dried over MgSO$_4$. The resulting oil was purified by flash chromatography using hexanes-EtOAc, 90:10, to give the title compound (16) as an oil (0.249 g, 63%). $^1$H NMR (CDCl$_3$): δ9.16 (br s, 1H), 8.68 (s, 1H), 8.28 (s, 1H), 8.1–6.8 (m, 22H), 6.26 (d, J 1',2'=4.0 Hz, 1H), 4.76 (m, 1H), 4.60 (m, 1H), 4.4–4.3 (m, 3H), 4.13–4.0 (m, 3H), 3.77 (s, 6H), 3.48 (m, 2H). $^{13}$C NMR (CDCl$_3$): δ164.5, 163.6, 158.5, 152.6, 151.4, 149.5, 144.5, 141.9, 135.7, 134.7, 132.7. 130.1, 128.8, 128.2, 127.8, 126.9, 123.7, 113.2, 87.2, 84.1, 82.6, 69.9, 69.0, 63.0, 60.3, 55.2. HRMS (FAB+) m/z (M+Cs+) calcd for C$_{48}$H$_{42}$N$_6$O$_{10}$ 995.2017, found 995.2053 (M+Cs+).

EXAMPLE 14

N$^6$-Benzoyl-2'-O-(2-phthalimido-N-oxyethyl)-5'-O-(4,4'-dimethoxytrityl)adenosine-3'-[(2-cyanoethyl)-N,N-diisopropylphosphoramidite] (17, FIG. 4)

To a solution of compound 16 (0.300 g, 0.348 mmol) in CH$_2$Cl$_2$ (10 mL) was added diisopropylamine tetrazolide (0.030 g, 0.174 mmol) and 2-cyanoethyl-N,N,N',N'-tetraisopropylphosphorodiamidite (0.13 mL, 0.418 mmol). After stirring for 12 hours at ambient temperature additional diisopropylamine tetrazolide (0.060 g, 0.348 mmol) and 2-cyanoethyl-N,N,N',N'-tetraisopropylphosphorodiamidite (0.26 mL, 0.832 mmol) were added in two portions over 24 hours. After 24 hours CH$_2$Cl$_2$-NEt$_3$, 100:1, was added and the mixture was washed with saturated aqueous NaHCO$_3$ and brine. The organic layer was separated, dried over MgSO$_4$, and the solvent was evaporated in vacuo. The resulting oil was purified by flash chromatography by pretreating the silica with hexanes-EtOAc-NEt$_3$, (40:60:1), then using the same solvent system to give the title compound (17) as an oil (203 g, 55%). $^1$H NMR (CDCl$_3$): δ6.27 (m, 1H). $^{31}$P NMR (CDCl$_3$): δ151.0, 150.5. HRMS (FAB+) m/z (M+Cs+) calcd for C$_{57}$H$_{59}$N$_8$O$_{11}$P 1195.3095, found 1195.3046 (M+Cs+).

EXAMPLE 15

Figure 5:
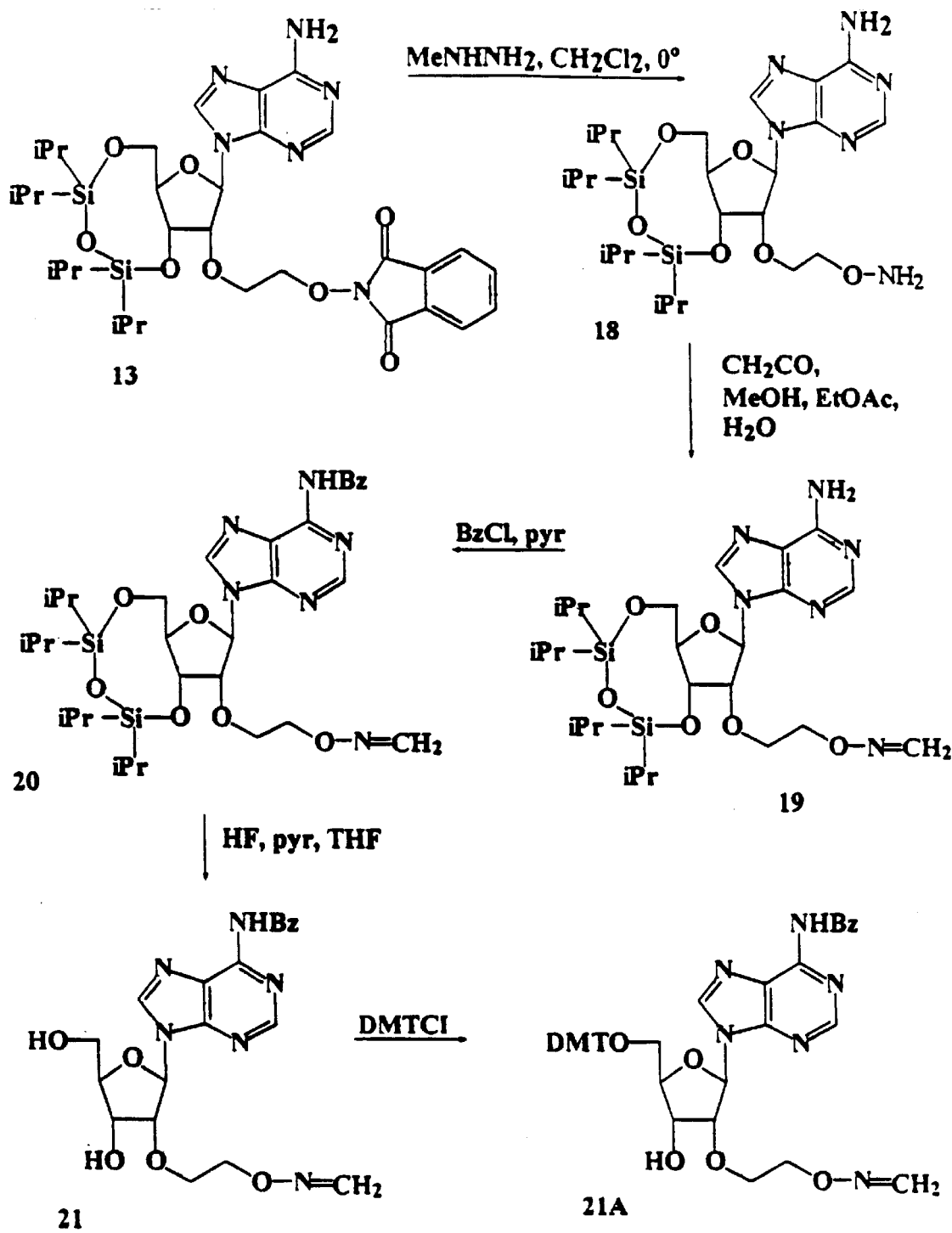
FIG. 5 shows a synthesis of certain intermediates of the invention.

2'-O-(2-aminooxyethyl)-3',5'-O-(1,1,3,3-tetraisopropyldisiloxane-1,3-diyl)adenosine (18, FIG. 5)

To a solution of compound 13 (0.228 g, 0.326 mmol) in CH$_2$Cl$_2$ (5 mL) at 5° C. was added methylhydrazine (0.017 mL, 0.326 mmol) with stirring for 2 hours. The mixture was filtered to remove a precipitate and the filtrate was washed with water and brine. The organic layer was separated, dried over MgSO$_4$, and the evaporated in vacuo to give the title compound (18) as an oil (186 mg). The oil was of sufficient purity for subsequent reactions. $^1$H NMR (CDCl$_3$): δ8.31 (s, 1H), 8.15 (s, 1H), 6.07 (s, 1H), 5.78 (br s, 2H), 4.70 (dd, J 1',2'=4.4 Hz, J 2',3'=9.0 Hz, 1H), 4.3–3.9 (m, 8H), 1.9 (br, 2H), 1.0 (m, 28H). LRMS (FAB+) m/z: 569 (M+H), 702 (M+Cs+).

EXAMPLE 16

2'-O-(2-O-Formaldoximylethyl)-3',5'-O-(1,1,3,3-tetraisopropyldisiloxane-1,3-diyl)adenosine (19, FIG. 5)

To a solution of compound 18 (0.186 g, 0.326 mmol) in EtOAc (2 mL) and MeOH (2 mL) was added formaldehyde (aqueous 37%, 0.028 mL, 0.342 mmol) with stirring at ambient temperature for 3 hours. The solvent was evaporated in vacuo to give the title compound (19) as an oil (189 mg). The oil was of sufficient purity for subsequent reactions. $^1$H NMR (CDCl$_3$): δ8.31 (s, 1H), 8.09 (s, 1H), 6.97 (d, J=8.3 Hz, 1H), 6.38 (d, J=8.3 Hz, 1H), 6.01 (s, 1H), 5.66 (br s, 2H), 4.77 (dd, J$_{1',2'}$=4.7 Hz, J$_{2',3'}$=9.3 Hz), 4.3–4.0 (m, 8H), 1.0 (m, 28H). LRMS (FAB+) m/z: 581 (M+H), 713 (M+Cs+).

EXAMPLE 17

N$^6$-Benzoyl-2'-O-(2-O-formaldoximylethyl)-3',5'-O-(1,1,3,3-tetraisopropyldisiloxane-1,3-diyl)adenosine (20, FIG. 5)

To a solution of compound 19 (0.189 g, 0.326 mmol) in pyridine (5 mL) at 5° C. was added benzoyl chloride (0.19 mL, 1.63 mmol) and the resulting solution was stirred at ambient temperature for 3 hours. The solution was cooled to 5° C. and concentrated NH$_4$OH (1.5 mL) was added with stirring for 1 hour. The solvent was evaporated in vacuo to give an oil which was dissolved in CH$_2$Cl$_2$. The solution was washed with water and the organic layer was separated, dried with MgSO$_4$, and the solvent was evaporated to give the title compound (20) (223 mg) as an oil which was of sufficient purity for subsequent reactions. $^1$H NMR (CDCl$_3$): δ9.30 (br, 1H), 8.79 (s, 1H), 8.31 (s, 1H), 8.1–7.2 (m, 5H), 7.00 (d, 1H), 6.39 (d, 1H), 6.09 (s, 1H), 4.77 (dd, 1H), 4.4–3.9 (m, 8H), 1.1 (m, 28H).

EXAMPLE 18

N$^6$-Benzoyl-2'-O-(2-O-formaldoxinylethyl) adenosine (21, FIG. 5)

To a solution of compound 20 (223 mg, 0.326 mmol) in THF (10 mL) in a polyethylene reaction vessel at 5° C. was added HF-pyridine (70%, 0.19 mL, 6.5 mmol) and the mixture was allowed to warm to ambient temperature. After stirring for 48 hours the solvents were evaporated in vacuo to give a residue which was dissolved in EtOAc and washed with water. The organic layer was separated, the aqueous layer was extracted with EtOAc, and the organic layers were combined, dried over MgSO$_4$, and evaporated in vacuo. The resulting residue was purified by flash chromatography using EtOAc-MeOH, 95:5, to give the title compound (21) as a solid (24 mg, 17% from 13). $^1$H NMR (CDCl$_3$): δ9.05 (br s, 1H), 8.77 (s, 1H), 8.13 (s, 1H), 7.9–7.2 (m), 6.26 (d, J=10.7 Hz, 1H), 6.03 (d, J$_{1',2'}$=7.8 Hz), 4.88 (dd, J=4.6 Hz, J=7.9 Hz, 1H), 4.6–3.7 (m, 10H). LRMS (FAB+) m/z: 443 (M+H). LRMS (FAB−) m/z: 441 (M−H).

EXAMPLE 19

N6-Benzoyl-2'-O-(2-O-formaldoximylethyl)-5'-O-(4,4'-dimethoxytrityl)adenosine (21A, FIG. 5)

To a solution of compound 21 (0.34 g, 0.768 mmol) in pyridine (7 mL) was added 4,4'-dimethoxytrityl chloride (0.312 g, 0.922 mmol) and the reaction mixture was stirred at ambient temperature for 5 hours. Additional amounts of 4,4'-dimethoxytrityl chloride (520 mg, 1.54 mmol and 340 mg, 0.768 mmol) were added over 24 hours. The solvent was evaporated, the crude product was dissolved in EtOAc, and washed with water. The organic layer was separated, dried over $MgSO_4$ and the solvent was evaporated in vacuo. The crude material was purified by column chromatography using EtOAc-Hexanes-$NEt_3$, 80:20:0.5, v/v/v, followed by, EtOAc-NEt3, 100:0.5, v/v, as solvent to give the title compound (21A) as an oil (0.269 g, 47%). $^1$H NMR ($CDCl_3$): $\delta$8.99 (br s, 1H), 8.74 (s, 1H), 8.1–6.8 (m, 18H), 7.00 (d, 1H), 6.43 (d, 1H), 6.19 (d, 1H), 4.72 (m, 1H), 4.48 (m, 1H), 4.23 (m, 3H), 4.1 (m, 1H), 3.9 (m, 1H), 3.78 (s, 6H), 3.45 (m, 2H), 3.15 (d, 1H). HRMS (FAB+) m/z (M+Cs+) calcd for $C_{41}H_{40}N_6O_8$ 877.1962, found 877.1988 (M+Cs+).

EXAMPLE 20

2'-O-Allyl-5'-O-dimethoxytrityl-5-methyluridine

In a 100 mL stainless steel pressure reactor, allyl alcohol (20 mL) was slowly added to a solution of borane in tetrahydrofuran (1 M, 10 mL, 10 mmol) with stirring. Hydrogen gas rapidly evolved. Once the rate of bubbling subsided, 2,2'-anhydro-5-methyluridine (1.0 g, 0.4.2 mmol) and sodium bicarbonate (6 mg) were added and the reactor was sealed. The reactor was placed in an oil bath and heated to 170° C. internal temperature for 18 hours. The reactor was cooled to room temperature and opened. Tlc revealed that all the starting material was gone (starting material and product Rf 0.25 and 0.60 respectively in 4:1 ethyl acetate/methanol on silica gel). The crude solution was concentrated, coevaporated with methanol (50 mL), boiling water (15 mL), absolute ethanol (2×25 mL) and then the residue was dried to 1.4 g of tan foam (1 mm Hg, 25° C., 2 hours). A portion of the crude nucleoside (1.2 g) was used for the next reaction step without further purification. The residue was coevaporated with pyridine (30 mL) and redissolved in pyridine (30 mL). Dimethoxytrityl chloride (1.7 g, 5.0 mmol) was added in one portion at room temperature. After 2 hours the reaction was quenched with methanol (5 mL), concentrated in vacuo and partitioned between a solution of saturated sodium bicarbonate and ethyl acetate (150 mL each). The organic phase was separated, concentrated and the residue was subjected to column chromatography (45 g silica gel) using a solvent gradient of hexanes-ethyl acetate-triethylamine (50:49:1) to (60:39:1). The product containing fractions were combined, concentrated, coevaporated with acetonitrile (30 mL) and dried (1 mm hg , 25° C., 24 hours) to 840 mg (34% two-step yield) of white foam solid. The NMR was consistent with the unmethylated uridine analog reported in the literature.

EXAMPLE 21

2'-O-(2-hydroxyethyl)-5'-O-dimethoxytrityl-5-methyluridine

2'-O-Allyl-5'-O-dimethoxytrityl-5-methyluridine (1.0 g, 1.6 mmol), aqueous osmium tetroxide (0.15 M, 0.36 mL, 0.0056 mmol, 0.035 eq) arid 4-methylmorpholine N-oxide (0.41 g, 3.5 mmol, 2.15 eq) were dissolved in dioxane (20 mL) and stirred at 25° C. for 4 hours. Tlc indicated complete and clean reaction to the diol (Rf of starting to diol 0.40 to 0.15 in dichloromethane/methanol 97:3 on silica). Potassium periodate (0.81 g, 3.56 mmol, 2.2 eq) was dissolved in water (10 mL) and added to the reaction. After 17 hours the tlc indicated a 90% complete reaction (aldehyde Rf 0.35 in system noted above). The reaction solution was filtered, quenched with 5% aqueous sodium bisulfite (200 mL) and the product aldehyde was extracted with ethyl acetate (2×200 mL). The organic layers were combined, washed with brine (2×100 mL) and concentrated to an oil. The oil was dissolved in absolute ethanol (15 mL) and sodium borohydride (1 g) was added. After 2 hours at 25° C. the tlc indicated a complete reaction. Water (5 mL) was added to destroy the borohydride. After 2 hours the reaction was stripped and the residue was partitioned between ethyl acetate and saturated sodium bicarbonate solution (50 mL each). The organic layer was concentrated in vacuo and the residue was columned (silica gel 30 g, dichloromethane-methanol 97:3). The product containing fractions were combined and stripped and dried to 0.50 g (50%) of white foam. The NMR was consistent with that of material prepared by the glycosylation route.

EXAMPLE 22

2'-O-(2-hydroxyethyl)-5-methyluridine

In a 100 mL stainless steel pressure reactor, ethylene glycol (20 mL) was slowly added to a solution of borane in tetrahydrofuran (1 M, 10 mL, 10 mmol) with stirring. Hydrogen gas rapidly evolved. Once the rate of bubbling subsided, 2,2'-anhydro-5-methyluridine (1.0 g, 0.4.2 mmol) and sodium bicarbonate (3 mg) were added and the reactor was sealed. The reactor was placed in an oil bath and heated to 150° C. internal temperature for 72 hours. The bomb was cooled to room temperature and opened. TLC revealed that 65% of the starting material was gone (starting material and product Rf 0.25 and 0.40 respectively in 4:1 ethyl acetate/methanol on silica gel). The reaction was worked up incomplete. The crude solution was concentrated (1 mm Hg at 100° C., coevaporated with methanol (50 mL), boiling water (15 mL) and absolute ethanol (2×25 mL) and the residue was dried to 1.3 g of off-white foam (1 mm Hg, 25° C., 2 hours). NMR of the crude product was consistent with 65% desired product and 35% starting material. The TLC Rf matched (on cospot) the same product generated by treating the DMT derivative above with dilute hydrochloric acid in methanol as well as the Rf of one of the spots generated by treating a sample of this product with dimethoxytrityl chloride matched the known DMT derivative (other spots were DMT on side chain and bis substituted product).

EXAMPLE 23

Figure 6:
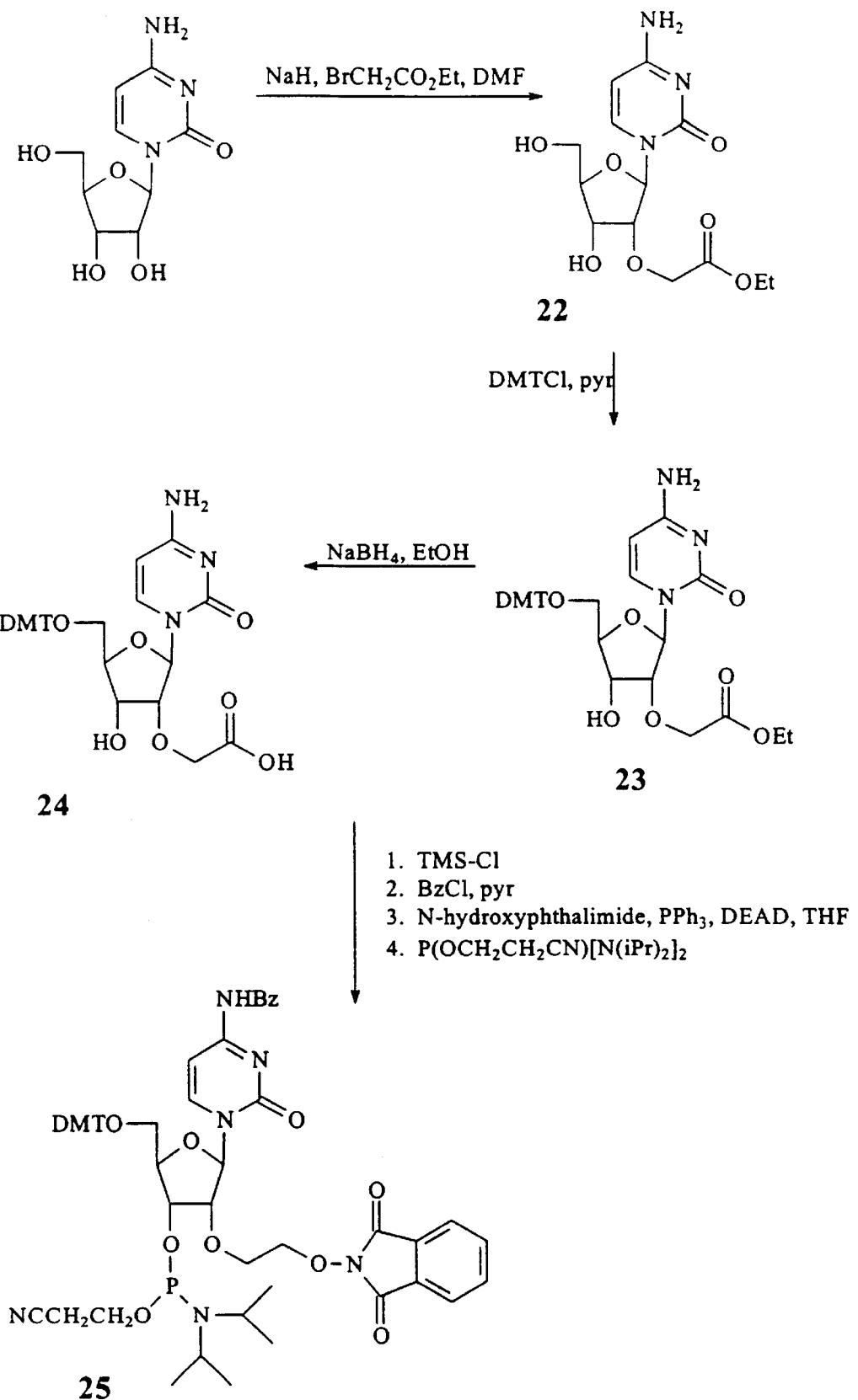
FIG. 6 shows a synthesis of cytidine DMT-phosphoramidate having a protected aminooxyethoxy group at the 2' position.
Figure 7:
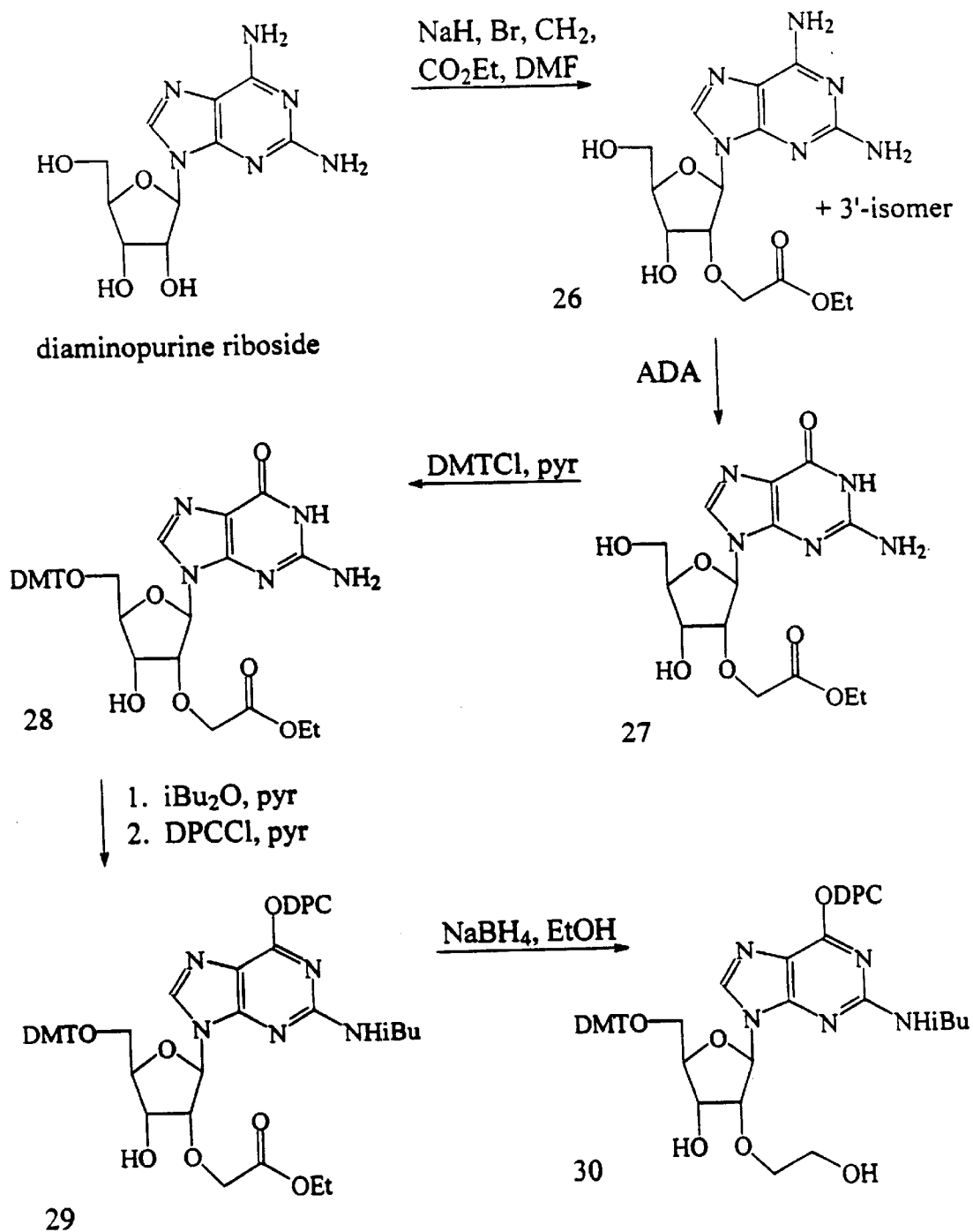
FIG. 7 shows a synthesis of certain intermediates of the invention.
Figure 8:
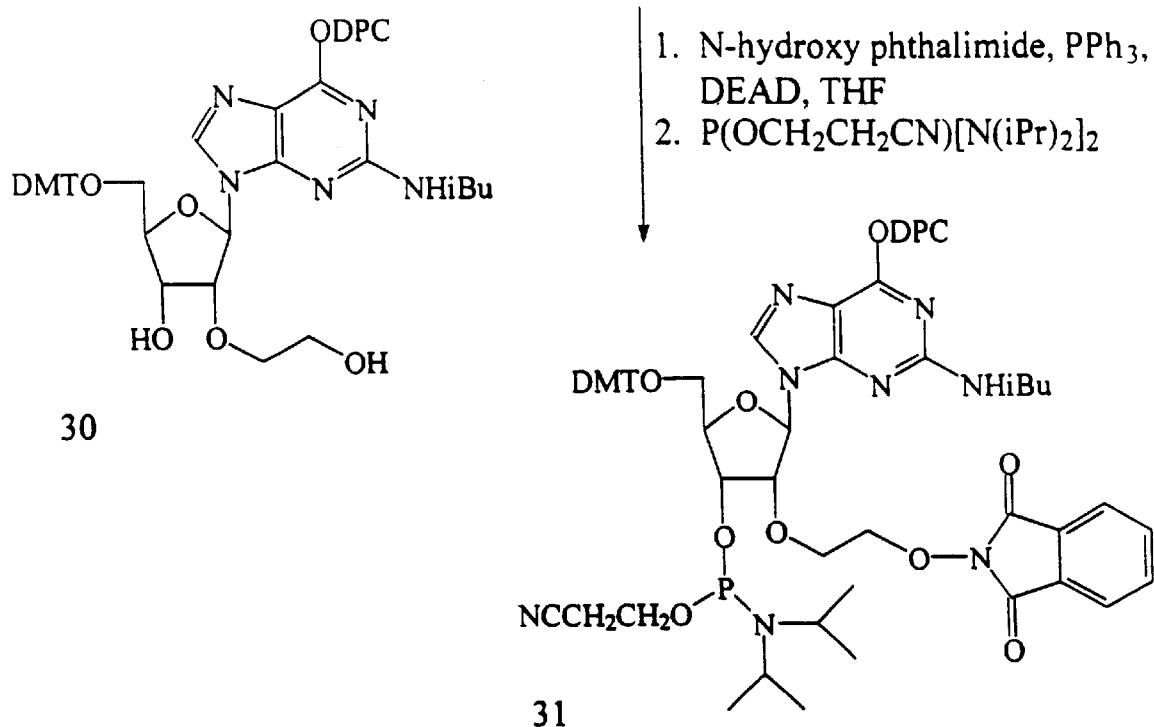
FIG. 8 shows a synthesis of guanidine DMT-phosphoramidate having a protected aminooxyethoxy group at the 2' position.

N4-benzoyl-2'-O-(2-phthalimido-N-oxyethyl)-5'-O-(4,4'-dimethoxytrityl)cytidine-3'-[(2-cyanoethyl)-N,N-diisopropylphosphoramidite] (25, FIG. 6)

The 2'-O-aminooxyethyl cytidine and guanosine analogs may be prepared via similar chemistry in combination with reported literature procedures. Key to the synthetic routes is the selective 2'-O-alkylation of unprotected nucleosides. (Guinosso, C. J., Hoke, G. D., Frier, S., Martin, J. F., Ecker, D. J., Mirabelli, C. K., Crooke, S. T., Cook, P. D., *Nucleosides Nucleotides,* 1991, 10, 259; Manoharan, M., Guinosso, C. J., Cook, P. D., *Tetrahedron Lett.,* 1991, 32, 7171; Izatt, R. M., Hansen, L. D., Rytting, J. H., Christensen, J. J., *J. Am. Chem. Soc.*, 1965, 87, 2760. Christensen, L. F., Broom, A. D., *J. Org. Chem.*, 1972, 37, 3398. Yano, J., Kan, L. S., Ts'o, P. O. P., *Biochim. Biophys. Acta,* 1980, 629, 178; Takaku, H., Kamaike, K., *Chemistry Lett.* 1982, 189). Thus, cytidine may be selectively alkylated to afford the intermediate 2'-O-(2-ethylacetyl)cytidine 22. The 3'-isomer of 22 is typically present in a minor amount and can be resolved by chromatography or crystallization. Compound 22 can be protected to give 2'-O-(2-ethylacetyl)-5'-O-(4,4'-dimethoxytrityl)cytidine (23). Reduction of the ester 23 should yield 2'-O-(2-hydroxyethyl)-5'-O-(4,4'-dimethoxytrityl)cytidine (24) which can be N-4-benzoylated, the primary hydroxyl group may be displaced by N-hydroxyphthalimide via a Mitsunobu reaction, and the protected nucleoside may be phosphitylated as usual to yield N4-benzoyl-2'-O-(2-phthalimido-N-oxyethyl)-5'-O-(4,4'-dimethoxytrityl)cytidine-3'-[(2-cyanoethyl)-N,N-diisopropylphosphoramidite] (25).

EXAMPLE 24

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite] (31)

In a similar fashion the 2'-O-aminooxyethyl guanosine analog may be obtained by selective 2'-O-alkylation of diaminopurine riboside (multigram quantities of diaminopurine riboside may be purchased from Schering AG (Berlin) to provide 2'-O-(2-ethylacetyl)diaminopurine riboside 26 along with a minor amount of the 3'-O-isomer. Compound 26 may be resolved and converted to 2'-O-(2-ethylacetyl) guanosine 27 by treatment with adenosine deaminase. (McGee, D. P. C., Cook, P. D., Guinosso, C. J., PCT Int. Appl., 85 pp.; PIXXD2; WO 94/02501 A1 940203.) Standard protection procedures should afford 2'-O-(2-ethylacetyl)-5'-O-(4,4'-dimethoxytrityl)guanosine 28 and 2N-isobutyryl-6-O-diphenylcarbamoyl-2'-O-(2-ethylacetyl)-5'-O-(4,4'-dimethoxytrityl)guanosine 29 which may be reduced to provide 2-N-isobutyryl-6-O-diphenylcarbamoyl-2'-O-(2-ethylacetyl)-5'-O-(4,4'-dimethoxytrityl)guanosine (30). As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite] (31).

EXAMPLE 25

Figure 9:
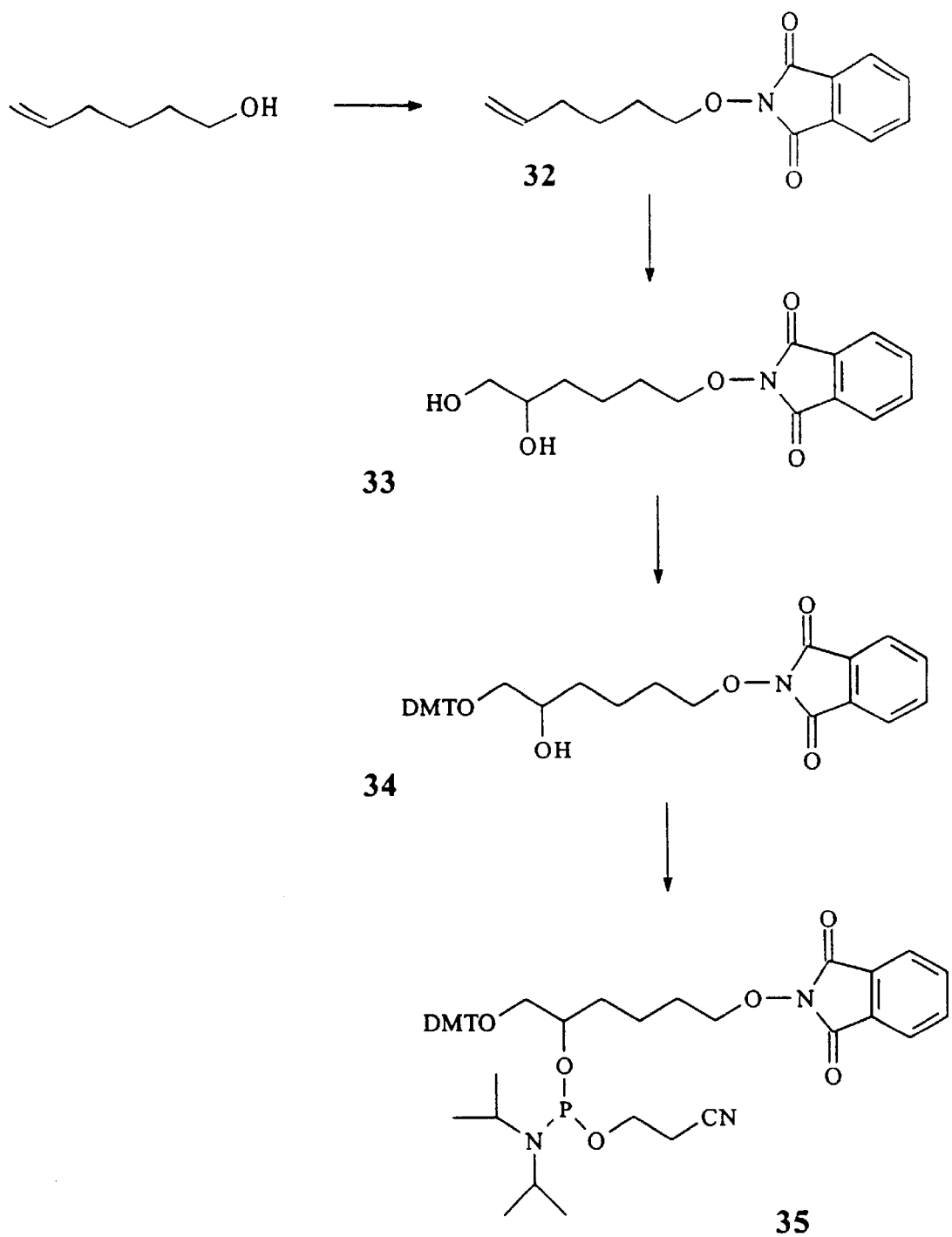
FIG. 9 shows a synthesis of some intermediates and monomers of the invention.

-(1-hydroxyphthalimido)-5-hexene (32, FIG. 9)

To a stirred solution of 5-hexane-1-ol (20 g, 0.2 mol) in THF (500 mL) was added triphenylphosphine (80 g, 0.3 mol) and N-hydroxyphthalimide (49 g, 0.3 mol). The mixture was cooled to 0° C. and diethylazido carboxylate (48 mL, 0.3 mol) was added slowly over a period of 1 hour. The reaction mixture was allowed to warm to room temperature and the yellow solution was stirred overnight. The solvent was then evaporated to give a yellow oil. The oil was dissolved in $CH_2Cl_2$ and washed with water, saturated $NaHCO_3$ solution followed by a saturated NaCl solution. The organic layer was concentrated in vacuo and the resulting oil was dissolved in a solution of $CH_2Cl_2$/ether to crystallize out $Ph_3P$=O as much as possible. After three steps of purification the title compound was isolated as a yellow waxy solid (yield 93%). $^{13}C$ NMR: δ21.94, 24.83, 27.58, 33.26,. 78.26, 114.91, 123.41, 128.40, 128.54, 128.63, 134.45 and 163.8 ppm.

EXAMPLE 26

N-(1-hydroxyphthalimido-5,6-hexane-diol) (33, FIG. 9)

Compound 32 (2.59 g, 10 mmol), aqueous osmium tetroxide (0.15 M, 3.6 mL, 0.056 mmol) and N-methylmorpholine-N-oxide (2.46 g, 21 mmol) were dissolved in THF (100 mL). The reaction mixture was covered with aluminum foil and stirred at 25° C. for 4 hours. Tlc indicated the diol was formed. The solvent was evaporated and the residue was partitioned between water and $CH_2Cl_2$. The organic layer was washed with a saturated solution of NaCl and dried over anhydrous $MgSO_4$. Concentration of the organic layer resulted in a brownish oil that was characterized by $^{13}C$ NMR and used in the next step without further purification. $^{13}C$ NMR: δ21.92, 28.08, 32.62, 66.76, 71.96, 78.33, 123.43, 128.47, 128.71, 131.93, 132.13, 134.49, 163.89.

EXAMPLE 27

N-1-hydroxy phthalimido-6-O-dimethyoxytrityl-5,6 hexane-diol (34, FIG. 9)

The product from the previous step (3.0 g) was coevaporated with pyridine (2×20 mL) and dissolved in pyridine (100 mL). Dimethyoxytrityl chloride (3.5 g, 10 mmol) was dissolved in of pyridine (30 mL) and added to the diol dropwise over a period of 30 minutes. After 4 hours, the reaction was quenched with methanol (10 mL). The solvent was evaporated and the residual product portioned between saturated sodium bicarbonate solution and $CH_2Cl_2$ (100 mL each). The organic phase was dried over anhydrous $MgSO_4$, concentrated and the residue was subjected to silica gel flash column chromatography using hexanes-ethyl acetate-triethyl amine (60:39:1). The product containing fractions were combined, concentrated in vacuo and dried to give a yellow foamy solid. NMR analysis indicated the title compound as a pure homogenous dimethyoxytritylated solid (5.05 g, 83% yield).

EXAMPLE 28

(35, FIG. 9)

Compound 34 was phosphitylated (1.5 g, 2.5 mmol) in $CH_2Cl_2$ solvent (20 mL) by the addition of Diisopropylamine tetrazolide (214 mg, 1.25 mmol) and 2-cyanoethyl-N,N,N',N'-tetraisopropyl phosphorodiamidite (1.3 mL, 4.0 mmol). After stirring the solution overnight the solvent was evaporated and the residue was applied to silica column and eluted with hexanes-ethyl acetate-triethylamine (50:49:1). Concentration of the appropriate fractions gave 1.61 g of the phosphitylated compound as a yellow foam (81%).

EXAMPLE 29

Figure 10:
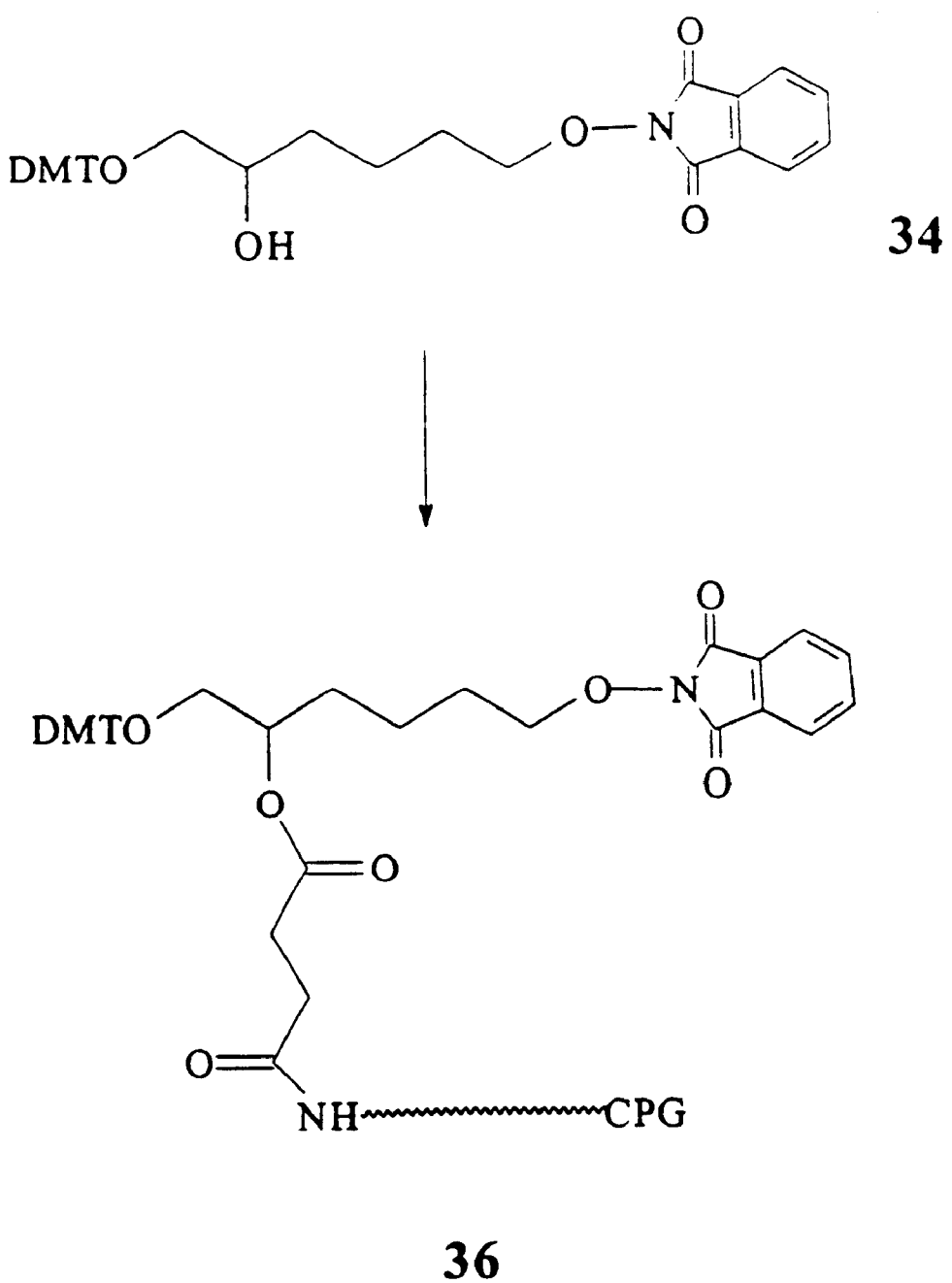
FIG. 10 shows a linking of compounds of the invention to CPG.

Attachment of O—N linker to CPG (36, FIG. 10)

Succinylated and capped CPG was prepared according to method described by P. D. Cook et al. (U.S. Pat. No. 5,541,307). Compound 34 (0.8 mmol), dimethylaminopyridine (0.2 mmol), 2.0 g of succinylated and capped CPG triethylamine (160 μL) and DEC (4.0 mmol) were shaken together for 24 hours. Pentachlorophenyl (1.0 mmol) was then added and the resulting mixture was shaken for 24 hours. The CPG beads were filtered off and washed thoroughly with pyridine (30 mL) dichloromethane (2×30 mL), $CH_3OH$ (30 mL) in ether. The CPG solid support was dried over $P_2O_5$ and its loading was determined to be 28 μmols/g.

EXAMPLE 30

Synthesis of oligonucleotides using ON linker

The following oligonucleotides were synthesized using compound 35, which is shown as an X at the 5' end of the oligonucleotide:
SEQ ID NO:1 5' XTTTTTTTTT 3'
SEQ ID NO:2 5' X TGC ATC CCC CAG GCC ACC ATT TTT T 3'
These oligonucleotides were synthesized as phosphorothioates. Compound 35 was used as a 0.1 M solution in $CH_3CN$. The coupling efficiency of ON-linker was >95% as shown by trityl colors. The oligonucleotides were retained in the solid support for solid phase conjugation.

EXAMPLE 31

Conjugation of pyrene to oligonucleotides using ON-linker

Oligonucleotide SEQ ID NO:1 in CPG (1 μmol) was taken in a glass funnel reactor and of 5% methylhydrazine (5 mL) in 9:1 $CH_2Cl_2/CH_3OH$ was added. The reactor was shaken for 30 minutes. The methyl hydrazine was drained, washed with $CH_2Cl_2$ and the methyl hydrazine reaction was repeated. The beads were washed with $CH_2Cl_2$ followed by ether and dried. Pyrene butyric acid-N-hydroxy succinimide (110 mg) in DMF (5 mL) was added. After shaking for 2 hours, the pyrene butyrate solution was drained, the oligonucleotide was deprotected in $NH_4OH$ for 30 minutes at room temperature. The aqueous solution was then filtered and an HPLC analysis was run. The product peak had a retention time of 34.85 minutes and the diode-array spectrophotometer showed pyrene absorption.

EXAMPLE 32

Conjugation of pyrene butyraldehyde to oligonucleotide (SEQ ID NO:2)

Pyrene butyraldehyde is added to SEQ ID NO:2 after $MeNHNH_2$ treatment. $NaCNBH_3$ in MeOH was then added. Deprotection of CPG followed by $NH_4OH$ cleaving of CPG showed pyrene conjugation to oligonucleotide.

EXAMPLE 33

To a stirred solution of 1,6-hexane-diol N-hydroxyphthalimide (6.525 g, 0.039 mol) and triphenylphosphine (10.2 g, 0.039 mol) in anhydrous THF (100 mL) was added diethylazidocarboxylate (DEAD, 7.83 g, 0.045 mol) over a period of 1 hour at 5° C. under an atmosphere of argon. The reaction mixture was then stirred at room temperature overnight. The bright yellow solution was concentrated under vacuum to remove the THF and portioned between $CH_2Cl_2$ and water. The organic layer was then washed with saturated $NaHCO_3$ followed by saturated NaCl. It was then dried over anhydrous $MgSO_4$ and applied to a silica column and eluted with EtOAC/hexane 1:1 to give 9.8 g. The material was contaminated with $Ph_3P=O$ and was recrystallized with $CH_2Cl_2$/ether. cl EXAMPLE 34

Figure 11:
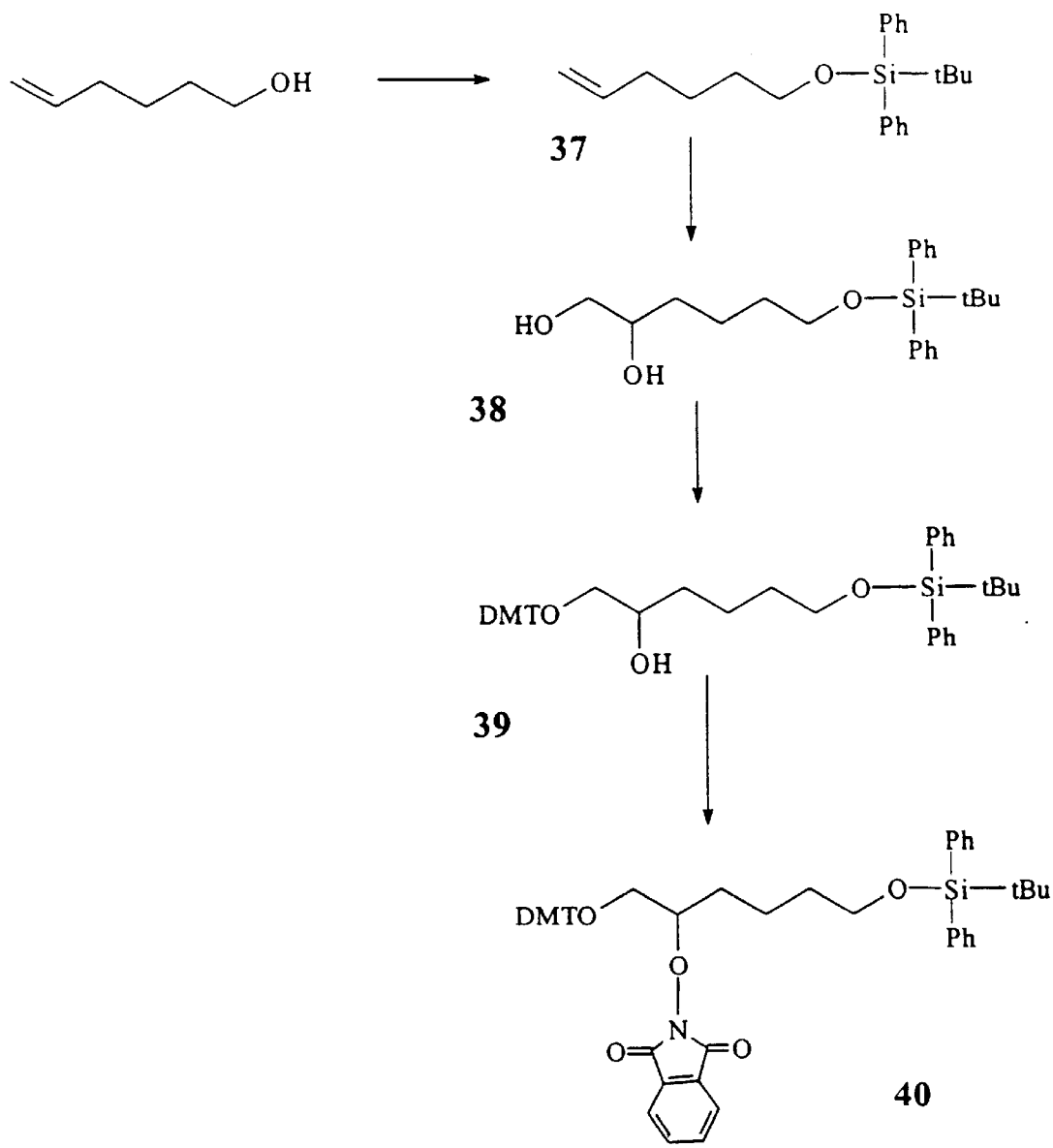
FIG. 11 shows a synthesis of intermediates and monomers of the invention.
Figure 12:
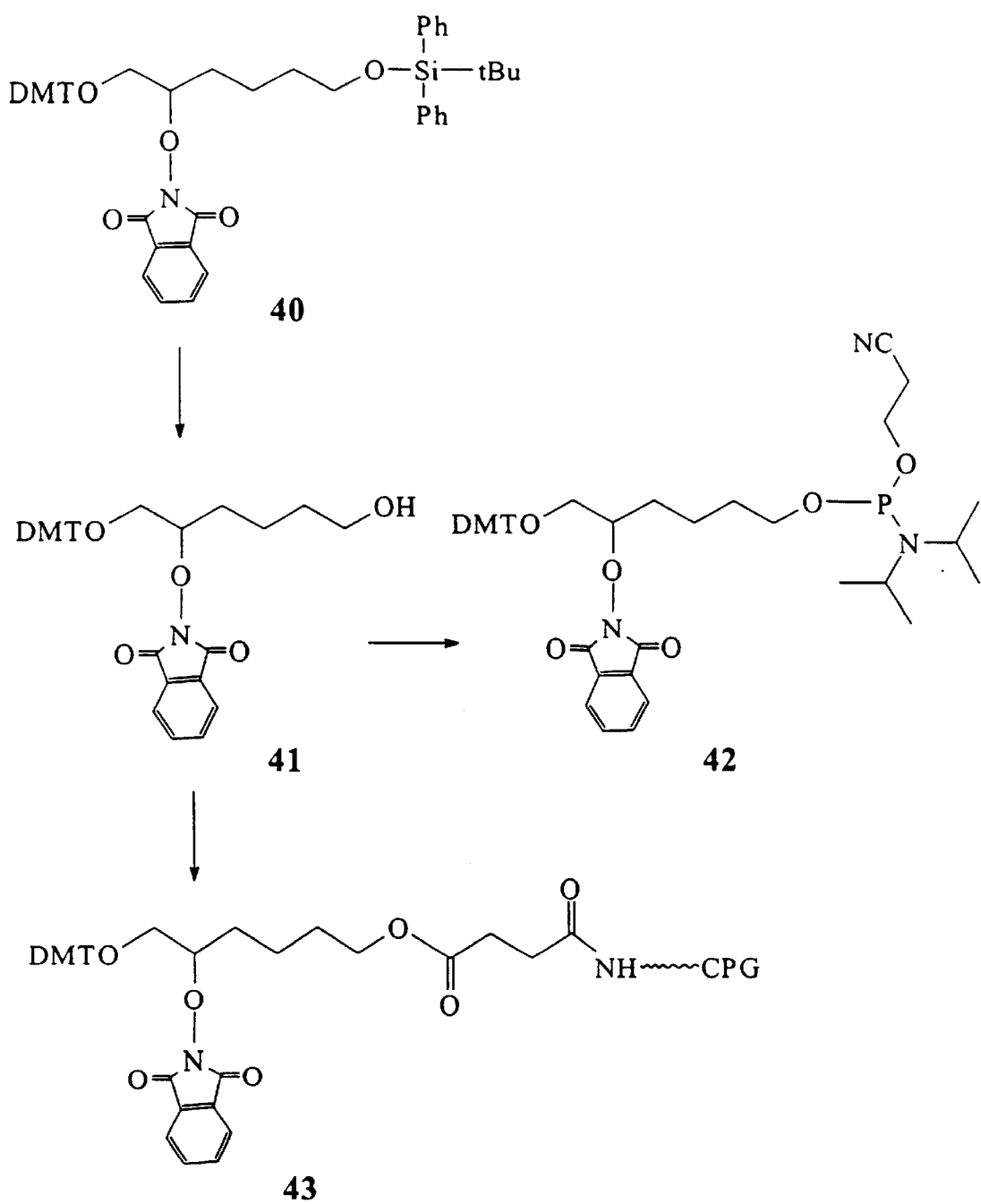
FIG. 12 shows a synthesis of intermediates and monomers of the invention.

(FIGS. 11 and 12)

5-hexene-1-ol is sylylated using imidazole/TBDPS-Cl in $CH_2Cl_2$ to give compound 37. Compound 37 is then dihydroxylated with $OSO_4$/NMMO as in (Example 25 for Compound 33) to give compound 38. Compound 38 is dimethoxytritylated at the primary alcohol function to give compound 39. It is then subjected to Mitsunobu reaction with N-hydroxyphthalimide to give compound 40. Compound 40 is then disilylated with TBAF (tetrabutyl ammonium fluoride, 1M in THF) to give compound 41. Compound 41 is then derivatized to a phosphoramidite 42. Compound 41 was also separately connected to controlled pore glass beads (Compound 43).

EXAMPLE 35

2,6,9-(β-D-ribofuranosyl) purine (5.64 g, 20 mmol) was added to a suspension of 800 mg of 60% sodium hydride in oil previously washed with hexanes in 100 mL of DMF under argon. After 1 hour of stirring at room temperature allyl bromide (2 mL, 1.1 equivalent) was added to the solution and stirred at room temperature overnight. The reaction mixture was evaporated and applied to a silica column and eluted with $CH_2Cl_2/CH_3OH$ (20:1) containing 1% triethylamine. The total yield of 2' and 3' O-allyl compounds was 5.02 g (77%). The mixture of 2' and 3' isomers was then exocyclic amine protected by treatment of DMF DMA in MeoH in quantitative yield. This material was then 5'-O-dimethyoxytritylated to give a mixture of 5'-O-dimethoxytrityl-N-2-formamidine-2'-O-(2-hydroxy ethyl)-guanosine and 5'-O-dimethoxytrityl-N2-formamidine-3'-O-(2-hydroxyethyl)guanosine in 2:1 ratio. The final compounds were purified by silica gel flash column chromatography.

EXAMPLE 36

2,6-diamino-9-(b-D-ribofuranosyl)purine (282 mg, 1 mmol) was added to a suspension of 40 mg of 60% sodium hydride in oil previously washed with hexanes in anhydrous DMF (5 mL). To this solution of 2-(bromoethoxy)-t-butyldimethyl silane (220 mL) was added. The mixture was stirred at room temperature overnight. The reaction mixture was evaporated and the resulting oil was partitioned between water and ethyl acetate. The organic layer was dried over $Na_2SO_4$. The reaction mixture was purified to give the 2' and 3' isomers over the silica gel. The 2'-material was then amine protected with DMF DMA and 5'-dimethoxytrilated to give 5'-O-dimethoxytrityl-N2-formamidine-2'-O-(2-TBDMS-hydroxyethyl)guanine.

EXAMPLE 37

Oligonucleotide Synthesis

Unsubstituted and substituted oligonucleotides are synthesized on an automated DNA synthesizer (Applied Biosystems model 380B) using standard phosphoramidite chemistry with oxidation by iodine. For phosphorothioate oligonucleotides, the standard oxidation bottle is replaced by 0.2 M solution of 3H-1,2-benzodithiole-3-one-1,1-dioxide in acetonitrile for the step wise thiation of the phosphite linkages. The thiation wait step is increased to 68 sec and is followed by the capping step. After cleavage from the CPG column and deblocking in concentrated ammonium hydroxide at 55° C. (18 hours), the oligonucleotides are purified by precipitating twice with 2.5 volumes of ethanol from a 0.5 M NaCl solution. Analytical gel electrophoresis is accomplished in 20% acrylamide, 8 M urea, 454 mM Tris-borate buffer, pH=7.0. Oligonucleotides and phosphorothioates are judged, based on polyacrylamide gel electrophoresis, to be greater than 80% full-length material.

EXAMPLE 38

General procedure for the attachment of 2'-deoxy-2'-substituted 5'-dimethoxytriphenylmethyl ribonucleosides to the 5'-hydroxyl of nucleosides bound to CPG support The 2'-deoxy-2'-substituted nucleoside that will reside at the terminal 3'-position of the oligonucleotide is protected as a 5'-DMT group (the cytosine and adenine exocyclic amino groups are benzoylated and the guanine amino is isobutrylated) and treated with trifluoroacetic acid/bromoacetic acid mixed anhydride in pyridine and dimethylaminopyridine at 50° C. for five hours. The solution is then evaporated under reduced pressure to a thin syrup which is dissolved in ethyl acetate and passed through a column of silica gel. The homogenous fractions are collected and evaporated to dryness. A solution of 10 mL of acetonitrile, 10 μM of the 3'-O-bromomethylester-modified nucleoside, and 1 mL of pyridine/dimethylaminopyridine (1:1) is syringed slowly (60 to 90 sec) through a 1 μM column of CPG thymidine (Applied Biosystems, Inc.) that had previously been treated with acid according to standard conditions to afford the free 5'-hydroxyl group. Other nucleoside-bound CPG columns may be employed. The eluent is collected and syringed again through the column. This process is repeated three times. The CPG column is washed slowly with 10 mL of acetonitrile and then attached to an ABI 380B nucleic acid synthesizer. Oligonucleotide synthesis is now initiated. The standard conditions of concentrated ammonium hydroxide deprotection that cleaves the thymidine ester linkage from the CPG support also cleaves the 3',5' ester linkage connecting the pyrimidine modified nucleoside to the thymidine that was initially bound to the CPG nucleoside. In this manner, any 2'-substituted nucleoside or generally any nucleoside with modifications in the heterocycle and/or sugar can be attached at the 3' end of an oligonucleotide.

EXAMPLE 39

Modified oligonucleotide synthesis for incorporation of 2'-substituted nucleotides A. ABI Synthesizer Oligonucleotide sequences incorporating 1-[2'-O-(2-phthalimido-N-oxyethyl)-5'-O-(4,4'-dimethoxytrityl)-β-D-ribofuranosyl]thymine were synthesized on an ABI 380B utilizing phosphoramidite chemistry with double-coupling and increased coupling times (5 and 10 min). The 2'-O-aminooxyethoxy phosphoramidite was used at a starting concentration of 0.08 M and 10% tert-butyl peroxide in acetonitrile was used as the oxidizer. Deoxy phosphoramidites were used at 0.2 M. Final concentrations of 2'-O-aminooxyethoxy and deoxy amidites were 0.04 M and 0.1 M, respectively. The oligonucleotides were cleaved from the CPG support and the base protecting groups removed using concentrated ammonia at 55° C. for 6 hours. The oligonucleotides were purified by size exclusion chromatography over Sephadex G25 and analyzed by electrospray mass spectrometry and capillary gel electrophoresis. Deoxy phosphoramidites were purchased from Perseptive Biosystems GmbH.

(SEQ ID NO:5) CTC GTA CCt TTC CGG TCC. LRMS (ES−) m/z: calcd: 5453.2; found: 5453.5.

(SEQ ID NO:6) CTC GTA Ctt ttC CGG TCC. LRMS (ES−) m/z: calcd: 5693.2; found: 5692.9.

(SEQ ID NO:3) GCG ttt ttt ttt tGC G. LRMS (ES−) m/z: calcd: 5625.7; found: 5625.9.

B. Expedite Synthesizer

Oligonucleotides incorporating 1-[2'-O-(2-phthalimdo-N-oxyethyl-5'-O-dimethoxytrityl-B-D-riboframosyl)-6-N-benzoyl-thymine were synthesized in an Expedite 8690 Synthesizer. 130 mg of the amidite was dissolved in dry CH$_3$CN (1.3 mL, app. 0.08M). 10% t-BuOOH in CH$_3$CN v/v was used as the oxidizing agent. An extended coupling and waiting times were used and a 10 min. oxidation was employed. The oligonucleotide synthesis revealed excellent coupling yields (>98%). Oligonucleotides were purified and their mass spec and profiles determined.

| Oligonucleo-tide | Sequence | SEQ ID NO: |
|---|---|---|
| V | CTC GTA CCa TTC CGG TCC | 7 |
| VI | GGa CCG Gaa GGT aCG aG | 8 |
| VII | aCC GaG GaT CaT GTC GTa CGC | 9 | where a represents 1-[2'-O-(2-aminooxyethyl)-β-D-ribofuranosyl]adenosine.

EXAMPLE 40

Oligonucleotide Having 2'-Substituted Oligonucleotides Regions Flanking Central 2'-Deoxy Phosphorothioate Oligonucleotide Region A 15 mer RNA target of the sequence 5'GCGTTTTTTTTTTGCG 3' (SEQ ID NO:3) is prepared in the normal manner on the DNA sequencer using RNA protocols. A series of complementary phosphorothioate oligonucleotides having 2'-O-substituted nucleotides in regions that flank a 2'-deoxy region are prepared utilizing 2'-O-substituted nucleotide precursors prepared as per known literature preparations, i.e. 2'-O-methyl, or as per the procedure of International Publication Number WO 92/03568, published Mar. 5, 1992. The 2'-O-substituted nucleotides are added as their 5'-O-dimethoxytrityl-3'-phosphoramidites in the normal manner on the DNA synthesizer. The complementary oligonucleotides have the sequence of 5' CGCAAAAAAAAAAAAACGC 3' (SEQ ID NO:4). The 2'-O-substituent is located in CGC and CG regions of these oligonucleotides. The 2'-O-substituents used are 2'-aminooxyethyl, 2'-O-ethylaminooxyethyl and 2'-O-dimethylaminooxyethyl.

EXAMPLE 41

Hybridization Analysis

A. Evaluation of the thermodynamics of hybridization of 2'-modified oligonucleotides.

The ability of the 2'-modified oligonucleotides to hybridize to their complementary RNA or DNA sequences is determined by thermal melting analysis. The RNA complement is synthesized from T7 RNA polymerase and a template-promoter of DNA synthesized with an Applied Biosystems, Inc. 380B RNA species is purified by ion exchange using FPLC (LKB Pharmacia, Inc.). Natural antisense oligonucleotides or those containing 2'-modifications at specific locations are added to either the RNA or DNA complement at stoichiometric concentrations and the absorbance (260 nm) hyperchromicity upon duplex to random coil transition is monitored using a Gilford Response II spectrophotometer. These measurements are performed in a buffer of 10 mM Na-phosphate, pH 7.4, 0.1 mM EDTA, and NaCl to yield an ionic strength of 10 either 0.1 M or 1.0 M.

Data is analyzed by a graphic representation of $1/T_m$ vs ln(Ct), where (Ct) was the total oligonucleotide concentration. From this analysis the thermodynamic para-meters are determined. Based upon the information gained concerning the stability of the duplex of heteroduplex formed, the placement of modified pyrimidine into oligonucleotides are assessed for their effects on helix stability. Modifications that drastically alter the stability of the hybrid exhibit reductions in the free energy (delta G) and decisions concerning their usefulness as antisense oligonucleotides are made.

As is shown in the following table (Table 1), the incorporation of 2'-substituted nucleosides of the invention into oligonucleotides can result in significant increases in the duplex stability of the modified oligonucleotide strand (the antisense strand) and its complementary RNA strand (the sense strand). The stability of the duplex increased as the number of 2'-substituted nucleosides in the antisense strand increased. As is evident from Table 1 the addition of a 2'-substituted nucleoside, irrespective of the individual nucleoside or the position of that nucleoside in the oligonucleotide sequence, resulted in an increase in the duplex stability.

In Table 1, the small case nucleosides represent nucleosides that include substituents of the invention. Effects of 2'-O-aminooxyethoxy modifications on DNA(antisense)—RNA(sense) duplex stability.

TABLE 1

| SEQ ID NO: | Sequence |
|---|---|
| 5 | CTC GTA CCT TTC CGG TCC |
| 5 | CTC GTA CCt TTC CGG TCC |
| 6 | CTC GTA CTT TTC CGG TCC |
| 6 | CTC GTA Ctt ttC CGG TCC |
| 3 | GCG TTT TTT TTT TGC G |
| 3 | GCG ttt ttt ttt tGC G |
| 3 | GCG TTT TTT TTT TGC G* |
| 3 | GCG ttt ttt ttt tGC G* |
| 7 | CTC GTA CCa TTC CGG TCC |
| 8 | GGa CCG Gaa GGT aCG aG |
| 9 | aCC GaG GaT CaT GTC GTa CGC | t = 1-[2'-O-(2-aminooxyethyl)-β-D-ribofuranosyl] thymine.
a = 1-[2'-O-(2-aminooxyethyl)-β-D-ribofuranosyl] adenosine.
* = was hybridized against DNA as sense strand.

| SEQ ID NO: | subs. | $T_m$ ° C. | $\Delta T_m$ ° C. | $\Delta T_m$ ° C./sub. |
|---|---|---|---|---|
| 5 | 0 | 65.2 ± 0.0 | | |
| 5 | 1 | 64.8 ± 0.1 | −0.5 ± 0.1 | −0.5 ± 0.1 |
| 6 | 0 | 61.5 ± 0.0 | | |
| 6 | 4 | 65.6 ± 0.4 | 4.1 ± 0.4 | 1.0 ± 0.1 |
| 3 | 0 | 48.2 ± 0.6 | | |
| 3 | 10 | 60.0 ± 0.0 | 11.9 ± 0.7 | 1.19 ± 0.07 |
| 3* | 0 | 53.5 ± 0.1† | | |
| 3* | 10 | 44.0 ± 0.2† | −9.4 ± 0.3† | −.94 ± 0.03† |

In Table 1, "subs." = Number of substitutions, as described above.

As is evident from Table 1, the duplexes formed between RNA and oligonucleotides containing 2'-substituents of the invention exhibited increased binding stability as measured by the hybridization thermodynamic stability. While we do not wish to be bound by theory, it is presently believed that the presence of a 2'-substituent of the invention results in the sugar moiety of the 2'-substituted nucleoside assuming substantially a 3'-endo conformation and this results in the oligonucleotide-RNA complex assuming an A-type helical conformation.

EXAMPLE 42

5'-O-tert-Butyldiphenylsilyl-$O^2$-2'-anhydro-5-methyluridie (101)

$O^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ML) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 ML) and dried (40° C., 1 mm Hg, 24 h) to 149 g (74.8%) of white solid. TLC and NMR were consistent with pure product.

EXAMPLE 43

5'-O-tert-Butyldiphenylsilyl-2'-O-(2-hydroxyethyl)-5-methyluridine (102)

In a 2 L stainless steel, unstirred pressure reactor was added borane in tetrahydrofuran (1.0 M, 2.0 eq, 622 ML). In the fume hood and with manual stirring, ethylene glycol (350 ML, excess) was added cautiously at first until the evolution of hydrogen gas subsided. 5'-O-tert-Butyldiphenylsilyl-$O^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure <100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product. NMR (DMSO-d6) d 1.05 (s, 9H, t-butyl), 1.45 (s, 3 H, CH3), 3.5–4.1 (m, 8 H, CH2CH2, 3'-H, 4'-H, 5'-H, 5"-H), 4.25 (m, 1 H, 2'-H), 4.80 (t, 1 H, CH2O—H), 5.18 (d, 2H, 3'-OH), 5.95 (d, 1 H, 1'-H), 7.35–7.75 (m, 11 H, Ph and C6-H), 11.42 (s, 1 H, N—H).

EXAMPLE 44

2'-O-([2-phthalimidoxy)ethyl]-5'-t-butyldiphenylsilyl-5-methyluridine (103)

Nucleoside 102 (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethyl acetate:hexane, 60:40). The solvent was evaporated in vacuum. Residue obtained was placed on a flash column and eluted with ethyl acetate:hexane (60:40), to get 103 as white foam (21.819, 86%). Rf 0.56 (ethyl acetate:hexane, 60:40). MS (FAB$^-$)m/e 684 (M–H$^+$)

EXAMPLE 45

5'-O-tert-butyldiphenylsilyl-2'-O-[(2-formadoximinooxy)ethyl]-5-methyluridine (104)

Compound 103 (3.1 g, 4.5 mmol) was dissolved in dry $CH_2Cl_2$ (4.5 mL) and methylhydrazine (300 mL, 4.64 mmol) was added dropwise at –10° C. to 0C. After 1 hr the mixture was filtered, the filtrate was washed with ice cold $CH_2Cl_2$ and the combined organic phase was washed with water, brine and dried over anhydrous $Na_2SO_4$. The solution concentrated to get 2'-O-(aminooxyethyl) thymidine, which was then dissolved in MeOH (67.5 mL). To this formaldehyde (20% aqueous solution, w/w, 1.1 eg.) was added and the mixture for 1 hr. Solvent removed under vacuum; residue chromatographed to get compound 104 as white foam (1.95, 78%). Rf 0.32 (5% MeOH in $CH_2Cl_2$). MS (Electrospray$^-$) m/e 566 (M–H$^\oplus$)

EXAMPLE 46

5'-O-tert-Butyldiphenylsilyl-2'-O-[N,N-dimethylaminooxyethyl]-5-methyluridine (105)

Compound 104 (1.77 g, 3.12 mmol) was dissolved in a solution of 1M pyridinium p-toluenesulfonate (PPTS) in dry MeOH (30.6 mL). Sodiumcyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 hr, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase dried over anhydrous $Na_2SO_4$, evaporated to dryness. Residue dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodiumcyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (23×25 mL). Ethyl acetate layer was dried over anhydrous $Na_2SO_4$; and evaporated to dryness The residue obtained was purified by flash column chromatography and eluted with 5% MeOH in $CH_2Cl_2$ to get 105 as a white foam (14.6 g, 80%). Rf 0.35 (5% MeOH in $CH_2Cl_2$). MS (FAB$^\oplus$) m/e 584 (M+H$^\oplus$)

EXAMPLE 47

2'-O-(dimethylaminooxyethyl)-5-methyluridine (106)

Triethylamine trihydrofluoride (3.9 mL, 24.0 mmol) was dissolved in dry THF and triethylamine (1.67 mL, 12 mmol, dry, kept over KOH). This mixture of triethylamine-2HF was then added to compound 105 (1.40 g, 2.4 mmol) and stirred at room temperature for 24 hrs. Reaction was monitored by TLC (5% MeOH in $CH_2Cl_2$). Solvent removed under vacuum and the residue placed on a flash column and eluted with 10% MeOH in $CH_2Cl_2$ to get 106 (766 mg, 92.5%). Rf 0.27 (5% MeOH in $CH_2Cl_2$). MS (FAB$^\oplus$) m/e 346 (M+H$^\oplus$)

EXAMPLE 48

5'-O-DMT-2'-O-(dimethylaminooxyethyl)-5-methyluridine (107)

Compound 106 (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in CH2Cl2 (containing a few drops of pyridine) to get 107 (1.13 g, 80%). Rf 0.44 ((10% MeOH in $CH_2Cl_2$). MS (FAB$^\oplus$) m/e 648 (M+H$^\oplus$)

EXAMPLE 49

5'-O-DMT-2'-O-(2-N,N-dimethylaminooxyethyl)-5-methyluridine-3'-[(2-cyanoethyl)-N,N-diisopropylphosphoramidite] (108)

Compound 107 (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,N$^1$,N$^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 108 as a foam (1.04 g, 74.9%). Rf 0.25 (ethyl acetate:hexane, 1:1). $^{31}$P NMR (CDCl$_3$) δ150.8 ppm; MS (FAB$^\oplus$) m/e 848 (M+H$^\oplus$)

EXAMPLE 50

2'/3'-O-allyl adenosine (109)

Adenosine (20 g, 74.84 mmol) was dried over $P_2O_5$ under high vacuum at 40° C. for two days. It was then suspended in DMF under inert atmosphere. Sodium hydride (2.5 g, 74.84 mmol, 60% dispersion in mineral oil), stirred at room temperature for 10 minutes. Then allyl bromide (7.14 mL, 82.45 mmol) was added dropwise and the reaction mixture was stirred at room temperature overnight. DMF was removed under vacuum and residue was washed with ethyl acetate (100 mL). Ethyl acetate layer was decanted. Filtrate obtained contained product. It was then placed on a flash column and eluted with 10% MeOH in $CH_2Cl_2$ to get 109 (15.19 g, 66%). Rf 0.4, 0.4a ((10% MeOH in $CH_2Cl_2$)

EXAMPLE 51

2'/3'-O-allyl-N$^6$-benzoyl adenosine (110)

Compound 109(15.19 g, 51.1 mmol) was dried over P$_2$O$_5$ under high vacuum overnight at 40° C. It was then dissolved in anhydrous pyridine (504.6 mL) under inert atmosphere. Trimethylchlorosilane (32.02 mL, 252.3 mmol) was added at 0° C. and the reaction mixture was stirred for 1 hr under inert atmosphere. Then benzoyl chloride (29.4 mL, 252.3 mmol) was added dropwise. Once the addition of benzoyl chloride was over, the reaction mixture was brought to room temperature and stirred for 4 hrs. Then the reaction mixture was brought to 0° C. in an ice bath. Water (100.9 mL). was added and the reaction mixture was stirred for 30 minutes. Then NH$_4$OH (100.0 mL, 30% aqueous solution w/w) was added, keeping the reaction mixture at 0° C. and stirring for an additional 1 hr. Solvent evaporated residue partitioned between water and ether. Product precipitates as an oil, which was then chromatographed (5% MeOH in CH$_2$Cl$_2$) to get 13 as a white foam (12.67 g, 62%).

EXAMPLE 52

3'-O-allyl-5'-O-tert-butyldiphenylsilyl-N$^6$-benzoyl-adenosine (111)

Compound 110 (11.17 g, 27.84 mmol) was dried over P$_2$O$_5$ under vacuum at 40° C., then dissolved in dry CH$_2$Cl$_2$ (56 mL, sure seal from Aldrich). 4-dimethylaminopyridine (0.34 g, 2.8 mmol), triethylamine (23.82 mL, 167 mmol) and t-butyldiphenylsilyl chloride were added. The reaction mixture was stirred vigorously for 12 hr. Reaction was monitored by TLC (ethyl acetate:hexane 1:1). It was then diluted with CH$_2$Cl$_2$ (50 mL) and washed with water (3×30 mL) Dichloromethane layer was dried over anhydrous Na$_2$SO$_4$ and evaporated to dryness. Residue purified by flash chromatography (ethyl acetate:hexane 1:1 as eluent) to get 111 as a white foam (8.85 g, 49%). Rf 0.35 (ethyl acetate:hexane, 1:1)

EXAMPLE 53

5'-O-tert-butyldiphenylsilyl-N$^6$-benzoyl-2'-O-(2,3-dihydroxypropyl)-adenosine (112)

Compound 111 (5.5 g, 8.46 mmol), 4-methylmorpholine N-oxide (1.43 g, 12.18 mmol) were dissolved in dioxane (45.42 mL). 4% aqueous solution of OSO$_4$ (1.99 mL, 0.31 mmol) was added. The reaction mixture was protected from light and stirred for 3 hrs. Reaction was monitored by TLC (5% MeOH in CH$_2$Cl$_2$). Ethyl acetate (100 mL) was added and the resulting reaction mixture was washed with water (1×50 mL). Ethyl acetate layer was dried over anhydrous Na$_2$SO$_4$ and evaporated to get 112 (5.9 g) and used for next step without purification. Rf 0.17 (5% MeOH in CH$_2$Cl$_2$)

EXAMPLE 54

5'-O-tert-butyldiphenylsilyl-N$^6$-benzoyl-2'-O-(formylmethyl)-adenosine (113)

Compound 112 (5.59 g, 8.17 mmol) was dissolved in dry CH$_2$Cl$_2$ (40.42 mL). To this NaIO$_4$ adsorbed on silica gel (Ref. *J. Org. Chem.* 1997, 62, 2622–2624) (16.34 g, 2 g/mmol) was added and stirred at ambient temperature for 30 minutes. Reaction monitored by TLC (5% MeOH in CH$_2$Cl$_2$). Reaction mixture was filtered and the filtrate washed thoroughly with CH$_2$Cl$_2$. Dichloromethane layer evaporated to get the aldehyde 113 (5.60 g) that was used in the next step without purification. Rf 0.3 (5% MeOH in CH$_2$Cl$_2$)

EXAMPLE 55

5'-O-tert-butyldiphenylsilyl-N$^6$-2'-O-(2-hydroxyethyl) adenosine (114)

Compound 113 (5.55 g, 8.50 mmol) was dissolved in a solution of 1M pyridinium p-toluenesulfonate in anhydrous MeOH (85 mL). Reaction mixture was protected from moisture. Sodiumcyanoborohydride (1.08 g, 17.27 mmol) was added and reaction mixture stirred at ambient temperature for 5 hrs. The progress of the reaction was monitored by TLC (5% MeOH in CH$_2$Cl$_2$). The reaction mixture was diluted with ethyl acetate (150 mL), then washed with 5% NaHCO$_3$ (75 mL) and brine (75 mL). Ethyl acetate layer was dried over anhydrous Na$_2$SO$_4$ and evaporated to dryness. Residue purified by flash chromatography (5% MeOH in CH$_2$Cl$_2$) to get 114 (4.31 g, 77.8%). Rf 0.21 (5% MeOH in CH$_2$Cl$_2$). MS (FAB$^\oplus$) m/e 655 (M+H$^\oplus$), 677 (M+Na$^\oplus$)

EXAMPLE 56

5'-tert-butyldiphenylsilyl-N$^6$-benzoyl-2'-O-(2-phthalimidooxyethyl) adenosine (115)

Compound 114 (3.22 g, 4.92 mmol) was mixed with triphenylphosphine (1.55 g, 5.90 mmol) and N-hydroxyphthalimide (0.96 g, 5.90 mmol). It was then dried over P$_2$O$_5$ under vacuum at 40° C. for two days. Dissolved dried mixture in anhydrous THF (49.2 mL) under inert atmosphere. Diethyl azodicarboxylate (0.93 mL, 5.90 mmol) was added dropwise. The rate of addition was maintained such that resulting deep red coloration is just discharged before adding the next drop. After the addition was completed, the reaction was stirred for 4 hrs, monitored by TLC (ethyl acetate:hexane 70:30). Solvent was removed under vacuum and the residue dissolved in ethyl acetate (75 mL). The ethyl acetate layer was washed with water (75 mL), then dried over Na$_2$SO$_4$, concentrated and chromatographed (ethylacetate:hexane 70:30) to get 115 (3.60 g, 91.5%). Rf 0.27 ethyl acetate:hexane, 7:3) MS (FAB$^\oplus$) m/e 799 (M+H$^\oplus$), 821 (M+Na$^\oplus$)

EXAMPLE 57

5'-O-tert-butyldiphenylsilyl-N$^6$-benzoyl-2'-O-(2-formaldoximinooxyethyl) adenosine (116)

Compound 115 (3.5 g, 4.28 mmol) was dissolved in CH$_2$Cl$_2$ (43.8 mL). N-methylhydrazine (0.28 mL, 5.27 mmol) was added at −10° C. and the reaction mixture was stirred for 1 hr at −10 to 0° C. Reaction monitored by TLC (5% MeOH in CH$_2$Cl$_2$). A white precipitate formed was filtered and filtrate washed with ice cold CH$_2$Cl$_2$ thoroughly. Dichloromethane layer evaporated on a rotary evaporator keeping the water bath temperature at less than 25° C. Residue obtained was then dissolved in MeOH (65.7 mL). Formaldehyde (710 mL, 4.8 mmol, 20% solution in water) was added and the reaction mixture was stirred at ambient temperature for 1 hr. Reaction monitored by $^1$H NMR. Reaction mixture concentrated and chromatographed (5% MeOH in CH$_2$Cl$_2$) to get 116 as a white foam (2.47 g, 83%). Rf 0.37 (5% MeOH in CH$_2$Cl$_2$). MS (FAB$^\oplus$) m/e 681 (M+H$^\oplus$)

EXAMPLE 58

5'-tert-butyldiphenylsilyl-N$^6$-benzoyl-2'-O-(2-N,N-dimethylaminooxyethyl) adenosine (117)

Compound 116 (2.2 g, 3.23 mmol) was dissolved in a solution of 1M pyridinium p-toluenesulfonate (PPTS) in MeOH (32 mL). Reaction protected from moisture. Sodium cyanoborohydride (0.31 g) was added at 10° C. and reaction mixture was stirred for 10 minutes at 10° C. It was then brought to ambient temperature and stirred for 2 hrs, monitored by TLC (5% MeOH in $CH_2Cl_2$). 5% aqueous sodium bicarbonate (100 mL) and extracted with ethyl acetate (3×50 mL). Ethyl acetate layer was dried over anhydrous $Na_2SO_4$ and evaporated to dryness. Residue was dissolved in a solution of 1M PPTS in MeOH (32 mL). Formaldehyde (0.54 mL, 3.55 mmol, 20% aqueous solution) was added and stirred at room temperature for 10 minutes. Sodium cyanoborohydride (0.31 g) was added at 10° C. and stirred for 10 minutes at 10° C. Then the reaction mixture was removed from ice bath and stirred at room temperature for an additional 2 hrs, monitored by TLC (5% MeOH in $CH_2Cl_2$). Reaction mixture was diluted with 5% aqueous $NaHCO_3$ (100 mL) and extracted with ethyl acetate (3×50 mL). Ethyl acetate layer was dried, evaporated and chromatographed (5% MeOH in $CH_2Cl_2$) to get 117 (1.9 g, 81.8%). Rf 0.29 (5% MeOH in $CH_2Cl_2$). MS ($FAB^\oplus$) m/e 697 ($M+H^\oplus$), 719 ($M+Na^\oplus$)

EXAMPLE 59

$N^6$-benzoyl-2'-O-(N,N-dimethylaminooxyethyl) adenosine (118)

To a solution of $Et_3N$-3HF (1.6 g, 10 mmol) in anhydrous THF (10 mL) triethylamine (0.71 mL, 5.12 mmol) was added. Then this mixture was added to compound 117 (0.72 g, 1 mmol) and stirred at room temperature under inert atmosphere for 24 hrs. Reaction monitored by TLC (10% MeOH in $CH_2Cl_2$). Solvent removed under vacuum and the residue chromatographed (10% MeOH in $CH_2Cl_2$) to get 118 (0.409 g, 89%). Rf 0.40 (10% MeOH in $CH_2Cl_2$). MS ($FAB^\oplus$) m/e 459 ($M+H^\oplus$)

EXAMPLE 60

5'-O-dimethoxytrityl-$N^6$-benzoyl-2'-O-(2-N,N-dimethylaminooxyethyl) adenosine (119)

Compound 118 (0.4 g, 0.87 mmol) was dried over $P_2O_5$ under vacuum overnight at 40° C. 4-dimethylaminopyridine (0.022 g, 0.17 mmol) was added. Then it was co-evaporated with anhydrous pyridine (9 mL). Residue was dissolved in anhydrous pyridine (2 mL) under inert atmosphere, and 4,4'-dimethoxytrityl chloride (0.58 g, 1.72 mmol) was added and stirred at room temperature for 4 hrs. TLC (5% MeOH in $CH_2Cl_2$) showed the completion of the reaction. Pyridine was removed under vacuum, residue dissolved in $CH_2Cl_2$ (50 mL) and washed with aqueous 5% $NaHCO_3$ (30 mL) solution followed by brine (30 mL). $CH_2Cl_2$ layer dried over anhydrous $Na_2SO_4$ and evaporated. Residue chromatographed (5% MeOH in $CH_2Cl_2$ containing a few drops of pyridine) to get 119 (0.5 g, 75%). Rf 0.20 (5% MeOH in $CH_2Cl_2$). MS (Electrospray⁻) m/e 759 ($M+H^\oplus$)

EXAMPLE 61

$N^6$-benzoyl-5'-O-DMT-2'-O-(N,N-dimethylaminooxyethyl) adenosine-3'-O-phosphoramidite (120)

Compound 119 (0.47 g, 0.62 mmol) was co-evaporated with toluene (5 mL). Residue was mixed with N,N-diisopropylamine tetrazolide (0.106 g, 0.62 mmol) and dried over $P_2O_5$ under high vacuum overnight. Then it was dissolved in anhydrous $CH_3CN$ (3.2 mL) under inert atmosphere. 2-cyanoethyl-tetraisopropyl phosphordiamidite (0.79 mL, 2.48 mmol) was added dropwise and the reaction mixture was stirred at room temperature under inert atmosphere for 6 hrs. Reaction was monitored by TLC (ethyl acetate containing a few drops of pyridine). Solvent was removed, then residue was dissolved in ethyl acetate (50 mL) and washed with 5% aqueous $NaHCO_3$ (2×25 mL). Ethyl acetate layer was dried over anhydrous $Na_2SO_4$, evaporated, and residue chromatographed (ethyl acetate containing a few drops of pyridine) to get 120 (0.45 g, 76%). MS (Electrospray⁻) m/e 959 ($M+H^\oplus$) $^{31}P$ NMR ($CDCl_3$) δ151.36, 150.77 ppm

EXAMPLE 62

2'/3'-O-allyl-2,6-diaminopurine riboside (121 and 122)

2,6-Diaminopurine riboside (30 g, 106.4 mmol) was suspended in anhydrous DMF (540 ML). Reaction vessel was flushed with argon. Sodium hydride (3.6 g, 106.4 mmol, 60% dispersion in mineral oil) was added and the reaction stirred for 10 min. Allyl bromide (14.14 mL, 117.22 mmol) was added dropwise over 20 min. The resulting reaction mixture stirred at room temperature for 20 hr. TLC (10% MeOH in $CH_2Cl_2$) showed complete disappearance of starting material. DMF was removed under vacuum and the residue absorbed on silica was placed on a flash column and eluted with 10% MeOH in $CH_2Cl_2$. Fractions containing mixture of 2' and 3' allylated product was pooled together and concentrated to dryness to yield a mixture of 121 and 122 (26.38 g, 77%). Rf 0.26, 0.4 (10% MeOH in $CH_2Cl_2$)

EXAMPLE 63

2'-O-allyl-guanosine (123)

A mixture of 121 and 122 (20 g, 62.12 mmol) was suspended in 100 mm sodium phosphate buffer (pH 7.5) and adenosine deaminase (1 g) was added. The resulting solution was stirred very slowly for 60 hr, keeping the reaction vessel open to atmosphere. Reaction mixture was then cooled in ice bath for one hr and the precipitate obtained was filtered, dried over $P_2O_5$ under high vacuum to yield 123 as white powder (13.92 g, 69.6% yield). Rf 0.19 (20% MeOH in $CH_2Cl_2$)

EXAMPLE 64

2'-O-allyl-3', 5'-bis(tert-butyl diphenylsilyl) guanosine (124)

2'-O-allyl-guanosine (6 g, 18.69 mmol) was mixed with imidazole (10.18 g, 14.952 mmol) and was dried over $P_2O_5$ under high vacuum overnight. It was then flushed with argon. Anhydrous DMF (50 mL) was added and stirred with the reaction mixture for 10 minutes. To this tert-butyldiphenylsilyl chloride (19.44 mL, 74.76 mmol) was added and the reaction mixture stirred overnight under argon atmosphere. DMF was removed under vacuum and the residue was dissolved in ethyl acetate (100 mL) and washed with water (2×75 mL). Ethyl acetate layer was dried over anhydrous $Na_2SO_4$ and evaporated to dryness. Residue placed on a flash column and eluted with 5% MeOH in $CH_2Cl_2$. Fractions containing the product were pooled together and evaporated to yield 124 (10.84 g, 72% yield) as a white foam. Rf=? MS ($FAB^\oplus$) m/e 800 ($M+H^\oplus$), 822 ($M+Na^\oplus$)

EXAMPLE 65

2'-O-(2-hydroxyethyl)-3', 5'-bis(tert-butyldiphenylsilyl) guanosine (125)

Compound 124 (9 g, 11.23 mmol) was dissolved in $CH_2Cl_2$ (80 mL). To the clear solution acetone (50 ML), 4-methyl morpholine-N-oxide (1.89 g, 16.17 mmol) was added. The reaction flask was protected from light. Thus 4% aqueous solution of osmium tetroxide was added and the reaction mixture was stirred at room temperature for 6 hr. Reaction volume was concentrated to half and ethyl acetate (50 mL) was added. It was then washed with water (30 mL) and brine (30 mL). Ethyl acetate layer was dried over anhydrous $Na_2SO_4$ and evaporated to dryness. Residue was then dissolved in $CH_2Cl_2$ and $NaIO_4$ adsorbed on silica (21.17 g, 2 g/mmol) was added and stirred with the reaction mixture for 30 min. The reaction mixture was filtered and silica was washed thoroughly with $CH_2Cl_2$. Combined $CH_2Cl_2$ layer was evaporated to dryness. Residue was then dissolved in dissolved in 1M pyridinium-p-toluene sulfonate (PPTS) in dry MeOH (99.5 mL) under inert atmosphere. To the clear solution sodium cyanoborohydride (1.14 g, 18.2 mmol) was added and stirred at room temperature for 4 hr. 5% aqueous sodium bicarbonate (50 mL) was added to the reaction mixture slowly and extracted with ethyl acetate (2×50 mL). Ethyl acetate layer was dried over anhydrous $Na_2SO_4$ and evaporated to dryness. Residue placed on a flash column and eluted with 10% MeOH in $CH_2Cl_2$ to yield 125 (6.46 g, 72% yield). MS (Electrospray–) m/e 802 $(M-H^{\oplus})$

EXAMPLE 66

2'-O-[(2-phthalimidoxy)ethyl]-3', 5'-bis(tert butyldiphenylsilyl) guanosine (126)

Compound 125 (3.7 g, 4.61 mmol) was mixed with $Ph_3P$ (1.40 g, 5.35 mmol), and hydroxy phthalimide (0.87 g, 5.35 mmol). It was then dried over $P_2O_5$ under high vacuum for two days at 40° C. These anhydrous THF (46.1 mmol) was added to get a clear solution under inert atmosphere. Diethylazidocarboxylate (0.73 mL, 4.61 mmol) was added dropwise in such a manner that red color disappears before addition of the next drop. Resulting solution was then stirred at room temperature for 4 hr. THF was removed under vacuum and the residue dissolved in ethyl acetate (75 mL) and washed with water (2×50 mL). Ethyl acetate layer was dried over anhydrous $Na_2SO_4$ and concentrated to dryness. Residue was purified by column chromatography and eluted with 7% MeOH in ethyl acetate to yield 126 (2.62 g, 60% yield). Rf 0.48 (10% MeOH in $CH_2Cl_2$). MS (FAB$^-$) m/e 947 $(M-H^{\oplus})$.

EXAMPLE 67

2'-O-(2-phthalimido-N-oxyethyl)-3', 5'-O-bis-tert-butyldiphenylsilyl-N2-isobutyrylguanosine (127)

2'-O-(2-phthalimido-N-oxyethyl)-3', 5'-O-bis-tert-butyldiphenylsilyl guanosine (3.66 g, 3.86 mmol) was dissolved in anhydrous pyridine (40 ML), the solution was cooled to 5° C., and isobutyryl chloride (0.808 ML, 7.72 mmol) was added dropwise. The reaction mixture was allowed to warm to 25° C., and after 2 h additional isobutyryl chloride (0.40 ML, 3.35 mmol) was added at 25° C. After 1 h the solvent was evaporated in vaccuo (0.1 torr) at 30° C. to give a foam which was dissolved in ethyl acetate (150 ML) to give a fine suspension. The suspension was washed with water (2×15 ML) and brine (4 ML), and the organic layer was separated and dried over $MgSO_4$. The solvent was evaporated in vaccuo to give a foam, which was purified by column chromatography using $CH_2Cl_2$—MeOH, 94:6, v/v, to afford the title compound as a white foam (2.57 g, 65%). $^1$H NMR(CDCl$_3$): d 11.97 (br s, 1H), 8.73 (s, 1H), 7.8–7.2 (m, 25H), 5.93 (d, 1H, $J_{1',2'}$=3.3 Hz), 4.46 (m, 1H), 4.24 (m, 2H), 3.83 (m, 2H), 3.60 (m, 2H), 3.32 (m, 1H), 2.67 (m, 1H), 1.30 (d, 3H, J=3.2 Hz), 1.26 (d, 3H, j=3.1 Hz), 1.05 (s, 9H), 1.02 (s, 9H).

This compound was further derivatized into the corresponding phosphoramidite using the chemistries described above for A and T analogs to give compound 128.

EXAMPLE 68

3'-O-acetyl-2'-O-(2-N,N-dimethylaminooxyethyl)-5'-O-tert-butyldiphenylsilyl thymidine (129)

Compound 105 (3.04 g, 5.21 mmol) was dissolved in chloroform (11.4 mL). To this was added dimethylaminopyridine (0.99 g, 8.10 mmol) and the reaction mixture was stirred for 10 minutes. Acetic anhydride (0.701 g, 6.87 mmol) was added and the reaction mixture was stirred overnight. The reaction mixture was then diluted with $CH_2Cl_2$ (40 mL) and washed with saturated $NaHCO_3$ (30 ML) and brine (30 ML). $CH_2Cl_2$ layer evaporated to dryness. Residue placed on a flash column and eluted with ethyl acetate:hexane (80:20) to yield 129. Rf 0.43 (ethyl acetate:hexane, 80:20). MS (Electrospray$^-$) m/e 624 (M-H$^-$)

EXAMPLE 69

2'-O-(2-N,N-dimethylaminooxyethyl)-5'-O-tert-butyldiphenylsilyl 5-methyl cytidine (130)

A suspension of 1,2,4-triazole (5.86 g, 84.83 mmol) in anhydrous $CH_3CN$ (49 mL) was cooled in an ice bath for 5 to 10 min. under argon atmosphere. To this cold suspension $POCl_3$ (1.87 mL, 20 mmol) was added slowly over 10 min. and stirring continued for an additional 5 min. Triethylamine (13.91 mL, 99.8 mmol) was added slowly over 30 min., keeping the bath temperature around 0–2° C. After the addition was complete the reaction mixture was stirred at this temperature for an additional 30 minutes when compound 35 (3.12 g, 4.99 mmol) was added in anhydrous acetonitrile (3 mL) in one portion. The reaction mixture was stirred at 0–2° C. for 10 min. Then ice bath was removed and the reaction mixture was stirred at room temperature for 1.5 hr. The reaction mixture was cooled to ° C. and this was concentrated to smaller volume and dissolved in ethyl acetate (100 mL), washed with water (2×30 mL) and brine (30 mL). Organic layer was dried over anhydrous $Na_2SO_4$ and concentrated to dryness. Residue obtained was then dissolved in saturated solution of $NH_3$ in dioxane (25 mL) and stirred at room temperature overnight. Solvent was removed under vacuum. The residue was purified by column chromatography and eluted with 10% MeOH in $CH_2Cl_2$ to get 130.

EXAMPLE 70

2'-O-(2,N,N-dimethylaminooxyethyl)-$N^4$-benzoyl-5'-O-tert-butyldiphenylsilylcytidine (131)

Compound 130 (2.8 g, 4.81 mmol) was dissolved in anhydrous DMF (12.33 mL). Benzoic anhydride (1.4 g, 6.17 mmol) was added and the reaction mixture was stirred at room temperature overnight. Methanol was added (1 mL) and solvent evaporated to dryness. Residue was dissolved in dichloromethane (50 mL) and washed with saturated solution of $NaHCO_3$ (2×30 ML) followed by brine (30 mL). Dichloromethane layer was dried over anhydrous $Na_2SO_4$ and concentrated. The residue obtained was purified by column chromatography and eluted with 5% MeOH in $CH_2Cl_2$ to yield 131 as a foam.

EXAMPLE 71

N⁴-Benzoyl-2'-O-(2-N,N-dimethylaminooxyethyl)-5-methyl cytidine (132)

Compound 131 (2.5 g, 3.9 mmol) was dried over $P_2O_5$ under high vacuum. In a 100 mL round bottom flask, triethylamine trihydrofluoride (6.36 mL, 39 mmol) is dissolved in anhydrous THF (39 mL). To this, triethylamine (2.72 mL, 19.5 mmol) was added and the mixture was quickly poured into compound 131 and stirred at room temperature overnight. Solvent is removed under vacuum and the residue kept in a flash column and eluted with 10% MeOH in $CH_2Cl_2$ to yield 132.

EXAMPLE 72

N⁴-Benzoyl-2'-O-(2-N,N-dimethylaminooxyethyl)-5-O'-dimetoxytrityl-5-methyl cytidine (133)

Compound 132 (1.3 g, 2.98 mmol) was dried over $P_2O_5$ under high vacuum overnight. It was then co-evaporated with anhydrous pyridine (10 mL). Residue was dissolved in anhydrous pyridine (15 mL), 4-dimethylamino pyridine (10.9 mg, 0.3 mmol) was added and the solution was stirred at room temperature under argon atmosphere for 4 hr. Pyridine was removed under vacuum and the residue dissolved in ethyl acetate and washed with 5% $NaHCO_3$ (20 mL) and brine (20 mL). Ethyl acetate layer was dried over anhydrous $Na_2SO_4$ and concentrated to dryness. Residue was placed on a flash column and eluted with 10% MeOH in $CH_2Cl_2$ containing a few drops of pyridine to yield compound 133.

EXAMPLE 73

N⁴-Benzoyl-2'-O-(2-N,N-dimethylaminooxyethyl)-5-dimethoxytrityl-5-methyl cytidine-3'-O-phosphoramidite (134)

Compound 133 (1.54 g, 2.09 mmol) was co-evaporated with toluene (10 mL). It was then mixed with diisopropylamine tetrazolide (0.36 g, 2.09 mmol) and dried over $P_2O_5$ under high vacuum at 40° C. overnight. Then it was dissolved in anhydrous acetonitrile (11 mL) and 2-cyanoethyl-tetraisopropylphosphoramidite (2.66 mL, 8.36 mmol) was added. The reaction mixture was stirred at room temperature under inert atmosphere for 4 hr. Solvent was removed under vacuum. Ethyl acetate (50 mL) was added to the residue and washed with 5% $NaHCO_3$ (30 mL) and brine (30 mL). Organic phase was dried over anhydrous $Na_2SO_4$ and concentrated to dryness. Residue placed on a flash column and eluted with ethylacetate:hexane (60:40) containing a few drops of pyridine to get 134.

EXAMPLE 74

2'-O-dimethylaminooxyethyl-2,6-diaminopurine riboside phosphoramidite (135)

For the incorporation of 2'-O-dimethylaminooxyethyl-2,6-diaminopurine riboside into oligonucleotides, we elected to use the phosphoramidite of protected 6-amino-2-fluoropurine riboside 135. Post-oligo synthesis, concomitant with the deprotection of oligonucleotide protection groups, the 2-fluoro group is displaced with ammonia to give the 2,6-diaminopurine riboside analog. Thus, 2,6-diaminopurine riboside is alkylated with dimethylaminooxyethylbromide 136 to afford a mixture of 2'-O-dimethylaminooxyethyl-2,6-diaminopurine riboside 137 and the 3'-isomer 138. Typically after functionalizing the 5'-hydroxyl with DMT to provide 5'-O-(4,4'-dimethoxytrityl)-2'-O-dimethylaminooxyethyl-2,6-diaminopurine riboside 139, the 2'-isomer may be resolved chromatographically. Fluorination of 139 via the Schiemann reaction (Krolikiewicz, K.; Vorbruggen, H. Nucleosides Nucleotides, 1994, 13, 673–678) provides 2'-O-dimethylaminooxyethyl-6-amino-2-fluoro-purine riboside 140 and standard protection protocols affords 5'-O-(4,4'-dimethoxytrityl)-2'-O-dimethylaminooxyethyl-6-dimethyformamidine-2-fluoropurine riboside 140. Phosphitylation of 140 gives 5'-O-(4,4'-dimethoxytrityl)-2'-O-dimethylaminooxyethyl-6-dimethyformamidine-2-fluoropurine riboside-3'-[(2-cyanoethyl)-N,N-diisopropylphosphoramidite] 138.

In the event that compound 139 cannot be resolved chromatographically from the 3'-isomer, the mixture of compounds 137 and 138 may be treated with adenosine deaminase, which is known to selectively deaminate 2'-O-substituted adenosine analogs in preference to the 3'-O-isomer, to afford 2'-O-dimethylaminooxyethylguanosine 142. 5'-O-(4,4'-dimethoxytrityl)-2'-O-dimethylaminooxyethylguanosine 140 may be converted to the 2,6-diaminopurine riboside analog 139 by amination of the 6-oxo group (Gryaznov, S.; Schultz, R. G. Tetrahedron Lett. 1994, 2489–2492). This was then converted to the corresponding amidite 144 by standard protection methods and protocols for phosphitylation.

EXAMPLE 75

2'/3'-O-[2-(tert-butyldimethylsilylhydroxy)ethyl]-2,6-diaminopurine riboside (145 and 146)

2,6-diaminopurine riboside (10 g, 35.46 mmol) was dried over $P_2O_5$ under high vacuum. It was suspended in anhydrous DMF (180 mL) and NaH (1.2 g, 35.46 mmol, 60% dispersion in mineral oil) was added. The reaction mixture was stirred at ambient temperature at inert atmosphere for 30 minutes. To this (2-bromoethoxy)-tert-butyldimethylsilane (12.73 g, 53.2 mmol) was added dropwise and the resulting solution was stirred at room temperature overnight. DMF was removed under vacuum, residue was dissolved in ethyl acetate (100 mL) and washed with water (2×70 mL). Ethyl acetate layer was dried over anhydrous $MgSO_4$ and concentrated to dryness. Residue was placed on a flash column and eluted with 5% MeOH in $CH_2Cl_2$ to get a mixture of products (6.0711 g, 31% yield). Rf 0.49, 0.59, 0.68 (5% MeOH in $CH_2Cl_2$).

EXAMPLE 76

2'-O-aminooxyethyl analogs

Various other 2'-O-aminooxyethyl analogs of nucleoside (for e.g., 2,6-diaminopurine riboside) may be prepared as compounds 154. Thus, alkylation of 2,6-diamino purine with (2-bromoethoxy)-tert-butyldimethylsilane gives 2'-O-tert-butyldimethylsilyloxyethyl-2,6-diaminopurine riboside 145 and the 3'-isomer 146. The desired 2'-O-isomer may be resolved by preparation of 5'-O-(4,4'-dimethoxytrityl)-2'-O-tert-butyldimethylsilyloxyethyl-2,6-diaminopurine riboside 147 and subjecting the mixture to column chromatography. Deprotection of the silyl group provides 5'-O-(4,4'-dimethoxytrityl)-2'-O-hydroxyethyl-2,6-diaminopurine riboside 148 which undergoes a Mitsunobu reaction to give 5'-O-(4,4'-dimethoxytrityl)-2'-O-(2-phthalimido-N-oxyethyl)-2,6-diaminopurine riboside 149. Treatment of 149 under Schiemann conditions effects fluorination and deprotection of the DMT group to yield 2'-O-(2-phthalimido-N-oxyethyl)-6-amino-2-fluoropurine riboside 150. Standard protection conditions provides 5'-O-(4,4'-dimethoxytrityl)-2'-O-(2-phthalimido-N-oxyethyl)-6-dimethyformamidine-2-fluoropurine riboside 151 and deprotection of the phthalimido function affords 5'-O-(4,4'-dimethoxytrityl)-2'-O-aminooxyethyl-6-dimethyformamidine-2-fluoropurine riboside 152.

Reductive amination of 152 with aldehydes or dialdehydes results in cyclic or acyclic disubstituted 2'-O-aminooxyethyl analogs 153. Phosphitylation of 153 provides cyclic or acyclic disubstituted 2'-O-aminooxyethyl analogs 154 as the phosphoramidites.

EXAMPLE 77

2'/3'-O(2-tert-butyldimethylsilylhydroxyethyl) adenosine (155 and 156)

Adenosine (10 g, 37.42 mmol) was dried over $P_2O_5$ under high vacuum. It was then suspended in anhydrous DMF (150 ML) and NaH (1.35 g, 56.13 mmol) was added. The reaction mixture was stirred at room temperature under inert atmosphere for 30 min. Then (2-bromo ethyl)-tert-butyldimethylsilane (9.68 mL, 4.4.90 mmol) was added dropwise and the reaction mixture stirred at room temperature overnight. DMF was removed under vacuum and to the residue dichloromethane (100 mL) was added and washed with water (2×80 mL). Dichloromethane layer was dried over anhydrous $Na_2SO_4$ and evaporated to dryness. Residue purified by column to get a mixture of products (4.30 g). Rf 0.49, 0.57 (10% MeOH in $CH_2Cl_2$)

EXAMPLE 78

2'-O-(2-methyleneiminooxyethyl)thymidine (157)

Compound 104 (3.10 g, 5.48 mmol) was dried over $P_2O_5$ under high vacuum. In a 100 mL round bottom flask, triethylamine-trihydroflouride (8.93 mL, 54.8 mmol) was dissolved in anhydrous THF and triethylamine (3.82 mL, 27.4 mmol) was added. The resulting solution was immediately added to the compound 104 and the reaction mixture was stirred at room temperature overnight. Solvent was removed under vacuum. Residue obtained was placed on a flash column and eluted with 10% MeOH in $CH_2Cl_2$ to yield 157 as white foam (1.35 g, 75% yield). Rf 0.45 (5% MeOH in $CH_2Cl_2$). MS (FAB$^\oplus$) m/e 330 (M+H$^\oplus$), 352 (M+Na$^\oplus$).

EXAMPLE 79

5'-O-dimethoxytrityl-2'-O-(2-methyleneiminooxyethyl)thymidine (158)

Compound 157 (0.64 g, 1.95 mmol) was dried over $P_2O_5$ under high vacuum overnight. It was then co-evaporated with anhydrous pyridine (5 mL). Residue dissolved in anhydrous pyridine (4.43 mL) and dimethoxytrityl chloride (0.79 g, 2.34 mmol), and 4-dimethylaminopyridine (23.8 mg, 0.2 mmol) was added. Reaction mixture was stirred under inert atmosphere at ambient temperature for 4 hrs. Solvent was removed under vacuum, the residue purified by column and eluted with 5% MeOH in $CH_2Cl_2$ containing a few drops of pyridine to yield 158 as a foam (1.09 g, 88% yield). Rf 0.4 (5% MeOH in $CH_2Cl_2$). MS (Electrospray⁻) m/e 630 (M–H$^\oplus$)

EXAMPLE 80

5'-O-dimethoxytrityl-2'-O-(2-methyleneiminooxyethyl)thymidine-3'-O-phosphoramidite (159)

Compound 158 (0.87 g, 1.34 mmol) was co-evaporated with toluene (10 mL). Residue was then mixed with diisopropylamine tetrazolide (0.23 g, 1.34 mmol) and dried over $P_2O_3$ under high vacuum overnight. It was then flushed with argon. Anhydrous acetonitrile (6.7 mL) was added to get a clear solution. To this solution 2-cyanoethyl tetraisopropylphosphorodiamidites (1.7 mL, 5.36 mmol) was added and the reaction mixture was stirred at room temperature for 6 hr. under inert atmosphere. Solvent was removed under vacuum, the residue was diluted with ethyl acetate (40 mL), and washed with 5% $NaHCO_3$ (20 mL) and brine (20 mL). Ethyl acetate layer was dried over anhydrous $Na_2SO_4$ and concentrated to dryness. Residue placed on a flash column and eluted with ethyl acetate:hexane (60:40) to yield 159 (1.92 g, 80% yield). Rf 0.34 (ethyl acetate:hexane, 60:40). $^{31}$P NMR (CDCl$_3$) δ150.76 ppm, MS (Electrospray⁻) m/e 830 (M–H$^\oplus$).

EXAMPLE 81

Attachment of Nucleoside to Solid Support General Procedure

Compound 107 (200 mg, 0.31 mmol) was mixed with DMAP (19 mg, 16 mmol), succinic anhydride (47 mg, 0.47 mmol), triethylamine (86 mL, 0.62 mmol) and dichloromethane (0.8 mL) and stirred for 4 hr. The mixture was diluted with $CH_2Cl_2$ (50 mL) and the $CH_2Cl_2$ layer was washed first with ice cold 10% aqueous citric acid and then with water. The organic phase was concentrated to dryness to yield 161. Residue (161) was dissolved in anhydrous acetonitrile (23 mL). To this DMAP (37 mg, 0.3 mmol), and 2',2'-dithiobis(5-nitropyridine) (103 mg, 0.33 mmol) were added. The solution was stirred for 5 min. To this was added triphenylphosphine (78.69 mg, 0.3 mmol) in anhydrous acetonitrile (3 mL). The solution was stirred for 10 min. and then CPG was added to it. The slurry was then shaken for 2 hr. It was then filtered, washed with acetonitrile and $CH_2Cl_2$. The functionalized CPG was dried and capped with capping solution to yield 161. Loading capacity was determined (58.3 μmol/g).

EXAMPLE 82

Synthesis of Aminooxy Derivatives: Alternative Procedure

The diol 162 is converted to its tosylate derivative 163 by treatment with 1 equivalent of p-toluenesulfonyl chloride-pyridine followed by standard work-up. The tosylate is subsequently treated with several amino-hydroxy compounds to act as nucleophiles in displacing tosylate to yield a series of oxy-amino compounds. The reaction is facilitated by preforming the anion from the amino alcohol or hydroxylamine derivative by the use of sodium hydride under anhydrous conditions.

EXAMPLE 83

General Procedure for the Preparation of DMAOE Oligonucleotides and Gapped Oligonucleotides A 0.1 m solution of each 2'-O-DMAOE amidite was prepared as a solution in anhydrous acetonitrile and loaded onto an Expedite Nucleic Acid synthesis system (Millipore) to synthesize oligonucleotides. All other amidites (A, T, C and G, PerSeptive Biosystem) used in synthesis also made as 0.1 M solution in anhydrous acetonitrile. All syntheses were carried out in the DMT on mode. For the coupling of the 2'-O-DMAOE amidites coupling time was extended to 10 minutes and this step was carried out twice. All other steps in the protocol supplied by Millipore were used except the extended oxidation time (240 seconds). 0.5 m solution of (S)-(+)-10-camphorsulfoyl)oxaziridine in anhydrous acetonitrile was used as oxidizer. Beaucage reagent was used for phosphorothioate synthesis. The overall coupling efficiencies were more than 90%. The oligonucleotides were cleaved from the controlled pore glass (CPG) supports and deprotected under standard conditions using concentrated aqueous $NH_4OH$ (30%) at 55° C. 5'-O-DMT containing oligomers were then purified by reverse phase liquid chromatography (C-4, Waters, 7–8×300 mm, A=50 mM triethylammonium acetate pH 1, B=100% $CH_3CN$, 5 to 60% B in 60 minutes). Detritylation with aqueous 80% acetic acid (1 ML, 30 min., room temperature), evaporations, followed by desalting by using sephadese G-25 column gave oligonucleotides as pure foams. All oligomers were then analyzed by CGE, HPLC and mass spectrometry.

DMAOE GAPMERS

| SEQ ID NO: | Sequence 5'–3' | Mass Exp. g/mol | Obs. g/mol | HPLC Retention time minutes | Target Target |
|---|---|---|---|---|---|
| 20 | T*T*C*T* C*GCCCG CTC* T*C*C*T*C*C* | 7440.68 | 7439.55 | 23.62 | c-raf |
| 19 | T*T*C*T* C*GCTGGT GAGT* T*T*C*A* | 7018.43 | 7017.69 | 23.90 | pkc-α |
| 20 | T*T*C*T*C*GCCCGC TCC*T*C*C*T*C*C* | 7600.68 | 7601.12 | 25.60 | c-raf |
| 19 | T*T*C*T*C*G CTGGT GAGT*T*T*C*A* | 7146.44 | 7146.44 | 25.91 | pkc-α |
| 20 | T*T*C*T*C*GCCCGC TCC*T*C*C*T*C*C* | 7543.30 | 7541.90 | 24.83 | c-raf |
| 19 | T*T*C*T*C*GCTGGT GAGT*T*T*C*A* | 7189.71 | 7188.41 | 25.28 | pkc-α |
| 20 | T*T*C*T*C*GCCCGCT CC*T*C*C*T*C*C* | 7383.30 | 7379.64 | 22.60 | c-raf |
| 19 | T*T*C*T*C*GCTGGTG AGT*T*T*C*A* | 7061.71 | 7059.70 | 23.02 | pkc-α | are modified as 2'-O-MOE and SEQ ID NoS., 19 and 20 are modified as 2'-O-DMAOE; underlined nucleotides are joined by phosphorothioate linkages and all other internucleotide linkages are phosphodiester; all C's are 5-methyl C; and separations were performed using the following HPLC conditions: C-4 column, Waters 3.9×300 m.m, A=50 mM TEAAc, B=$CH_3CN$, 5 to 60% in 60 min. Flow 1.5 ML/min., t=260 nm.

For the synthesis of the foregoing oligonucleotides, especially the MOE gapmers, as controls the following modified amidites were used: 2'-O-methoxyethyl-thymidine (RIC,Inc. lot # E1050-P-10), 2'-O-methoxyethyl-5-methylcytidine (lot # S1941/RS ), 2'-O-methoxyethyl-adenosine, and 5-methylcytidine (lot # 311094).

The required amounts of the amidites were placed in dried vials, dissolved in acetonitrile (unmodified nucleosides were made into 1M solutions and modified nucleosides were 100 mg/ML), and connected to the appropriate ports on a Millipore Expedite™ Nucleic Acid Synthesis System (ISIS 4). 30 mg of solid support resin was used in each column for 1 umole scale synthesis. The synthesis was run using the IBP-PS(1 umole)decoupling protocol for phosphorothioate backbones and CSO-8 for phosphodiesters. The trityl reports indicated normal coupling results.

After synthesis the oligonucleotides were deprotected with conc. ammonium hydroxide(aq) at 55° C. for approximately 16 hrs. Then they were evaporated, using a Savant AS160 Automatic SpeedVac, (to remove ammonia) and filtered to remove the CPG-resin.

The crude samples were analyzed by MS, HPLC, and CE. Then they were purified on a Waters 600E HPLC system with a 991 detector using a Waters C4 Prep. scale column (Alice C4 Prep. Oct. 16, 1996) and the following solvents: A: 50 mM TEA-Ac, pH 7.0 and B: acetonitrile utilizing the "MPREP2" method.

After purification the oligos were evaporated to dryness and then detritylated with 80% acetic acid at room temp. for approximately 30 min. Then they were evaporated.

The oligos were then dissolved in conc. ammonium hydroxide and run through a column containing Sephadex G-25 using water as the solvent and a Pharmacia LKB SuperFrac fraction collector. The resulting purified oligos were evaporated and analyzed by MS, CE, and HPLC.

EXAMPLE 83

General Procedure for the Preparation of DMAOE Oligonucleotides and Gapped Oligonucleotides A 0.1 m solution of each 2'-O-DMAOE amidite was prepared as a solution in anhydrous acetonitrile and loaded onto an Expedite Nucleic Acid synthesis system (Millipore) to synthesize oligonucleotides. All other amidites (A, T, C and G, PerSeptive Biosystem) used in synthesis also made as 0.1 M solution in anhydrous acetonitrile. All syntheses were carried out in the DMT on mode. For the coupling of the 2'-O-DMAOE amidites coupling time was extended to 10 minutes and this step was carried out twice. All other steps in the protocol supplied by Millipore were used except the extended oxidation time (240 seconds). 0.5 m solution of (S)-(+)-10-camphorsulfoyl)oxaziridine in anhydrous acetonitrile was used as oxidizer. Beaucage reagent was used for phosphorothioate synthesis. The overall coupling efficiencies were more than 90%. The oligonucleotides were cleaved from the controlled pore glass (CPG) supports and deprotected under standard conditions using concentrated aqueous $NH_4OH$ (30%) at 55° C. 5'-O-DMT containing oligomers were then purified by reverse phase liquid chromatography (C-4, Waters, 7–8×300 mm, A=50 mM triethylammonium acetate pH 1, B=100%$CH_3CN$, 5 to 60% B in 60 minutes). Detritylation with aqueous 80% acetic acid (1 ML, 30 min., room temperature), evaporations, followed by desalting by using sephadese G-25 column gave oligonucleotides as pure foams. All oligomers were then analyzed by CGE, HPLC and mass spectrometry.

DMAOE GAPMERS

| SEQ ID NO: | Sequence 5'–3' | Mass Exp. g/mol | Obs. g/mol | HPLC Retention time minutes | Target Target |
|---|---|---|---|---|---|
| 20a | T*T*C* T*C*G CCC GCT* CCT* C*C*T* C*C* | 7440.68 | 7439.55 | 23.62 | c-raf |
| 19a | T*T*C* T*C*G CTG GTG AGT* T*T*C* A* | 7018.43 | 7017.69 | 23.90 | pkc-α |
| 20a | $T_S$*$T_S$*$C_S$* $T_S$*$C_S$*G CCC GCT CC*$T_S$* $C_S$*$C_S$*$T_S$* $C_S$*$C$* | 7600.68 | 7601.12 | 25.60 | c-raf |

DMAOE GAPMERS

| SEQ ID NO: | Sequence 5'–3' | Mass Exp. g/mol | Mass Obs. g/mol | HPLC Retention time minutes | Target |
|---|---|---|---|---|---|
| 19a | $T_s*T_s*C_s*T_s*C_s*G$ CTG GTG AGT* T*T*C* A* | 7146.44 | 7146.44 | 25.91 | pkc-α |
| 20b | $T_s*T_s*C_s*T_s*C_s*G$ CCC GCT CC*$T_s*$ $C_s*C_s*T_s*C_s*C*$ | 7543.30 | 7541.90 | 24.83 | c-raf |
| 19b | $T_s*T_s*C_s*T_s*C_s*G$ CTG GTG $AGT_s*$ $T_s*T_s*C_s*A_s*$ | 7189.71 | 7188.41 | 25.28 | pkc-α |
| 20b | T*T*C* T*C*G CCC GCT CC*T* C*C*T* C*C* | 7383.30 | 7379.64 | 22.60 | c-raf |
| 19b | T*T*C* T*C*G CTG GTG AGT* T*T*C* A* | 7061.71 | 7059.70 | 23.02 | pkc-α | modified as 2'-O-MOE and 19b and 20b are modified as 2'-O-DMAOE; subscript s indicates a phosphorothioate internucleoside linkage and all other internucleotide linkages are phosphodiester; all C's are 5-methyl C; and separations were performed using the following HPLC conditions: C-4 column, Waters 3.9×300 m.m, A=50 mM TEAAc, B=$CH_3CN$, 5 to 60% in 60 min. Flow 1.5 ML/min., t=260 nm.

For the synthesis of the foregoing oligonucleotides, especially the MOE gapmers, as controls the following modified amidites were used: 2'-O-methoxyethyl-thymidine (RIC,Inc. lot # E1050-P-10), 2'-O-methoxyethyl-5-methylcytidine (lot # S1941/RS), 2'-O-methoxyethyl-adenosine, and 5-methylcytidine (lot # 311094).

The required amounts of the amidites were placed in dried vials, dissolved in acetonitrile (unmodified nucleosides were made into 1M solutions and modified nucleosides were 100 mg/ML), and connected to the appropriate ports on a Millipore Expedite™ Nucleic Acid Synthesis System (ISIS 4). 30 mg of solid support resin was used in each column for 1 umole scale synthesis. The synthesis was run using the IBP-PS(1 umole)decoupling protocol for phosphorothioate backbones and CSO-8 for phosphodiesters. The trityl reports indicated normal coupling results.

After synthesis the oligonucleotides were deprotected with conc. ammonium hydroxide(aq) at 55° C. for approximately 16 hrs. Then they were evaporated, using a Savant AS160 Automatic SpeedVac, (to remove ammonia) and filtered to remove the CPG-resin.

The crude samples were analyzed by MS, HPLC, and CE. Then they were purified on a Waters 600E HPLC system with a 991 detector using a Waters C4 Prep. scale column (Alice C4 Prep. Oct. 16, 1996) and the following solvents: A: 50 mM TEA-Ac, pH 7.0 and B: acetonitrile utilizing the "MPREP2" method.

After purification the oligos were evaporated to dryness and then detritylated with 80% acetic acid at room temp. for approximately 30 min. Then they were evaporated.

The oligos were then dissolved in conc. ammonium hydroxide and run through a column containing Sephadex G-25 using water as the solvent and a Pharmacia LKB SuperFrac fraction collector. The resulting purified oligos were evaporated and analyzed by MS, CE, and HPLC. These oligomers are the 2'-DMAOE thioate and diester analogs of SEQ ID NOs. 19 and 20.

| SEQ ID NO: | Mass (g/mol) Observed | Mass (g/mol) Observed | |
|---|---|---|---|
| 20 | 7240.929 | 7239.91 | (P = S wings) |
| 19 | 6887.341 | 6882.51 | (P = S wings) |
| 20 | 7080.929 | 7076.04 | (P = O wings) |
| 19 | 6759.341 | 6756.51 | (P = O wings) |

EXAMPLE 84

General Procedure for the Preparation of Uniformly Modified DMAOE Oligonucleotides 2-O-DMAOE amidites of A (225 mg, 0.23 mmol), $^{5me}C$ (150 mg, 0.16 mmol), G (300 mg, 0.31 mmol) and T (169.4 mg, 0.2 mmol) were dissolved in anhydous acetonitrile to get 0.1 M solutions. These solutions were loaded onto a Expedite Nucleic Acid Synthesis system (Millipore) to synthesize the oligonucleotides. The coupling efficiencies were more than 90%. For the coupling of the amidite 1 coupling time was extended to 10 minutes and this step was carried out twice. All other steps in the protocol supplied by Millipore were used except the extended coupling time. Because reagent (0.1 M in acetonitrile) was used as a sulferizing agent. For diester synthesis, CSO was used as the oxidizing agent.

The oligomers were cleaved from the controlled pore glass(CPG) supports and deprotected under standard conditions using concentrated aqueous $NH_4OH$ (30%) at 55 ° C. 5'-O-DMT containing oligomers were then purified by reverse phase high performance liquid chromatography (C-4, Waters, 7.8×300 mm, A=50 mM triethylammonium acetate, pH −7, B=acetonitrile, 5–60% of B in 60 min., flow 1.5 ML/min.). Detritylation with aqueous 80% acetic acid and evaporation, followed by desalting in a Sephadex G-25 column gave oligonucleotides 28059, 28060 and 22786. Oligonucleotides were analyzed by HPLC, CGE and Mass spectrometry.

| SEQ ID #/ min. | Sequence | Target | Mass expected/ Observed | HPLC retention time |
|---|---|---|---|---|
| 18 | 5-T*sC*sT*sG*sA*sG*s T*sA*sG*sC*sA*sG*sA*s G*sG*sA*sG*sC*sT*sC*-3' | ICAM | 8602.67/ 8607.74 | 31.96 |
| 18 | 5'-T*C*T*G*A*G*T*A*G*C* A*G*A*G*G*A*G*C*T*C*-3' 5'-GCGTAT*ACG-3' | ICAM | 8298.66/ 8301.38 3131.35/ 3130.25 | 28.44 21.87 @ |

HPLC Conditions C-18, Waters 3.9×300 mm, A=50 mM triethyammonium acetate, pH 7; B=Acetonitrile; 5 to 60% B in 55 min.; flow 1 ML/min., @ 5 to 18% B in 30 min.; flow 1.5 ML/min., T*=2'-O-DMAOE T, A*=2'-O-DMAOE A, C*=2'-O-DMAOE $^{5me}$C, G*=2'-O-DMAOE G.

EXAMPLE 85

$O^2$,2'-anhydro[1-(β-D-arabinofuranosyl)-5-methyluridine]

5-Methyluridine (ribosylthymine, commercially available through Yamasa, Choshi, Japan) (72.0, 0.279 mol), diphenylcarbonate (90.0, 0.420 mol) and sodium bicarbonate (2.0 g, 0.024 mol) were added to dimethylformamide (300 ML). The mixture was heated to reflux with stirring allowing the resulting carbon dioxide gas to evolve in a controlled manner. After 1 hour, the slightly darkened solution was concentrated under reduced pressure. The resulting syrup was poured into stirred diethyl ether (2.5 L). The product formed a gum. The ether was decanted and the residue was dissolved in a minimum amount of methanol (ca 400 Ml). The solution was poured into fresh ether as above (2.5 L) to give a stiff gum. The ether was decanted and the gum was dried in a vacuum oven (60° C. at 1 mm Hg for 24 h) to give a solid which was crushed to a light tan powder (57 g, 85% crude yield). NMR was consistent with structure and contamination with phenol and its sodium salt (ca 5%). The material was used as is for ring opening. It can be purified further by column chromatography using a gradient of methanol in ethyl acetate (10–25%) to give a white solid, mp 222–4° C.

EXAMPLE 86

5'-O-tert-Butyldiphenylsilyl-$O^2$-2'-anhydro-5-methyl uridine (1a)

$O^2$,2'-Anhydro-5-methyluridine (100.0 g, 0.416 mmol) and dimethylaminopyridine (0.66 g, 0.013 eq, 0.0054 mmol) were dissolved in dry pyridine (500 ML) at ambient temperature under an argon atmosphere and with mechanical stirring. Tert-butyldiphenylchlorosilane (125.8 g, 119.0 ML, 1.1 eq, 0.458 mmol) was added in one portion and the reaction was stirred for 16 h at ambient temperature. TLC (Rf 0.22, ethyl acetate) indicated a complete reaction. The solution was concentrated under reduced pressure to a thick oil which was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 ML) and the solution was cooled to −10° C. The resulting crystalline product was collected by filtration, washed with ethyl ether (3×200 ML) and dried (40° C., 1 mm Hg, 24 h) to give 149g (74.8%) of the title compound as a white solid. TLC and NMR were consistent with pure product.

EXAMPLE 87

5'-O-tert-Butyldiphenylsilyl-2'-O-(2-hydroxyethyl)-5-methyl uridine (2a)

Borane in THF (1.0 M, 2.0 eq, 622 ML) was added to a 2 L stainless steel, unstirred pressure reactor. In the fume hood and with manual stirring, ethylene glycol (350 ML, excess) was added cautiously at first until the evolution of hydrogen gas subsided. 5'-O-Tert-butyldiphenylsilyl-$O^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure <100 psig). The reaction vessel was cooled to ambient temperature and opened. TLC ($R_f$ 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water with the product in the organic phase.] The residue was purified by column chromatography (2 kg silica gel, ethyl acetate:hexanes gradient from 1:1 to 4:1). The appropriate fractions were combined, concentrated and dried to give 84 g (50%) of the title compound as a white crisp foam. Also collected from the column was contaminated starting material (17.4 g) and pure reusable starting material (20 g). The yield, based on starting material less pure recovered starting material, was 58%. TLC and NMR were consistent with the title compound at a purity of 99%.

$^1$H NMR (DMSO-$d_6$) d 1.05 (s, 9H), 1.45 (s, 3 H), 3.5–4.1 (m, 8 H), 4.25 (m, 1 H), 4.80 (t, 1 H), 5.18 (d, 2H), 5.95 (d, 1 H), 7.35–7.75 (m, 11 H), 11.42 (s, 1 H).

EXAMPLE 88

2'-O-[2-(phthalimidoxy)ethyl]-5'-tert-butyldiphenylsilyl-5-methyl uridine (3a)

Nucleoside 2a (20 g, 36.98 mmol) was mixed with triphenylphosphine (11.63 g, 44.36 mmol) and N-hydroxyphthalimide (7.24 g, 44.36 mmol). It was then dried over $P_2O_5$ in vacuo for two days at 40° C. The reaction mixture was flushed with argon and dry THF (369.8 ML) was added to give a clear solution. Diethyl azodicarboxylate (6.98 ML, 44.36 mmol) was added dropwise to the reaction mixture. The rate of addition was maintained such that the resulting deep red coloration is just discharged before adding the next drop. After the addition was complete, the reaction was stirred for 4 hrs. The TLC showed the completion of the reaction (ethyl acetate:hexane, 60:40). The solvent was evaporated in vacuo and the resulting residue was purified by flash column chromatography using ethyl acetate:hexane (60:40) as the eluent to give 21.81 g (86%) of the title compound as a white foam. TLC $R_f$ 0.56 (ethyl acetate:hexane, 60:40). MS (FAB$^-$) m/z 684 (M−H$^+$)

EXAMPLE 89

5'-O-tert-butyldiphenylsilyl-2'-O-[2-(formaldoximinooxy)ethyl]-5-methyl uridine (4a)

Methylhydrazine (300 ML, 4.64 mmol) was added dropwise at from −10° C. to 0C to Compound 3a (3.1 g, 4.5 mmol) dissolved in dry $CH_2Cl_2$ (4.5 ML). After 1 hour the mixture was filtered, the filtrate was washed with ice cold $CH_2Cl_2$ and the combined organic phase was washed with water, brine and dried over anhydrous $Na_2SO_4$. The solution was concentrated to give 2'-O-(aminooxyethyl) thymidine, which was dissolved in MeOH (67.5 ML). Formaldehyde (20% aqueous solution, w/w, 1.1 eg.) was added and the mixture was stirred at room temperature for 1 h. The solvent was removed in vacuo and the residue purified by column chromatography to give 1.95 g (78%) of the title compound as a white foam.

$R_f$ 0.32 (5% MeOH in $CH_2Cl_2$). $^1H$ NMR (200 MHZ, DMSO-$d_6$) δ1.03 (s, 9H), 1.45 (s, 3H) 3.66–4.03 (m, 9H), 5.20 (d, 1H, J=5.92 Hz), 5.91 (d, 1H, J=5.42 Hz), 6.54 (d, 1H, J=7.7 Hz), 6.99 (d, 1H, 7.64 Hz), 7.39–7.48 (m, 6H), 7.61–7.67 (m, 4H), 11.39 (s, 1H); $^{13}C$ NMR (50 MHZ, $CDCl_3$) 11.84, 19.41, 62.96, 68.57, 70.02, 72.61, 82.67, 84.33, 87.14, 111.12, 127.90, 129.98, 132.37, 133.10, 134.93, 135.18, 135.44, 137.96, 150.50, 164.02; MS (Electrospray) m/z 566 (M–H).

EXAMPLE 90

5'-O-tert-Butyldiphenylsilyl-2'-O-[2-(N-methyl) aminooxyethyl]-5-methyl uridine (5a)

Compound 4a (2.3 g, 4.17 mmol) was dissolved in 1M pyridinium-p-toluenesulfonate in MeOH (41.7 ML). The reaction mixture was cooled to 10° C. on an ice bath and $NaBH_3CN$ (0.52 g, 8.35) was added with continued cooling and stirring for 15 minutes. The mixture was allowed to warm to room temperature and stirred for 4 hours. The progress of the reaction was complete as indicated by TLC (5% MeOH in $CH_2Cl_2$). The mixture was concentrated to a syrup and diluted with ethyl acetate (50 ML) and washed with water (30 ML), 5% aqueous $NaHCO_3$ (30 ML) and brine (30 ML). The ethyl acetate layer was dried over anhydrous $Na_2SO_4$ and evaporated to dryness to give 2.32 g of the title compound as a foam. The foam was used for the next step without further purification. $R_f$ (0.34, 5% MeOH in $CH_2Cl_2$).

EXAMPLE 91

5'-O-tert-Butyldiphenylsilyl-2'-O-{2-[(N-methyl)-N-(2-phthalimido)ethyl]aminooxy ethyl}-5-methyl uridine (6a)

Compound 5a (2 g, 3.44 mmol) was dissolved in 1M pyridinium p-toulene sulfonate in MeOH (34 ML). α-Phthalimidoacetaldehyde (0.72 g, 3.78 mmol) was added and the mixture was stirred at ambient temperature for 10 minutes. The reaction mixture was cooled to 10° C. in an ice bath and $NaBH_3CN$ (0.43 g, 0.89 mmol) was added with stirring at 10 ° C. for 15 minutes. The reaction mixture was allowed to warm to room temperature, stirred for 4 hours, concentrated to an oil and diluted with ethyl acetate (50 ML). The ethyl acetate layer was washed with water (40 ML), 5% $NaHCO_3$ (40 ML) and brine (25 ML). The organic phase was dried over anhydrous $Na_2SO_4$ and evaporated to dryness. The residue was purified by flash column chromatography and eluted with ethyl acetate:hexane 60:40 to give 1.54 g (60%) of the title compound.

$R_f$=0.68 (Ethyl acetate). $^1H$ NMR (200 MHZ, DMSO-$d_6$) δ1.04 (s, 9H), 1.41 (s, 3H), 2.46 (s, 3H), 2.79 (t, 2H, J=6.34 Hz), 3.69–4.08 (m, 10H), 4.27 (m, 1H), 5.22 (d, 1H, J=5.7 MHZ), 5.95 (d, 1H, J=5.86 Hz), 7.39–7.7 (m, 11H), 7.84 (s, 4H), 11.38 (s, 1H); HRMS (MALDI) Calcd for $C_{39}H_{46}O_9N_4SiNa^+$ 765.2932, Found: 765.2922.

EXAMPLE 92

2'-O-{2-[(N-methyl)-N-(2-phthalimido)ethyl] aminooxyethyl}-5-methyl uridine (7a)

A solution of triethylamine trihydrogen fluoride (2.64 ML, 16.2 mmol) and triethylamine (1.13 ML, 8.1 mol) in THF was added to compound 6a (1.2 g, 1.62 mmol) with stirring at room temperature for 18 hours. TLC indicated that the reaction was completed at this time (10% MeOH in $CH_2Cl_2$) The solvent was removed in vacuo, the residue dissolved in ethyl acetate (30 ML), the organic layer washed with water (30 ML), brine (30 ML) and dried over anhydrous $Na_2SO_4$. The organic phase was evaporated and the residue purified by flash chromatography using 5% MeOH in $CH_2Cl_2$ as eluent to give 0.42 g (52%) of the title compound as a solid.

($R_f$=0.34, 10% MeOH in $CH_2Cl_2$) $^1H$ NMR (200 MHZ, DMSO-$d_6$) δ1.70 (s, 3H), 2.46 (s, 3H), 2.78 (t, 2H, J=6.35 Hz), 3.54–3.74 (m, 8H), 3.8 (d, 1H, J=3.52 Hz), 3.97 (t, 1H, J=5.26 Hz), 4.10 (q, 1H, J=4.98 Hz), 5.05 (d, 1H, J=5.58 Hz), 5.12 (t, 1H, J=5.14 Hz), 5.86 (d, 1H, J=5.64 Hz), 7.75 (s, 1H), 7.84 (s, 4H), 11.29 (s, 1H); $^{13}C$ (50 MHZ, $CDCl_3$) 12.37, 35.55, 45.62, 58.05, 61.58, 69.06, 69.97, 70.98, 81.39, 85.2, 90.7, 110.67, 123.17, 132.01, 133.94, 138.05, 150.49, 164.24, 168.47; HRMS (FAB) Calcd for $C_{23}H_{29}O_9N_4^Å$ 505.1927; Found: 505.1927.

EXAMPLE 93

5'-O-DMT-2'-O-{2-[N-(methyl)-N-(2-phthalimido) ethyl]aminooxyethyl}-5-methyl uridine (8a)

Compound 7a (0.4 g, 0.79 mmol), dried over $P_2O_5$ at 40° C. in vacuo overnight, was mixed with DMAP (0.019 g, 0.16 mmol) and co-evaporated with pyridine (3 ML). The residue was dissolved in anhydrous pyridine (1.9 ML) and DMTCl (0.29 g, 0.87 mmol) was added. The reaction mixture was stirred at room temperature under inert atmosphere for 8 hours with monitoring by TLC (5% MeOH in $CH_2Cl_2$). Additional DMTCl (0.15 mg) was added with stirring continued until disappearance of the starting material. Pyridine was removed in vacuo and the residue was purified by flash column chromatography using ethyl acetate:hexane 60:40 as the eluent to give 0.47 g (73%) of the title compound.

($R_f$=0.35, 5% MeOH in $CH_2Cl_2$). $^1H$ NMR (200 MHZ, DMSO-$d_6$) δ1.36 (s, 3H), 2.48 (s, 3H), 2.79 (t, 2H, J=6.34 Hz), 3.21 (m, 2H), 3.73 (brs, 12H), 3.97 (m, 1H), 4.07 (m 1H), 4.22 (m, 1H), 5.16 (d, 1H, J=6.12 Hz), 5.87 (d, 1H, J=4.94 Hz), 6.89 (d, 3H, J=4H), 7.34–7.43 (m, 9H), 7.48 (s,1H), 7.83 (s, 4H), 11.36 (s, 1H); $^{13}C$ (50 MHZ, $CDCl_3$), 11.59, 35.36, 45.5, 54.83, 57.94, 61.96, 68.85, 69.86, 82.6, 83.15, 86.47, 87.34, 110.53, 112.99, 122.56, 125.80, 127.72, 127.96, 129.8, 131.82, 133.63, 135.27, 135.83, 144.18, 150.44, 158.33, 164.28, 168.21; HRMS (FAB) Calcd for $C_{44}H_{46}O_{11}N_4Na^Å$ 829.3061, Found 829.3066.

EXAMPLE 94

5'-O-DMT-2'-O-{2-[N-(methyl)-N-(2-phthalimido) ethyl]aminooxyethyl}-5-methyl-uridine-3'-O-[(2-cyanoethyl)-N,N-diisopropyl)-phosphoramidite (9a)

N,N-Diisopropylamine tetrazolide (0.055 g, 0.32 mmol, dried over $P_2O_5$ in vacuo at 40° C. overnight) was added to Compound 8a (0.26 g, 0.32 mmol, co-evaporated with toulene) followed by anhydrous acetonitrile (1.6 ML) with stirring at room temperature for 18 hours under an inert atmosphere. Analysis by TLC (ethylacetate:hexane 60:40) showed the reaction was completed at this time. The solvent was remove in vacuo and the residue was purified by flash column chromatography using ethyl acetate containing 0.5% of pyridine as the eluent to give 0.28 g (85%) of the title compound.

($R_f$=0.28, ethylacetate:hexane, 60:40). $^{31}P$ NMR (80 MHZ, $CDCl_3$) δ150.82, 150.61; MS (FAB) m/z 1029 $[M+Na]^Å$.

EXAMPLE 95

5'-O-DMT-2'-O-{2-[N-(methyl)-N-(2-phthalimido) ethyl]aminooxyethyl}-3'-O-[(2-succinyl-5-methyl uridine (10a)

Compound 8a (0.16 g, 0.2 mmol) was mixed with DMAP (0.013 g, 0.10 mmol) and succinic anhydride (0.03 g, 0.3 mmol) and dried over $P_2O_5$ in vacuo at 40° C. overnight. $CH_2Cl_2$ (0.5 ML) and triethylamine (0.06 ML, 0.4 mmol) was added with stirring at room temperature for 4 hours under an inert atmosphere. The mixture was diluted with $CH_2Cl_2$ (30 ML) and washed with 10% aqueous citric acid (30 ML) and water (2×15 ML). The organic layer was dried over anhydrous $Na_2SO_4$ and concentrated to give 0.162 g (90%) of the title compound as a foam.

($R_f$=0.43, 10% MeOH in $CH_2Cl_2$). $^1$H NMR (200 MHZ, DMSO-$d_6$) δ1.4 (s, 3H), 2.42 (s, 3H), 2.56 (m, 4H, overlap with DMSO peak), 2.75 (t, 2H, J=6.29 Hz), 3.24 (m, 2H, overlapping with $H_2O$ peak), 3.53–3.8 (m, 6H), 3.72 (s, 6H), 4.13 (brs, 1H), 4.37 (t, 1H, J=5.86 Hz), 5.29 (t, 1H, J=4.4 Hz), 5.87 (d, 1H, J=6.36 Hz), 6.89 (d, 4H, J=8.72 Hz), 7.21–7.39 (m, 9H), 7.49 (s, 1H), 7.82 (s, 4H), 11.42 (s, 1H), 12.24 (brs, 1H); MS (FAB) m/z 929 [M+Na]$^A$.

EXAMPLE 96

5'-O-DMT-2'-O-{2-[N-(methyl)-N-(2-phthalimido) ethyl]aminooxyethyl]-5-methyl-uridine-3'-O-succinyl CPG (11a)

Compound 10a (0.15 g, 0.17 mmol) and DMAP (0.021 g, 0.17 mmol) was dissolved in anhydrous acetonitrile. To protect the reaction mixture from moisture 2,2'-dithiobis(5-nitropyridine) (0.068 g, 0.19 mg) was added. The solution was stirred for 5 minutes at room temperature. To this solution triphenyl phosphine (0.045 g, 0.17 mmol) in anhydrous acetonitrile (1.12 ML) was added. The solution was stirred for 10 minutes at ambient temperature. Activated CPG (Controlled Pore Glass, 1.12 g, 115.2 mmol/g, particle size 120/200, mean pore diameter 520 Å) was added and allowed to shake on a shaker for 2 hours. An aliquot was withdrawn and loading capacity was determined by following standard procedure (61.52 mmol/g). The functionalized CPG (11a) was filtered and washed throughly with $CH_3CN$, $CH_2Cl_2$ and $Et_2O$. It was then dried in vacuo over night. Any unreacted sites on the CPG was capped by using capping reagents [CapA (2 ML), acetic anhydride/leuticle/THF; Cap B (2 ML), 1-methylimidazole/THF, PerSeptive Biosystems Inc.] and allowed to shake on a shaker for 2 h. The functionalized CPG was filtered, washed thoroughly with $CH_3CN$, $CH_2Cl_2$ and $Et_2O$. It was then dried and the final loading capacity was determined (60.74 mmol/g).

EXAMPLE 97

5'-O-DMT-2'-O-{2-[(N,N-bis-2-phthalimidoethyl) aminooxy]ethyl}-5-methyl uridine-3'-O-[(2-cyanoethyl)N,N-diisopropyl] phosphoramidite (12a)

Compound 4a is treated with methylhydrazine to give the aminooxy compound followed by treatment with phtalimidoacetaldehyde to give the corresponding oxime. The oxime is reduced under acid catalyzed reductive amination conditions to give the 2-phtalimidoethyl derivative which on treatment with another equivalent of phtalimidoacetaldehyde under reductive amination conditions will give the bis(2-phtalimidoethyl)aminooxyethyl derivative. The bis (2-phthalimidoethyl)aminooxyethyl derivative is desilylated, tritylated at 5'-position and then 3'-phosphitylated to give the title compound.

EXAMPLE 98

5'-O-DMT-2'-O-{2-[(N,N-bis-2-phthalimidoethyl) aminooxy]ethyl}-5-methyl uridine-3'-O-succinyl CPG (13a)

Compound 14a is synthesized according to the procedure described for compounds 11a and 12a starting from 5'-O-DMT-2'-O-{2-[N,N-bis-(2-phthalimido)ethylaminooxy] ethyl}-5-methyl uridine.

EXAMPLE 99

Synthesis of oligonucleotides containing 2'-O-{2-[N-(2-amino)ethyl-N-(methyl)]aminooxyethyl} modification Phosphoramidite 9a was dissolved in anhydrous acetonitrile (0.1 M solution) and loaded on to a Expedite Nucleic Acid Synthesis system (Millipore 8909) for use in oligonucleotide synthesis. The coupling efficiencies were determined to be greater than 98%. For the coupling of the modified phosphoramidite 9a coupling time was extended to 10 minutes and this step was carried out twice. All other steps in the protocol supplied by Millipore were used without modification. After completion of the synthesis CPG was suspended in aqueous ammonia solution (30 wt %) containing 10% methyl amine (40 wt % solution) and heated at 55° C. for 6 h. The resulting oligonucleotides were purified by HPLC (Waters, C-4, 7.8×300 mm, A=50 mM triethylammonium acetate, pH=7, B acetonitrile, 5 to 60% B in 55 Min, Flow 2.5 ML/min., λ=260 nm). Detritylation with aqueous 80% acetic acid and evaporation followed by desalting by HPLC on Waters C-4 column gave 2'-modified oligonucleotides (Table I). Oligonucleotides were analyzed by HPLC, CGE and mass spectrometry.

TABLE I

Oligonucleotides containing 2'-O-{2-[N-(2-amino)ethyl-N-(methyl)] aminooxyethyl} modification

| SEQ ID No./ ISIS # | Sequence | Mass Calcd | Mass Found | HPLC Retention Time (min.$^a$) |
|---|---|---|---|---|
| 6/ 30443 | 5' CTC GTA CT*T* T*T*C CGG TCC 3' | 5919.21 | 5919.79 | 23.79$^a$ |
| 14/ 26267 | 5' TTT TTT TTT TTT TTT T*T*T* T* 3' | 6246.45 | 6243.04 | 25.56$^b$ |

T* = 2'-O-{2-[N-(2-amino)ethyl-(N-methyl)aminooxy]ethyl} $^{5Me}$U 7.8×300 mm, solvent A=50 mm TEAAc, pH 7; Solvent B=$CH_3CN$; gradient 5–60% B in 50 min; flow rate 2.5 ML/min, 1=260 nm, 3.9×300 mm, solvent A=50 mm TEAAC, pH 7; Solvent B=$CH_3CN$; gradient 5–40% B in 55 min; flow rate 1.5 ML/min, 1=260 nm.

TABLE II

Tm values of 2'-O-{2-[N-(2-amino)ethyl-(N-methyl)aminooxy]ethyl} modifications

| SEQ ID No./ ISIS # | Sequence 5'–3' | Tm ° C. Target RNA | ΔTm ° C. | ΔTm/mod ° C. |
|---|---|---|---|---|
| 6/ 2896 | CTC GTA CTT TTC CGG TCC | 61.8 | | |
| 6/ 32350 | CTC GTA CT*T* T*T*C CGG TCC | 63.60 | 1.8 | 0.38 |

T* = 2'-O-{2-[N-(2-amino)ethyl-N-(methyl)aminooxy]ethyl} $^{5Me}$U

EXAMPLE 100

5'-O-DMT-2'-O-{2-[N-2-(N,N-dimethylamino)ethyl-N-(methyl)aminooxy]ethyl}-5-methyluridine-3'-O-[(2-cyanoethyl)N,N-diisopropyl] phosphoramidite (14a)

Compound 14a is synthesized from compound 3a. The phthalimido compound 3a is deprotected with methylhydrazine to form the aminooxy compound. The reactive aminooxy compound is treated with α-(N,N-dimethylamino) acetaldehyde diethyl acetal to give the corresponding oxime. The oxime is reduced under acid catalyzed reductive amination conditions to give the 2-{[2-N,N-(dimethyl)amino]ethylaminooxy}ethyl derivative which on treatment with formaldehyde under reductive amination condition gives the 2-{[N-2-(N,N-dimethyl)amino]ethyl-N-(methyl)aminooxy}ethyl derivative. Desilylation, tritylation and phosphitylation as illustrated in previous examples gives the title phosphoramidite.

Compound 101

5'-O-DMT-2'-O-{2-[N-2-(N,N-dimethylamino)ethyl-N-(methyl)-aminooxy]ethyl}-5-methyl uridine-3'-O-succinyl CPG (15a)

Compound 15a is synthesized according to the procedure described for compounds 11a and 12a starting from 5'-O-DMT-2'-O-{2-[N-(2-N,N-dimethylamino)ethyl-N-(methyl)aminooxy]ethyl}-5-methyl uridine.

Procedure 1
Nuclease Resistance

A. Evaluation of the resistance of modified oligonucleotides to serum and cytoplasmic nucleases.

Oligonucleotides including the modified oligonucleotides of the invention can be assessed for their resistance to serum nucleases by incubation of the oligonucleotides in media containing various concentrations of fetal calf serum or adult human serum. Labeled oligonucleotides are incubated for various times, treated with protease K and then analyzed by gel electrophoresis on 20% polyacrylamide-urea denaturing gels and subsequent autoradiography. Autoradiograms are quantitated by laser densitometry. Based upon the location of the modifications and the known length of the oligonucleotide it is possible to determine the effect on nuclease degradation by the particular modification. For the cytoplasmic nucleases, a HL60 cell line is used. A post-mitochondrial supernatant is prepared by differential centrifugation and the labeled oligonucleotides are incubated in this supernatant for various times. Following the incubation, oligonucleotides are assessed for degradation as outlined above for serum nucleolytic degradation. Autoradiography results are quantitated for comparison of the unmodified and modified oligonucleotides. As a control, unsubstituted phosphodiester oligonucleotide have been found to be 50% degraded within 1 hour, and 100% degraded within 20 hours.

B. Evaluation of the resistance of modified oligonucleotides to specific endo- and exonucleases.

Evaluation of the resistance of natural and modified oligonucleotides to specific nucleases (i.e., endonucleases, 3',5'-exo-, and 5',3'-exonucleases) is done to determine the exact effect of the modifications on degradation. Modified oligonucleotides are incubated in defined reaction buffers specific for various selected nucleases. Following treatment of the products with protease K, urea is added and analysis on 20% polyacrylamide gels containing urea is done. Gel products were visualized by staining using Stains All (Sigma Chemical Co.). Laser densitometry is used to quantitate the extend of degradation. The effects of the modifications are determined for specific nucleases and compared with the results obtained from the serum and cytoplasmic systems.

Nuclease resistance of oligonucleotides containing novel 2'-modifications

| SEQ. ID NO: 14 Series I | | |
|---|---|---|
| 5'TTT TTT TTT TTT TTT*T*T*T* T 3' | | |
| SEQ ID NO 14 | where T* = 5 methyl, 2'-aminooxyethoxy | 2' AOE |
| SEQ ID NO 14 | where T* = 5 methyl, 2'-dimethylaminooxyethoxy | 2' DMAOE |

Figure 14:
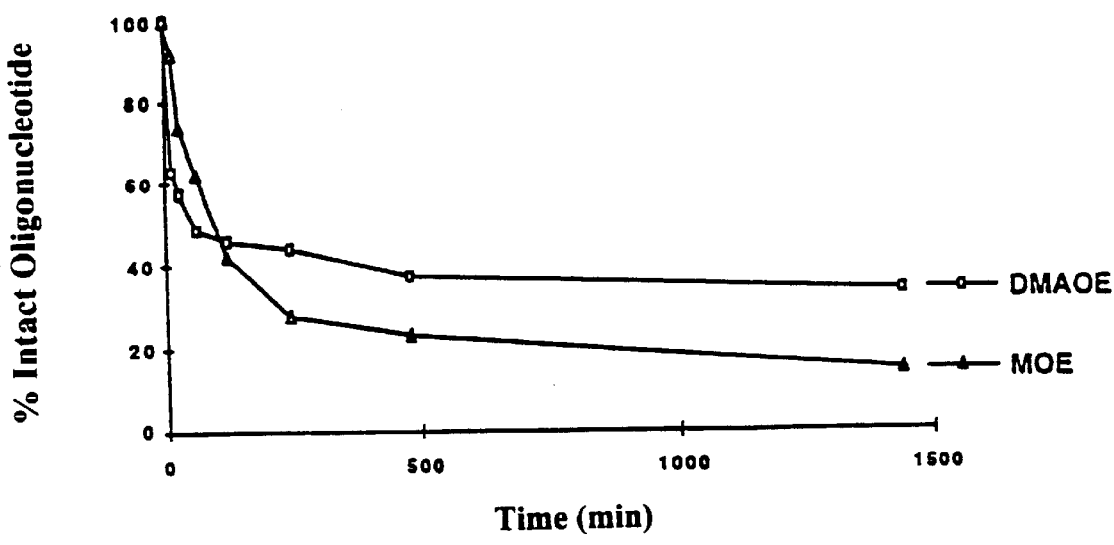
FIG. 14 shows a graph of % full length oligonucleotide versus time in minutes pertaining to effects of nuclease action on oligonucleotides.
Figure 15:
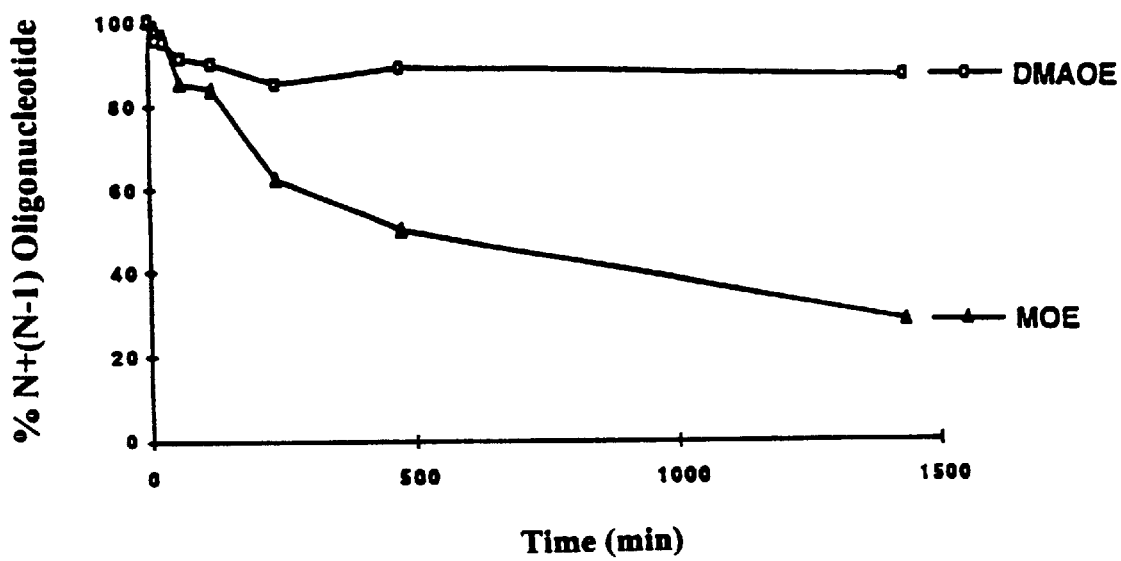
FIG. 15 shows a graph of % full length oligonucleotide versus time in minutes pertaining to effects of nuclease action on oligonucleotides.
Figure 16:
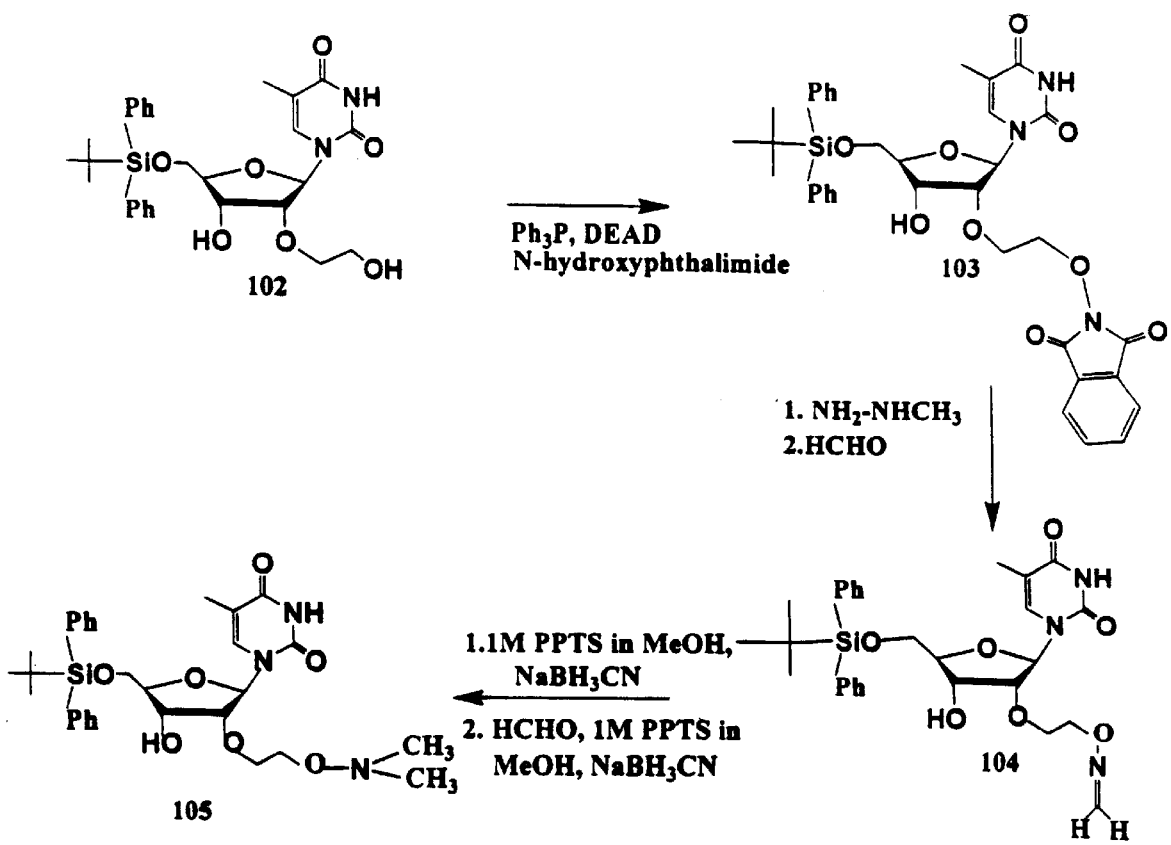
FIG. 16 shows a synthesis of intermediates and monomers of the invention.
Figure 17:
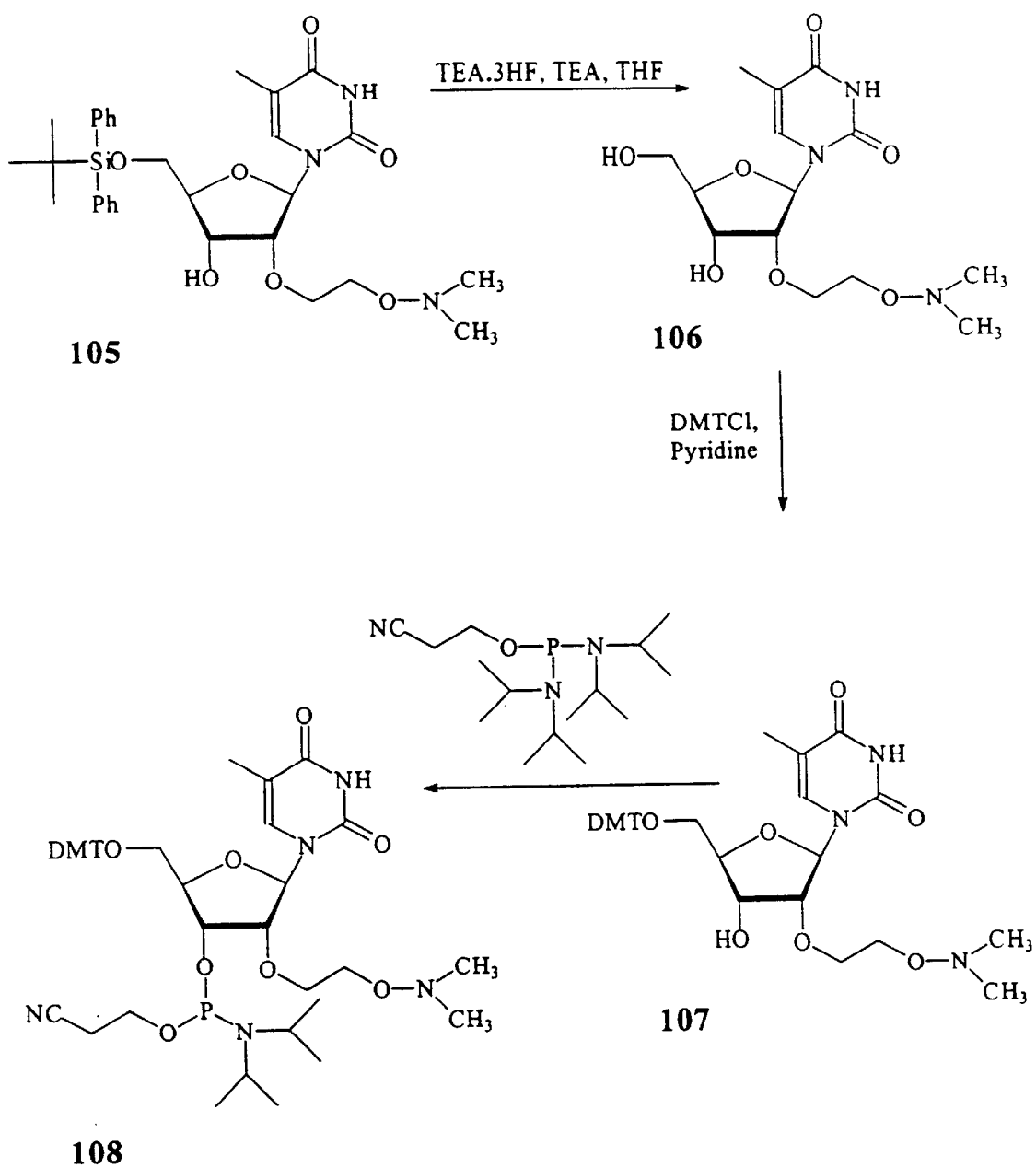
FIG. 17 shows a synthesis of intermediates and monomers of the invention.
Figure 18:
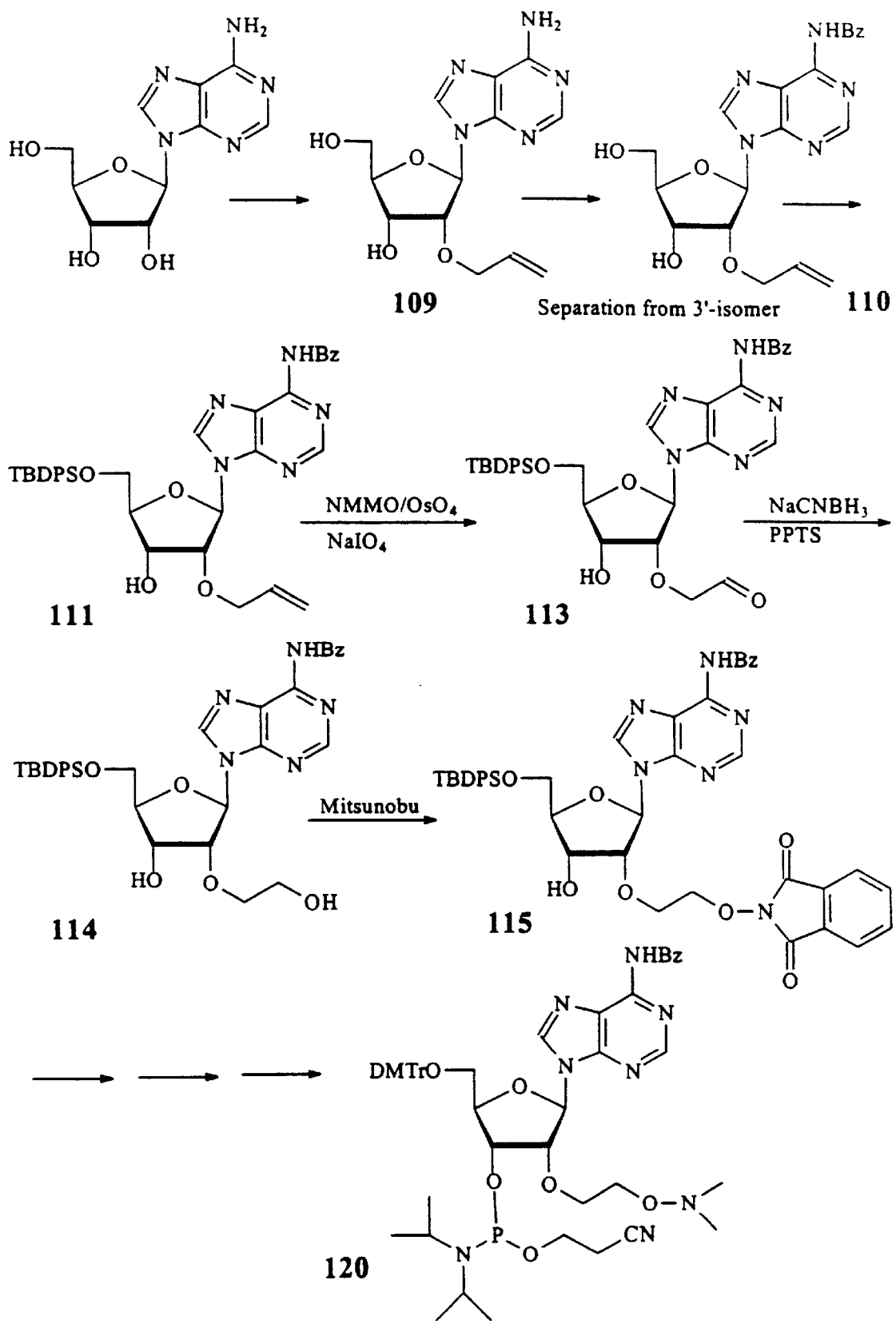
FIG. 18 shows a synthesis of intermediates and monomers of the invention.
Figure 19:
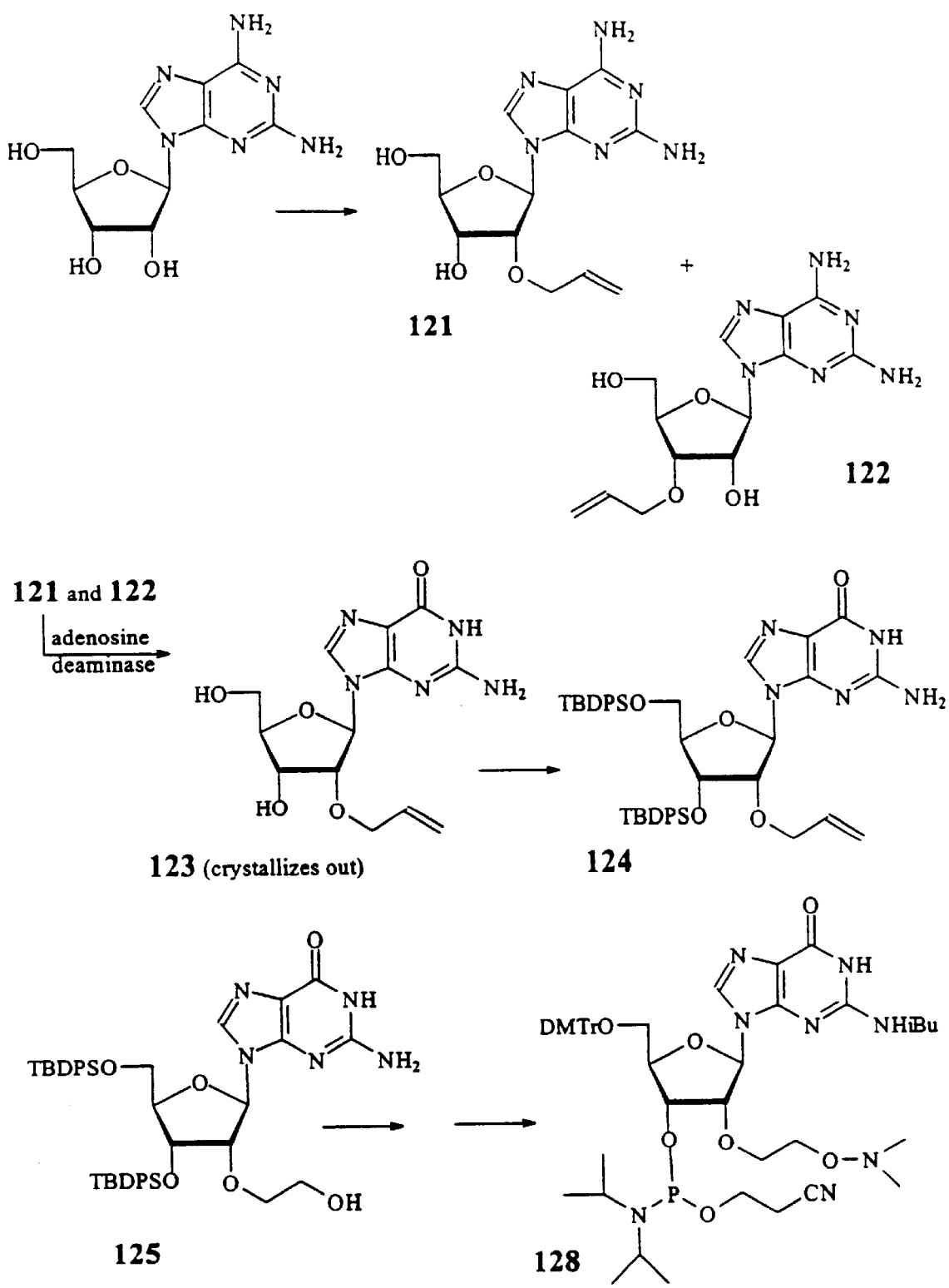
FIG. 19 shows a synthesis of intermediates and monomers of the invention.
Figure 20:
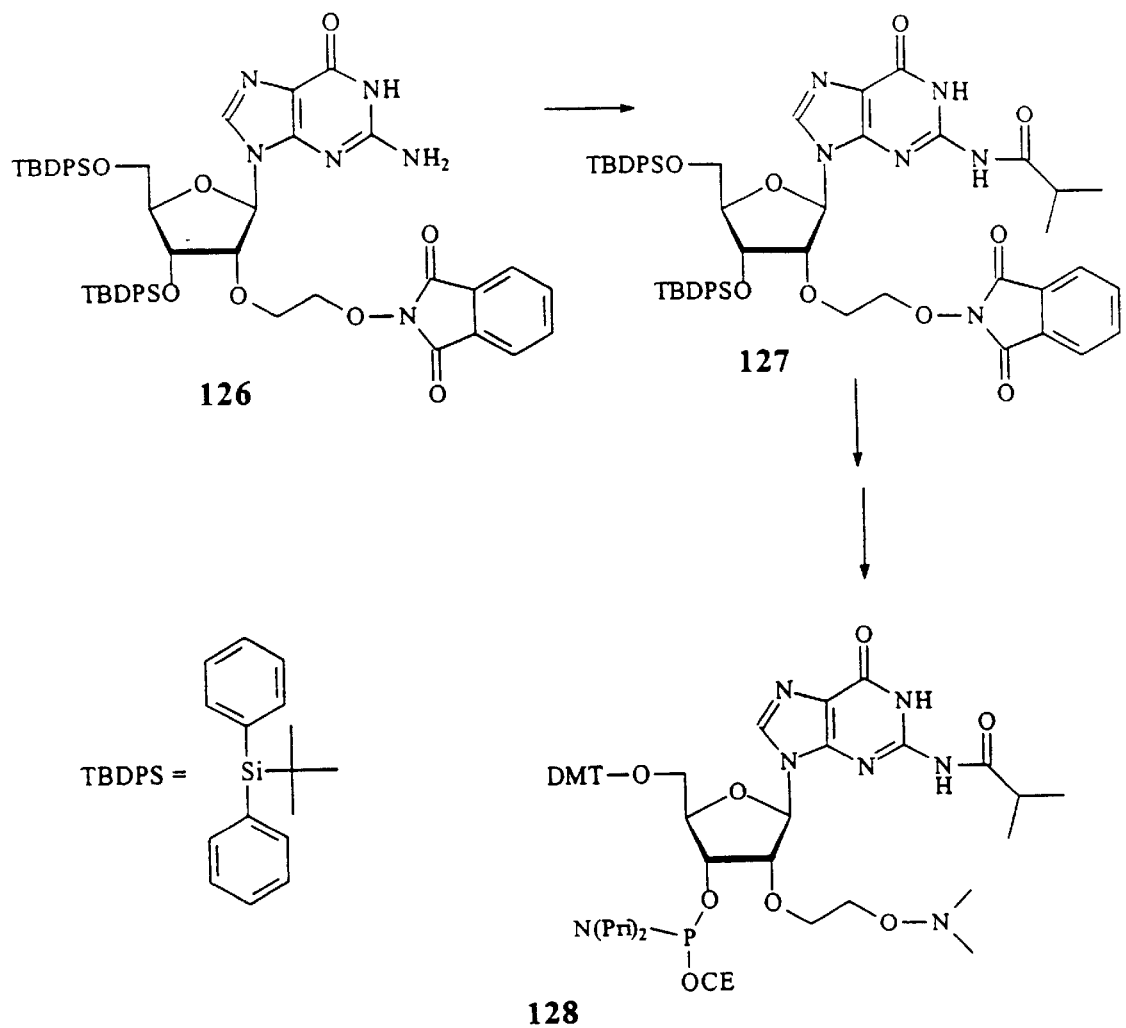
FIG. 20 shows a synthesis of intermediates and monomers of the invention.
Figure 21:
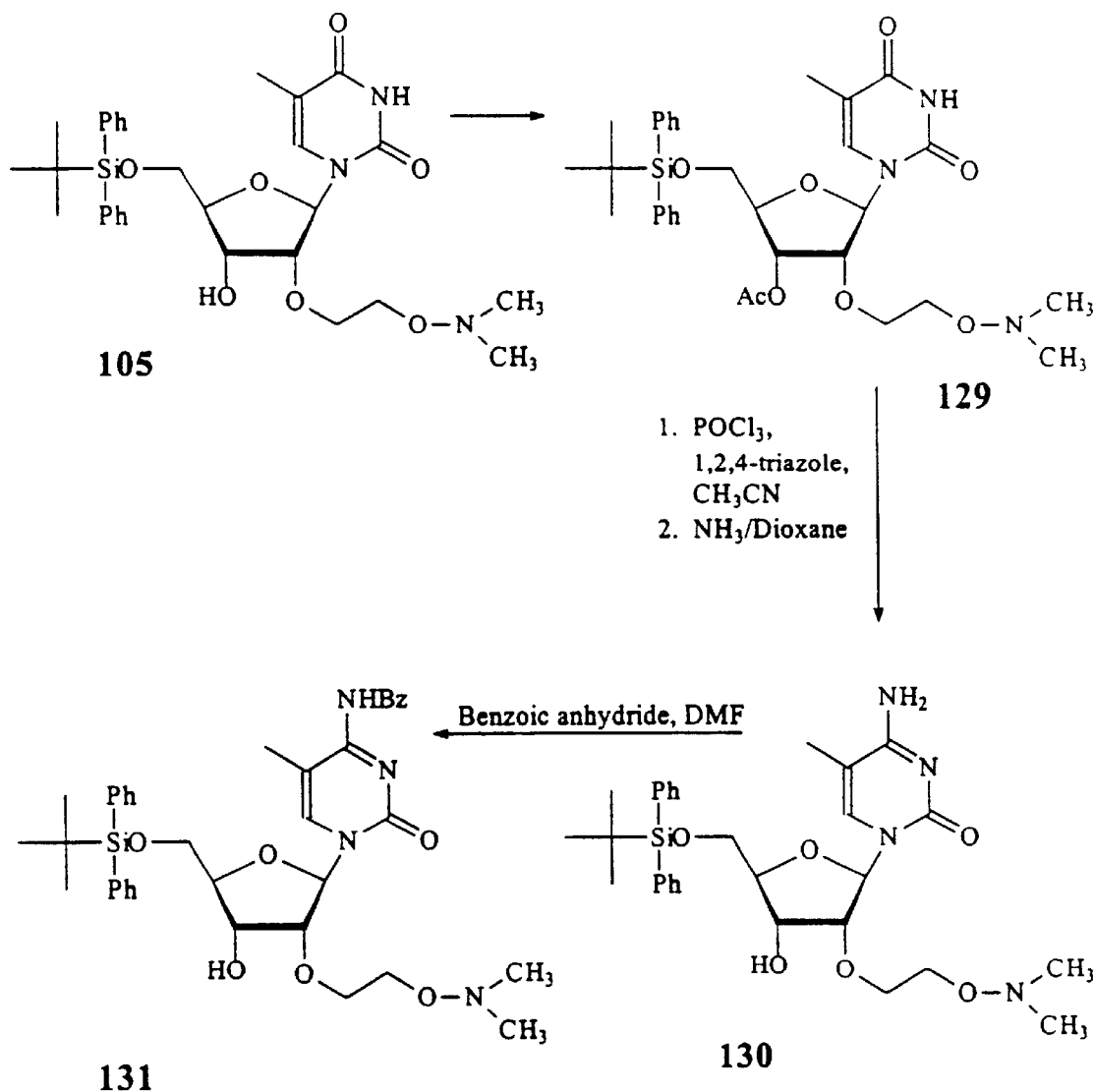
FIG. 21 shows a synthesis of intermediates and monomers of the invention.
Figure 22:
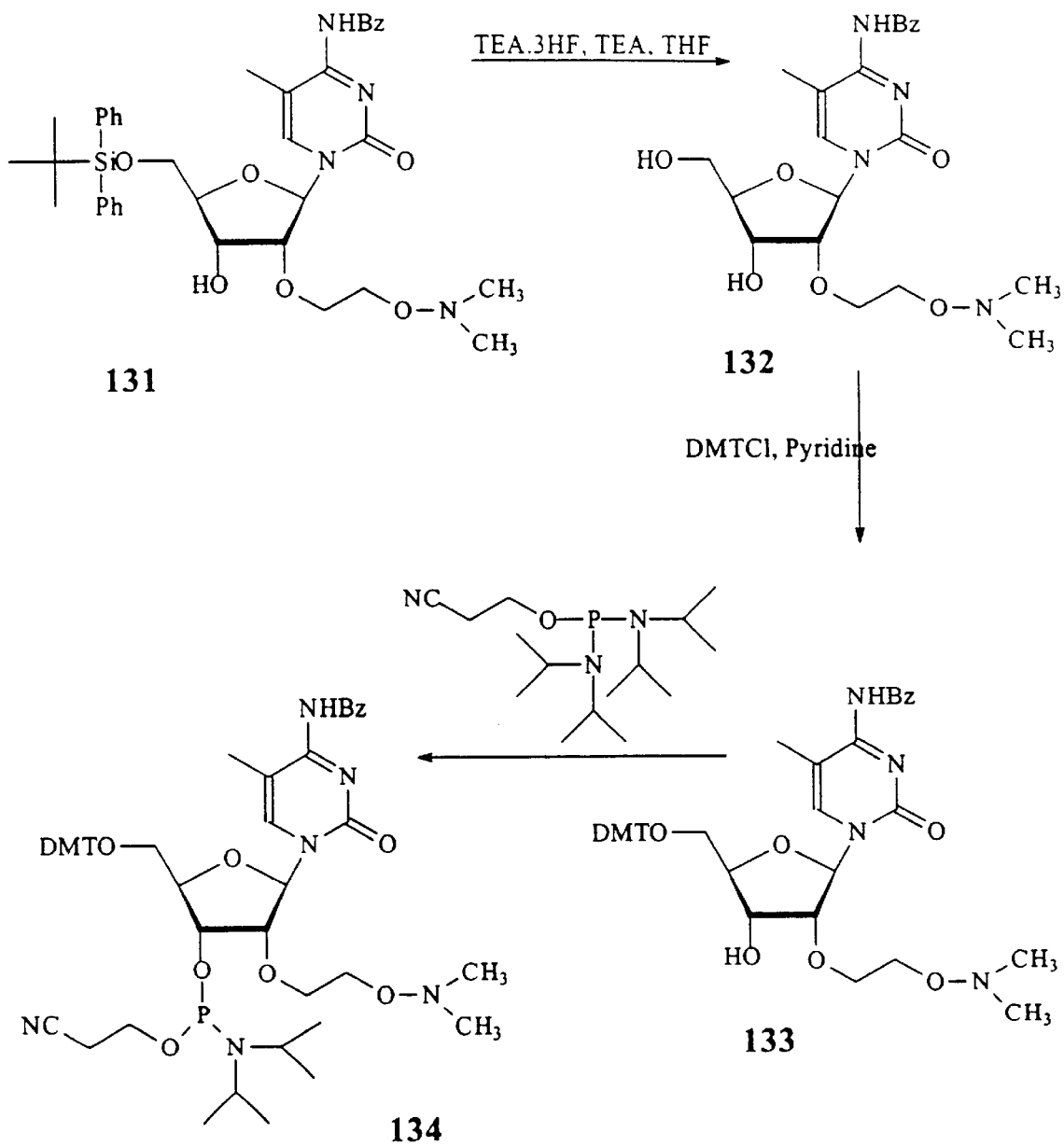
FIG. 22 shows a synthesis of intermediates and monomers of the invention.
Figure 23:
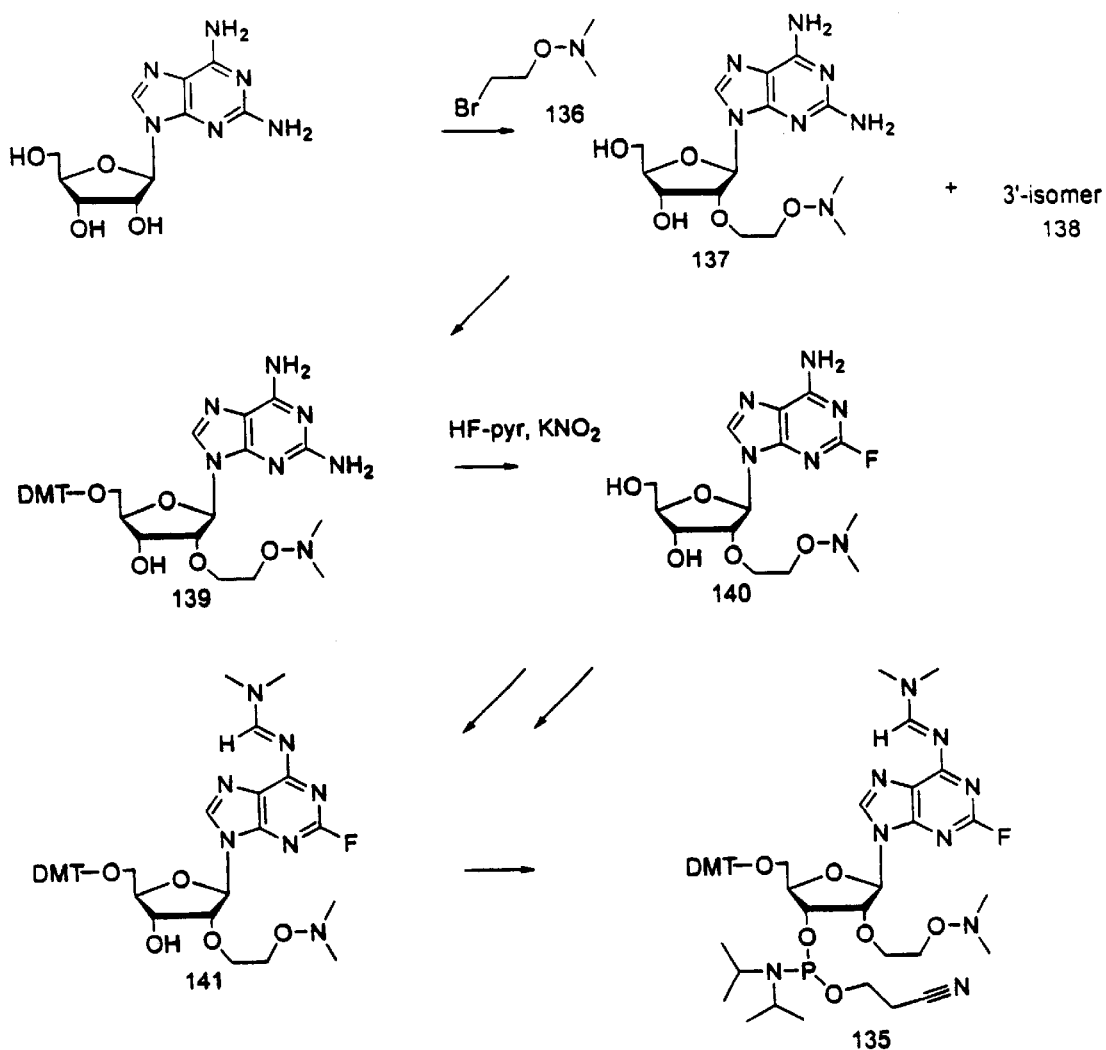
FIG. 23 shows a synthesis of intermediates and monomers of the invention.
Figure 24:
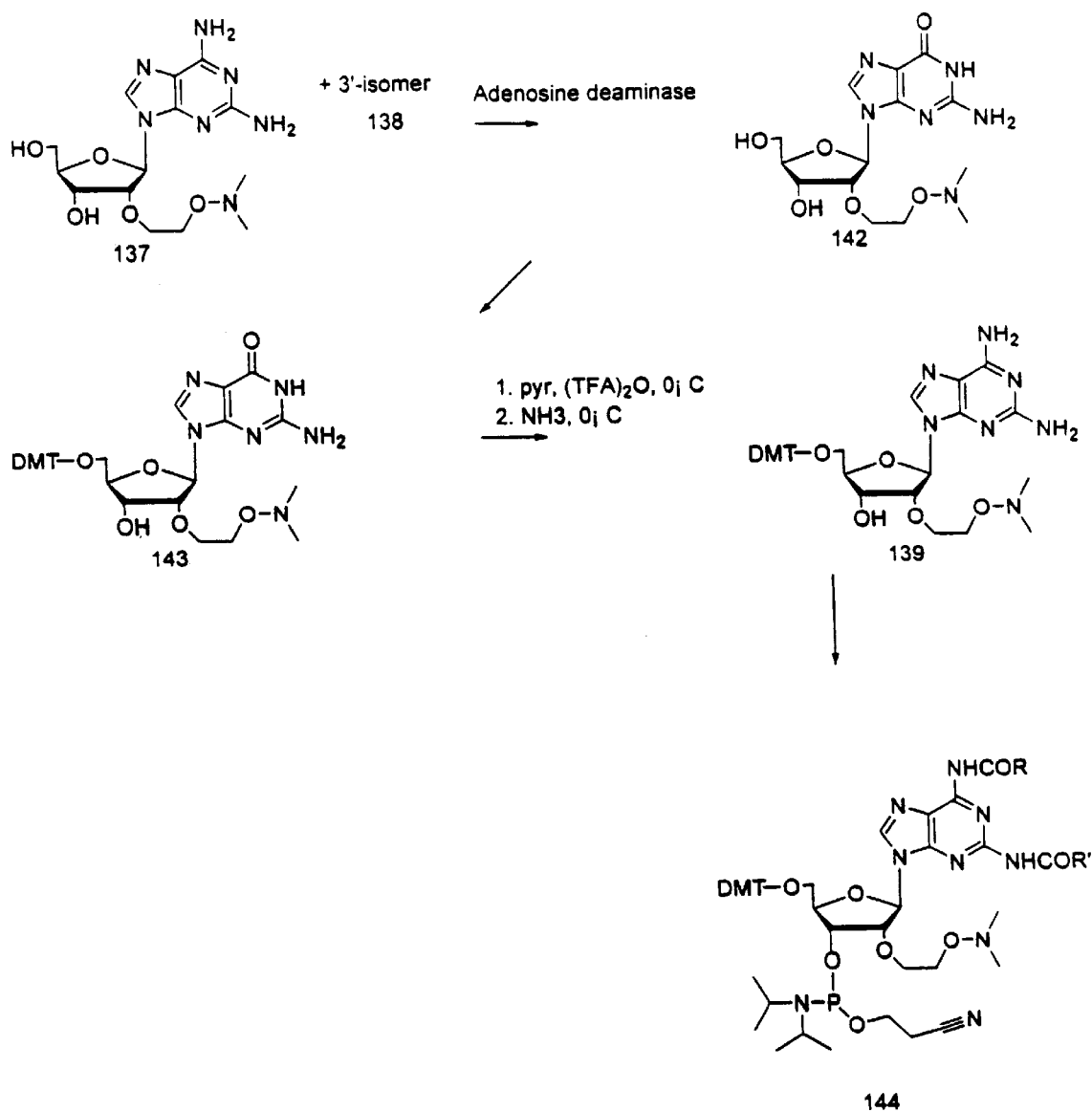
FIG. 24 shows a synthesis of intermediates and monomers of the invention.
Figure 25:
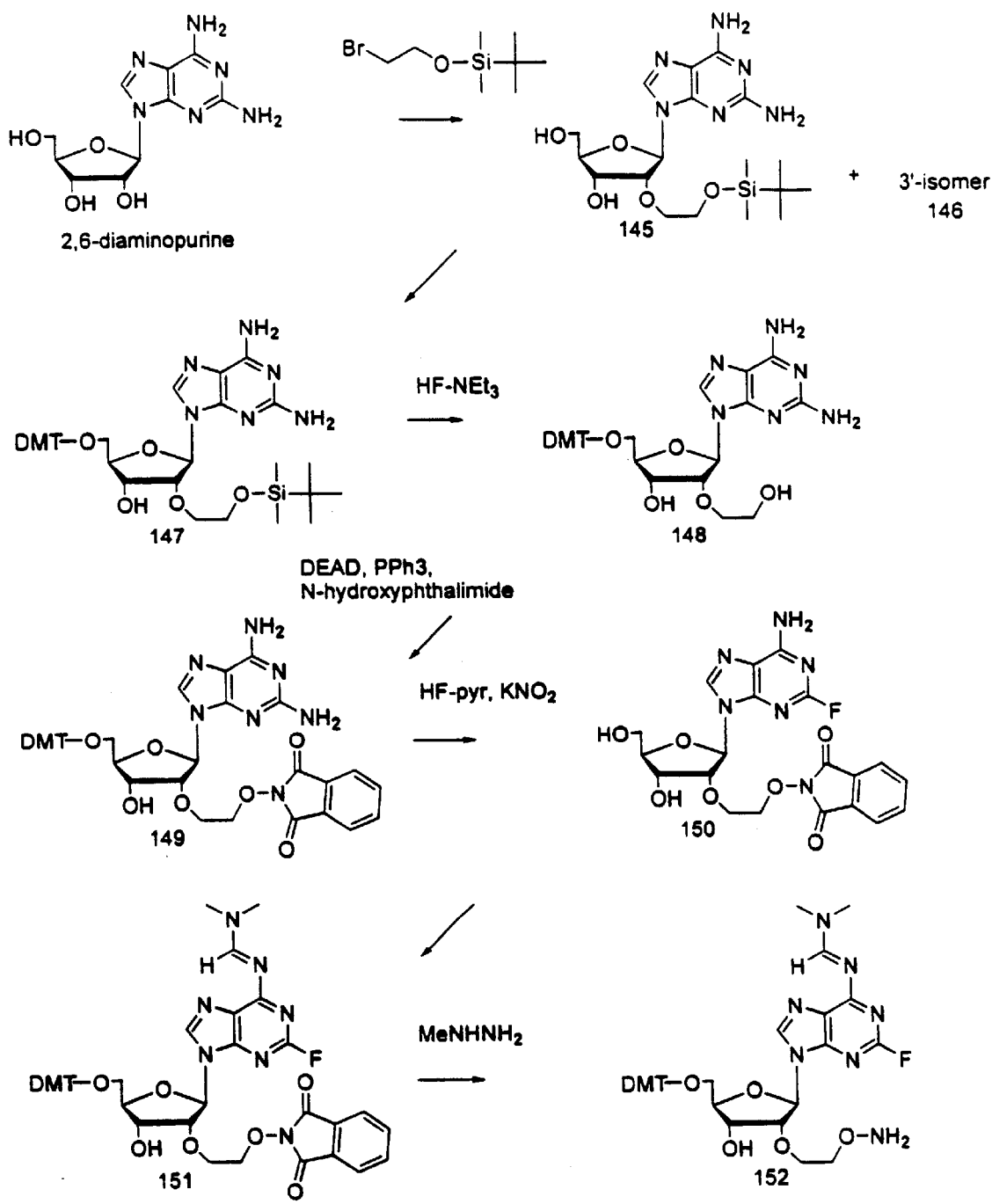
FIG. 25 shows a synthesis of intermediates and monomers of the invention.
Figure 26:
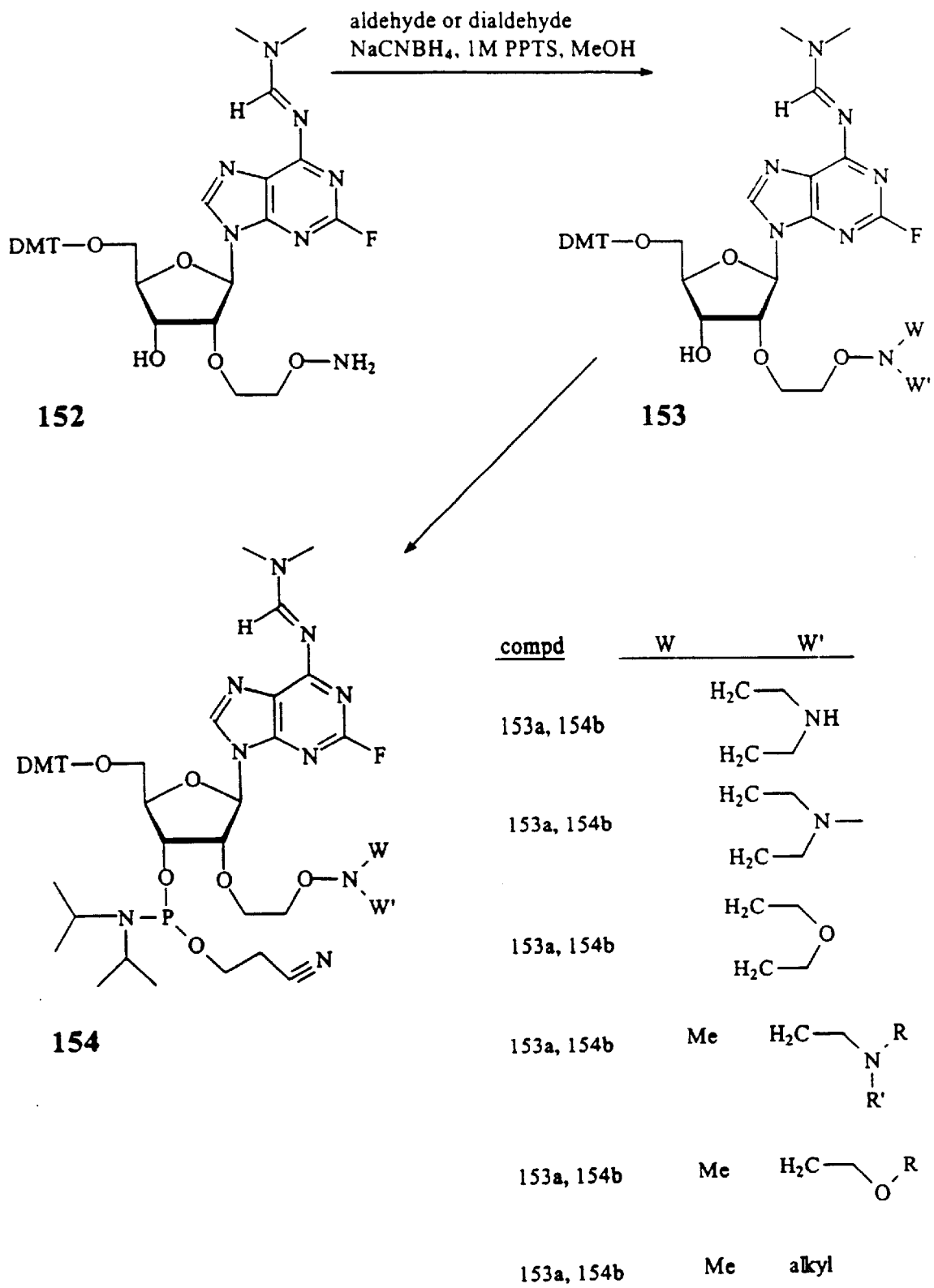
FIG. 26 shows a synthesis of intermediates and monomers of the invention.
Figure 27:
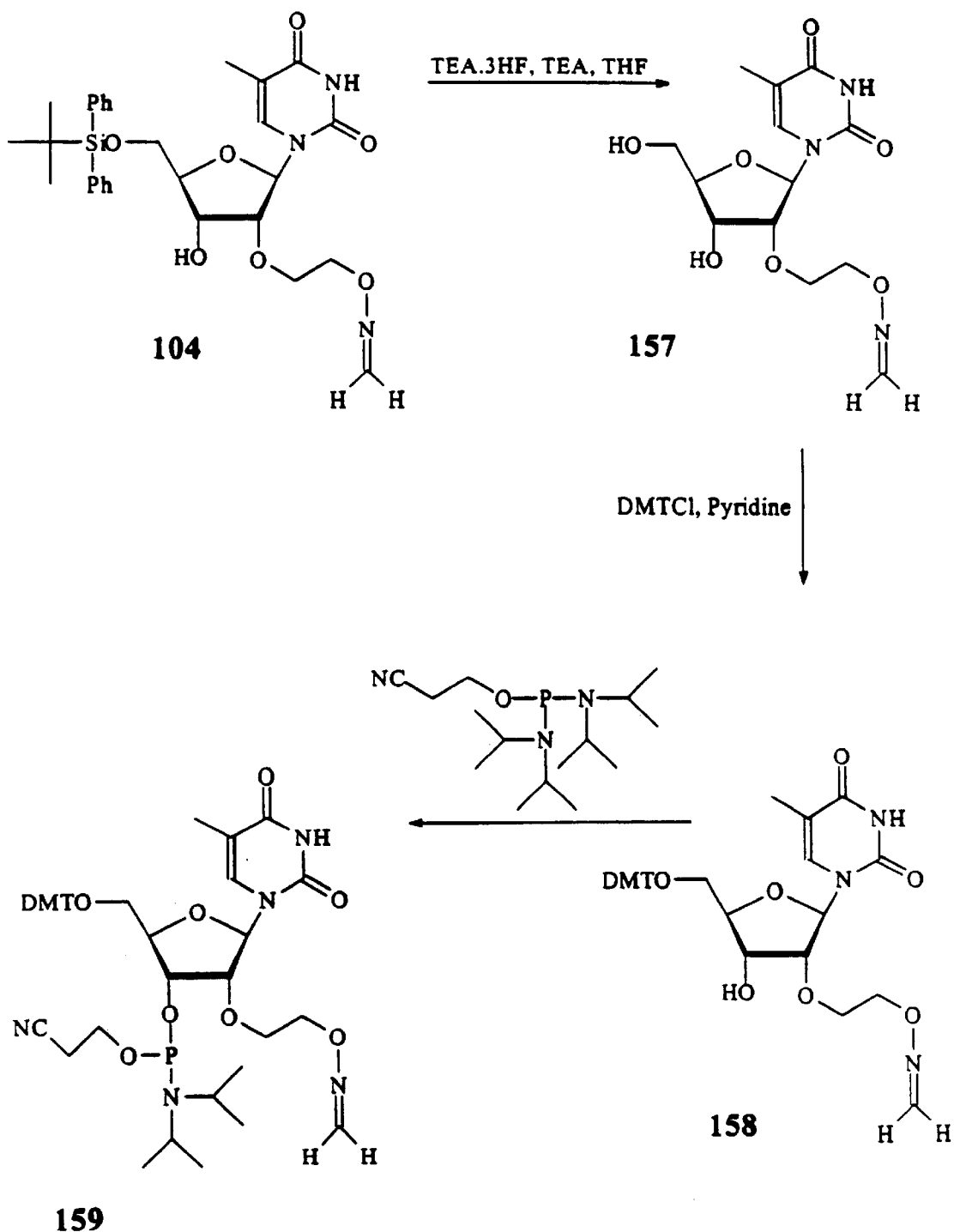
FIG. 27 shows a synthesis of intermediates and monomers of the invention.
Figure 28:
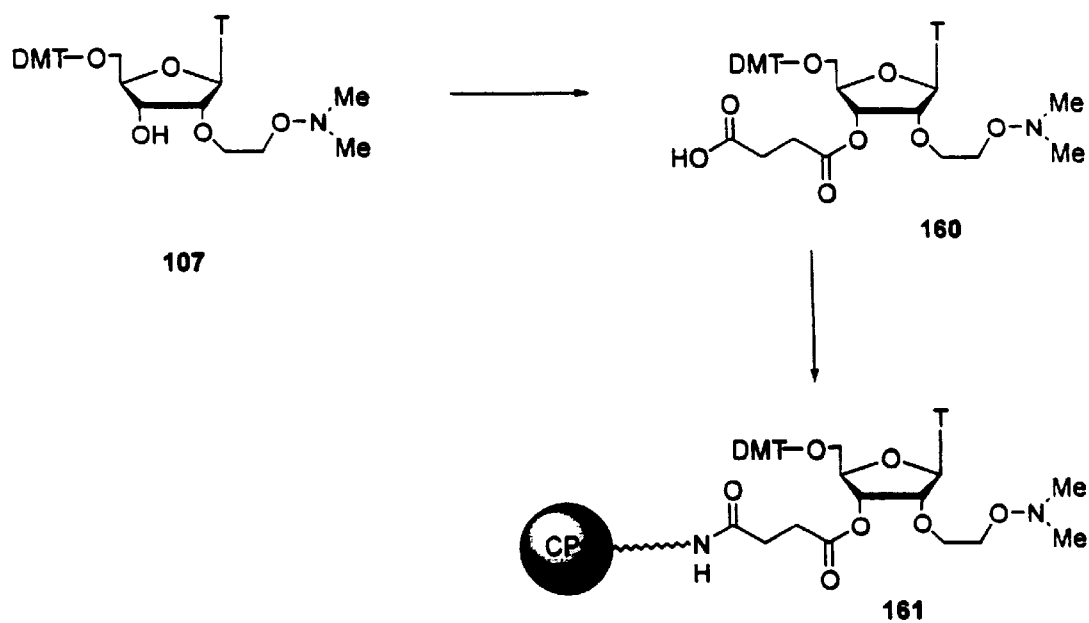
FIG. 28 shows a synthesis of intermediates and monomers of the invention.
Figure 29:
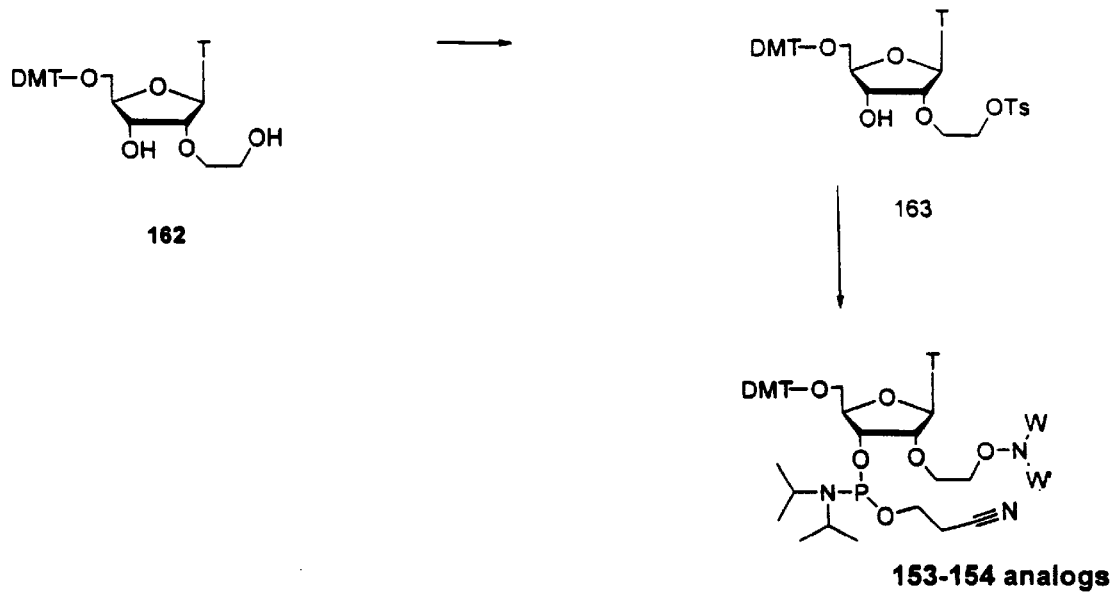
FIG. 29 shows a synthesis of intermediates and monomers of the invention.
Figure 29:
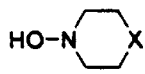
Figure 29:
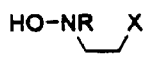
Figure 29:
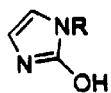
Figure 29:
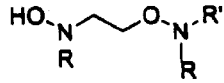
Figure 29:
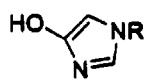
Figure 29:
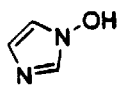
Figure 29:
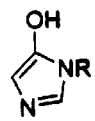
Figure 30:
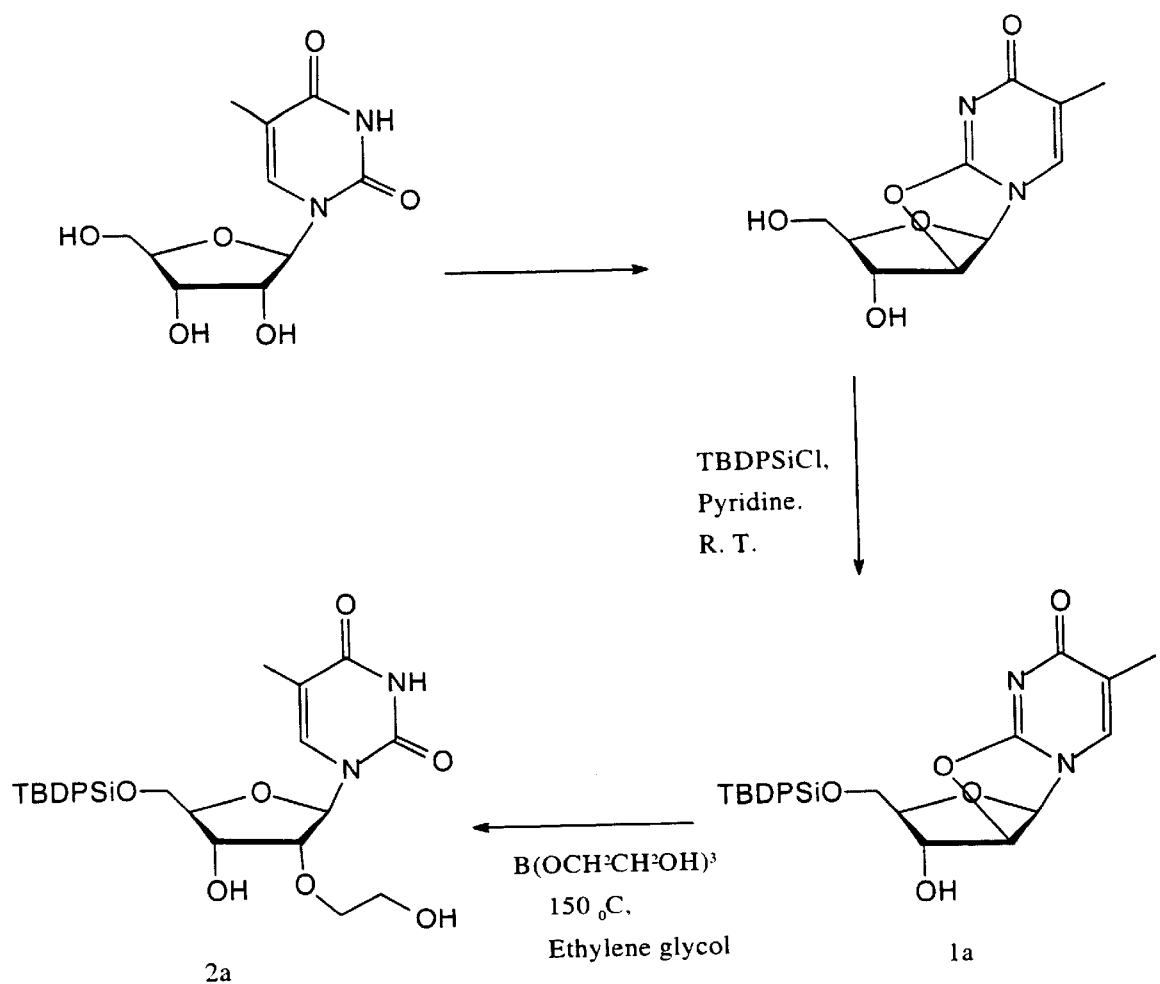
FIG. 30 shows a synthesis of intermediates and monomers of the invention.
Figure 31:
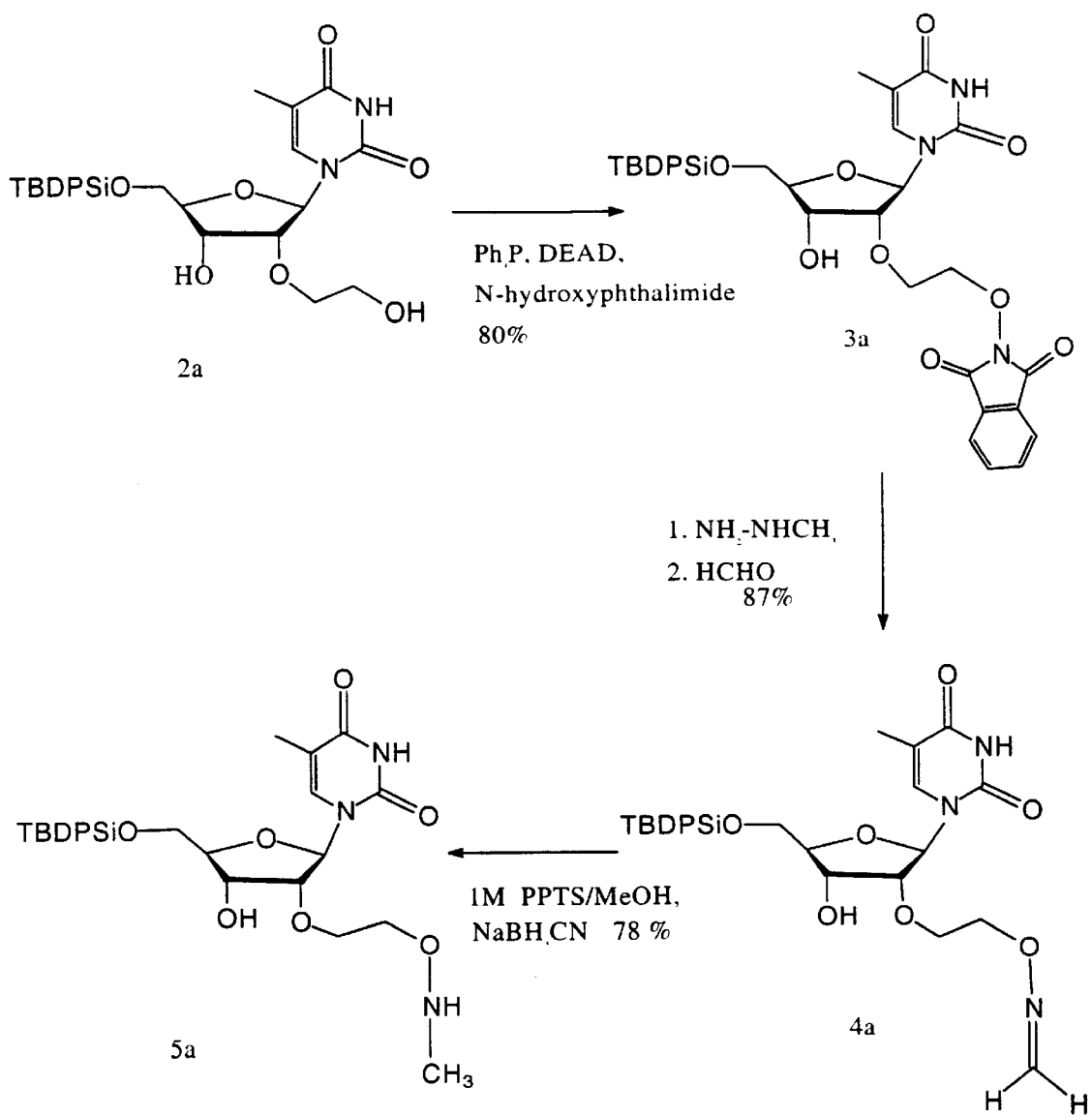
FIG. 31 shows a synthesis of intermediates and monomers of the invention.
Figure 32:
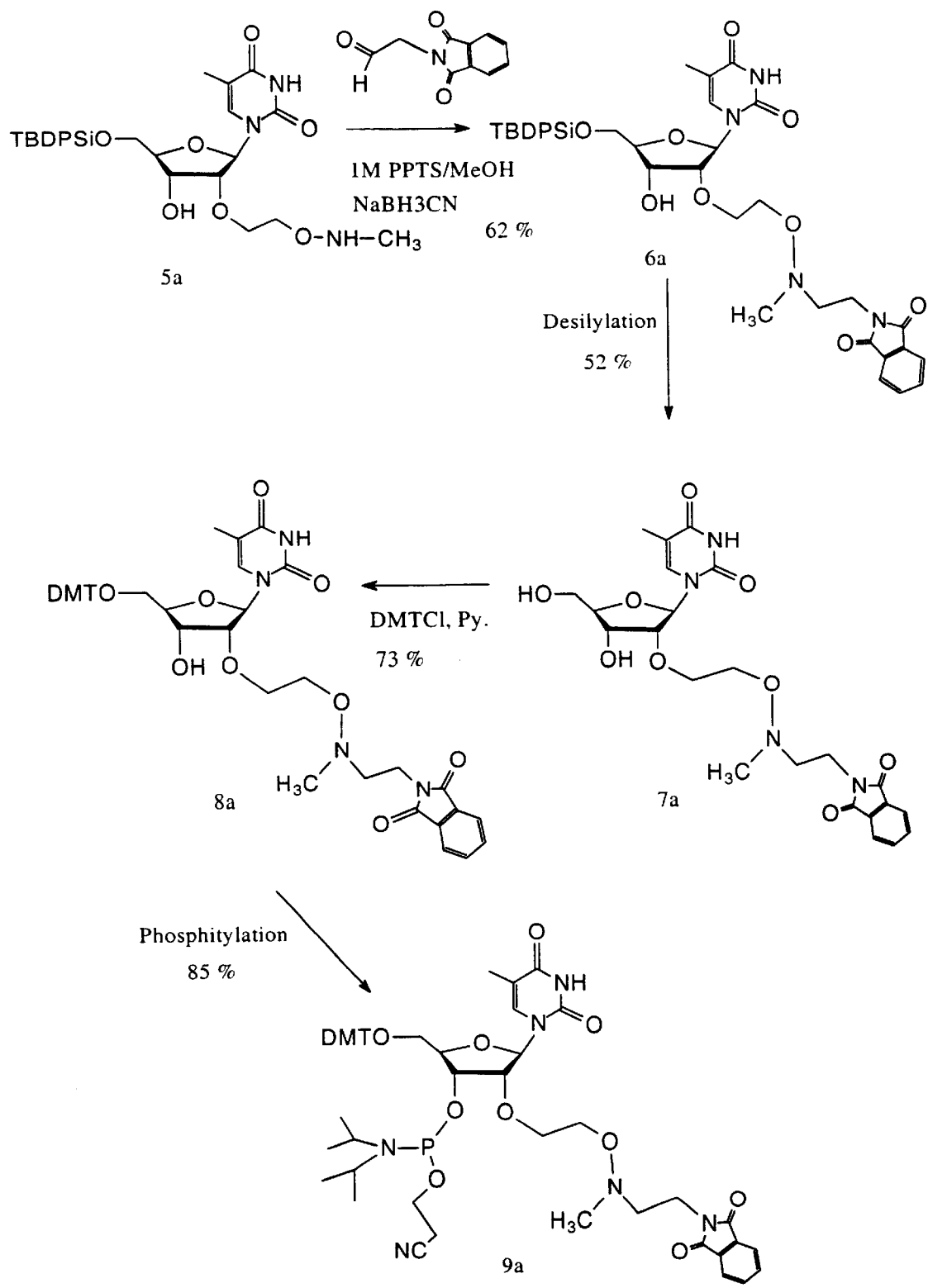
FIG. 32 shows a synthesis of intermediates and DMT phosphoramidite monomers of the invention.
Figure 33:
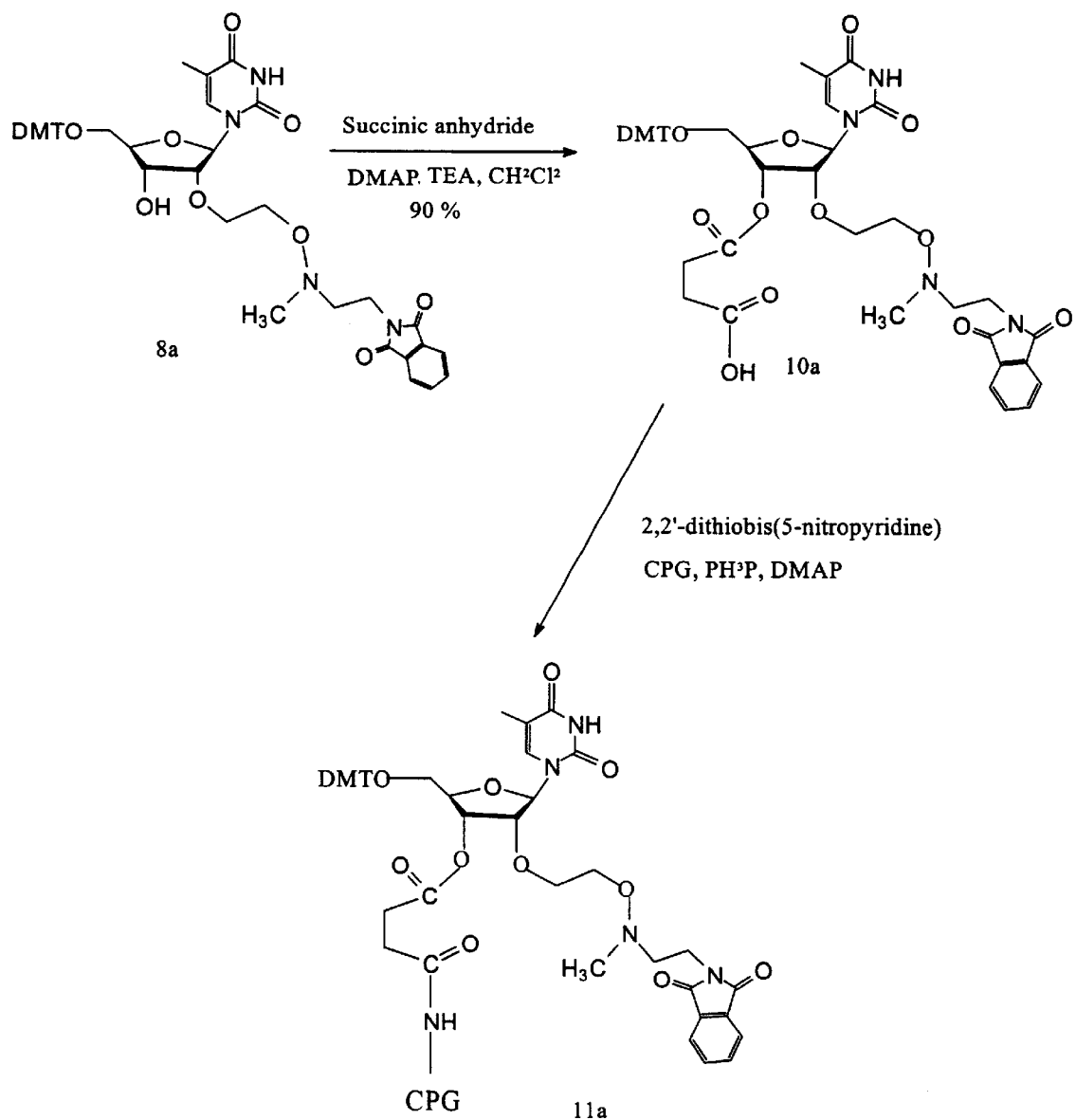
FIG. 33 shows a synthesis of intermediates and monomers of the invention attached to CPG.
Figure 34:
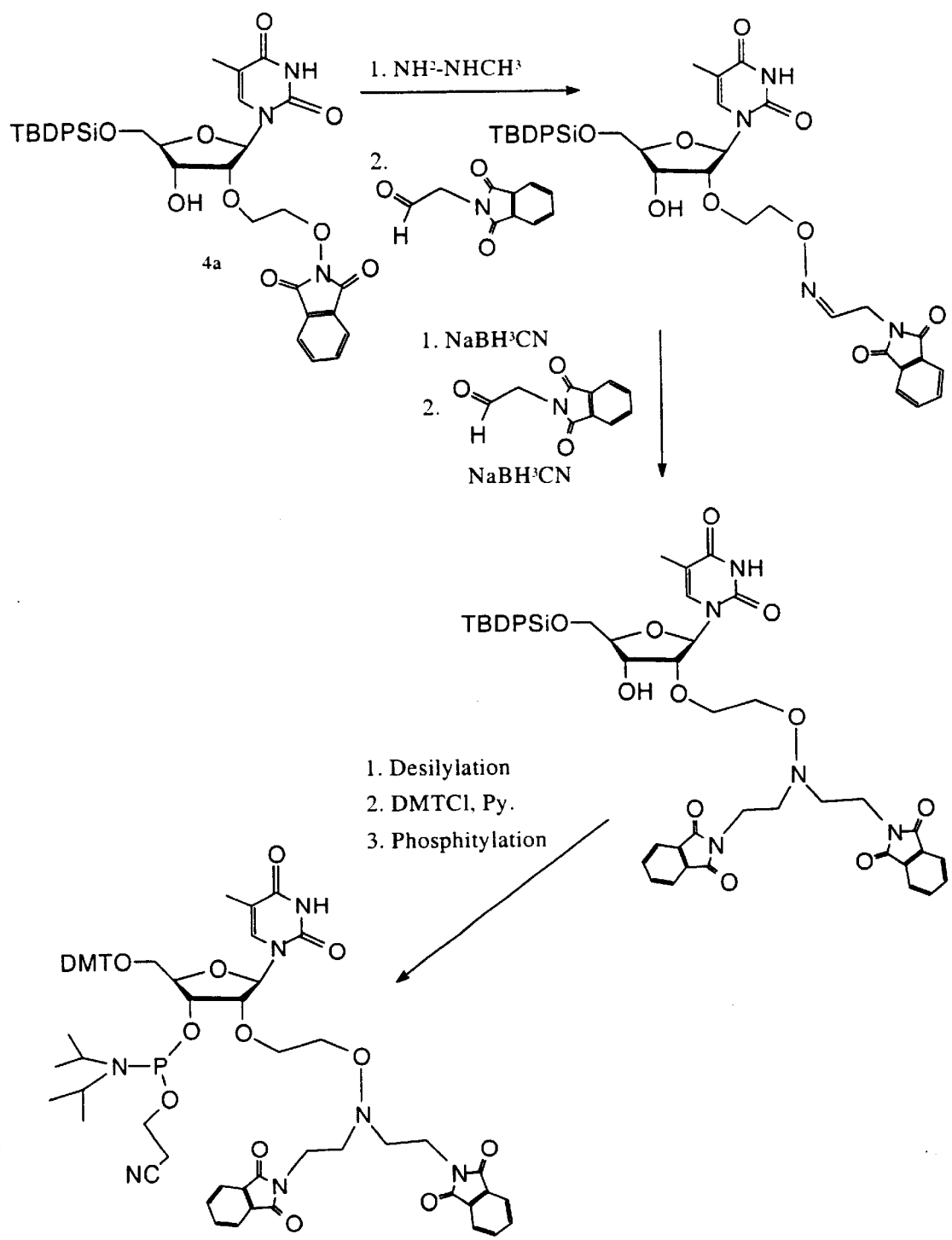
FIG. 34 shows a synthesis of intermediates and DMT phosphoramidite monomers of the invention.
Figure 35:
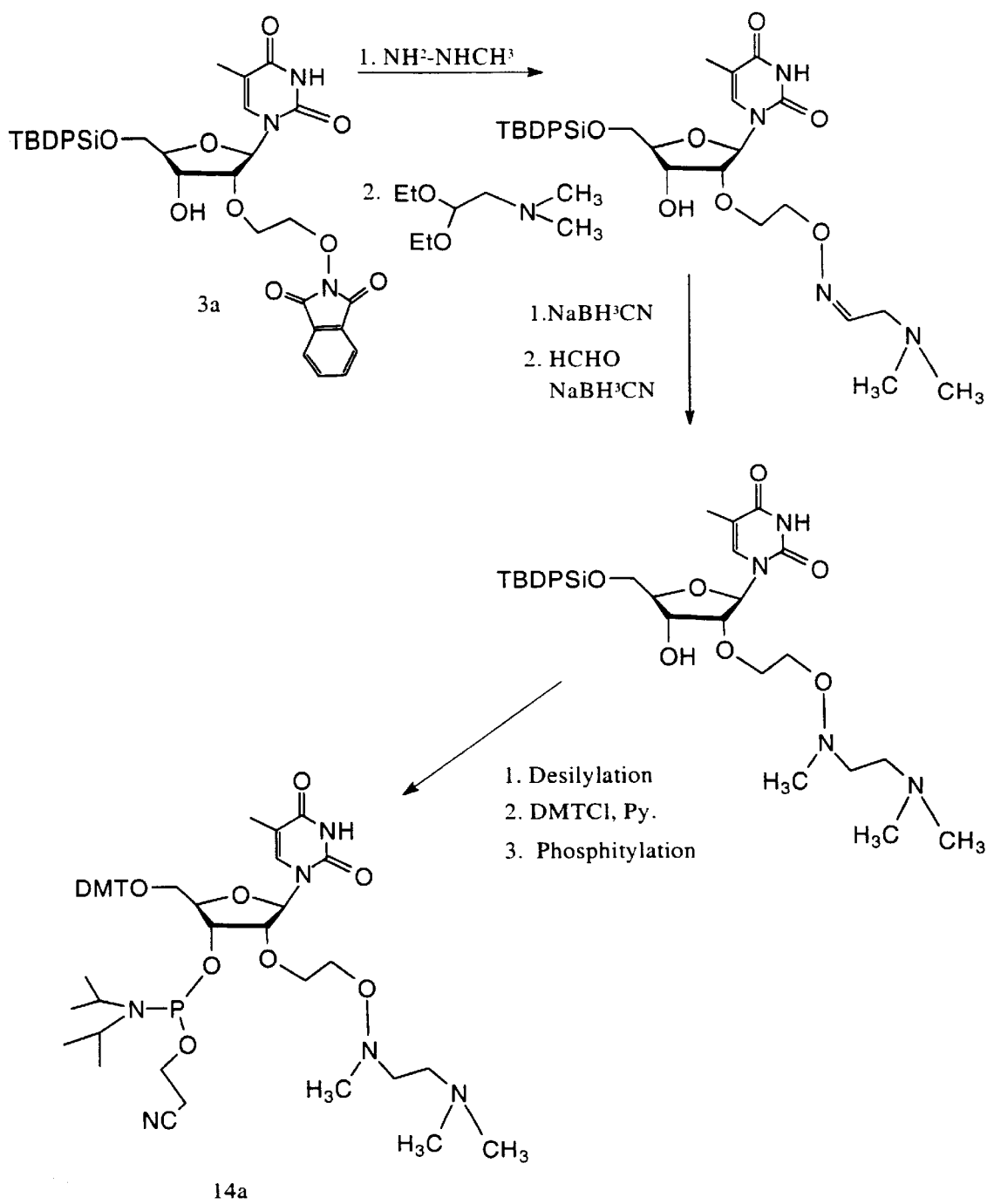
FIG. 35 shows a synthesis of intermediates and DMT phosphoramidite monomers of the invention.

Along with T19 diester and thioate controls, the gel purified oligos were 5' end labeled with $^{32}P$, and run through the standard nuclease assay protocol. PAGE/Phosphorimaging generated images that were quantified for % Intact and % (Intact+(N−1)). The percentages were plotted to generate half-lives, which are listed in a table below. Included is the half life of the 2'-O-methoxyethyl (MOE) analog in the table. This result showed that 2'-dimethylaminooxyethyl (DMAOE) is a highly nuclease resistant modification (FIGS. 14 and 15).

| | 2'-Modification | | |
|---|---|---|---|
| | AOE | DMAOE | MOE |
| T1/2 of N (min) | 18 | 60 | 100 |
| T1/2 of N + (N − 1) (min) | 200 | 85% remaining at 24 hr. | 300 |

Figure 13:
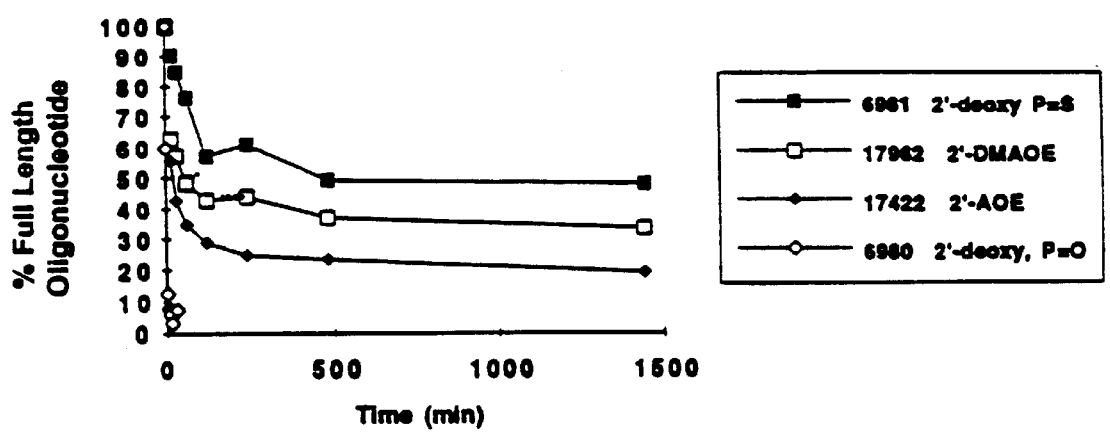
FIG. 13 shows a graph of % full length oligonucleotide versus time in minutes pertaining to effects of nuclease action on oligonucleotides.

Initial assays of the nuclease resistance of oligonucleotides capped with 2'-DMAOE modifications showed better resistance than modification 2'-O-methoxyethyl in an inter-assay comparison (FIG. 13). These studies are intra-assay comparisons among several modifications in two motifs. The first motif is a full phosphodiester backbone, with a cap of 4 modified nucleotides beginning at the 3'-most nucleotide. The second motif is similar, but contains a single phosphorothioate at the 3'-most inter nucleotide linkage.

| SEQ. ID NO: 14 Series II | |
|---|---|
| 5' TTT TTT TTT TTT TTT T*T*T* T* 3' | |
| SEQ ID NO 14 | where T* = 2'-O-dimethylaminooxyethyl |
| SEQ ID NO 14 | where T* = 2'-O-methoxyethyl |
| SEQ ID NO 14 | where T* = 2'-O-propyl |

| SEQ. ID NO: 14 Series III | |
|---|---|
| 5' TTT TTT TTT TTT TTT TTT*T 3' | |
| SEQ ID NO 14 | where T* = 5 methyl, 2'-dimethylaminooxyethyl |
| SEQ ID NO 14 | where T* = 5 methyl, 2'-O-methoxyethyl |

Along with a T19 phosphorothioate control, the oligos were gel purified and run through the standard nuclease protocol. From these assays SEQ ID NO: 14 where T*=2'-O-dimethylaminooxyethyl proved to be the next most resistant oligonucleotide. SEQ ID NO: 14 where T*=2'-O-methoxyethyl was degraded more readily and SEQ ID NO: 14 where T*=2'-O-propyl is degraded rather quickly. The gel shows some reaction products at the bottom of the gel, but little n-2 and n-3 of the resistant oligonucleotides. These products appear to be the result of endonucleolytic cleavage by SVPD. This type of activity is always present at a basal rate, but is not usually seen due to the overwhelming predominance of 3' exonuclease activity on most oligonucleotides. However, these oligonucleotides are so extraordinarily resistant to 3' exonucleases that the endonuclease activity is responsible for a majority of the cleavage events on the full-length oligo. 2'-deoxy phosphodiester products of the endonuclease reactions are then rapidly cleaved to monomers. Two sets of quantitation are done for these reactions. One counts only 3'-exonuclease products, and the other counts products for all reactions. In either case, the half-life of SEQ ID NO: 14 where T*=2'-O-dimethylaminooxyethyl was longer than 24 hours. For SEQ ID NO: 14 where T*=2'-O-methoxyethyl the half life upon treatment with exonuclease is over 24 hours while the other type of quantitation gives a half-life of about 100 min. The oligonucleotides of the motif containing a single phosphorothioate linkage are substrates for the endonuclease activity described above, but no products of 3' exonuclease activity are detected in the time course of this assay.

TABLE 2

Oligonucleotides synthesized with 2'-dimethylaminooxyethyl thymidine (T-2'-DMAOE)

| SEQ ID NO: | Sequence | Mass Exp. | Mass Obs. |
|---|---|---|---|
| 5 | 5'- CTCGTACCT*TTCCGGTCC-3' | 5784.20 | 5784.09 |
| 15 | 5'-T*CCAGGT*GT*CCGCAT*C-3' | 5548.74 | 5549.05 |
| 3 | 5'-GCGT*T*T*T*T*T*T*T*T*GCG-3' | 6208.74 | 6210.52 |
| 14 | 5'-TTTTTTTTTTTTTTT*T*T*T*T-3' | 6433.45 | 6433.79 |
| N/A | 5'-T*T*T*T*-3' | 1869.96 | 1869.5 |
| 14 | 5'-TTTTTTTTTTTTTTT*T*T*<sub>s</sub>T*-3' | 6449.45 | 6449.15 |
| 14 | TTTTTTTTTTTTTTT*T*T*-3' | 6433.51 | 6433.19 |
| N/A | 5'-T*T*-3' | 648.49 | 648.4 |

TABLE 3

Oligonucleotides synthesized with 2'-dimethylaminooxyethyl adenosine (A-2'-DMAOE)

| | SEQ ID NO: | Sequence | Mass Exp. | Mass Obs. |
|---|---|---|---|---|
| 1 | 7 | 5'- CTCGTACCA*TTCCGGTCC-3' | 5490.21 | 5490.86 |
| 2 | 8 | 5'-GGA*CCGGA*A*GGTA*CGA*G-3' | 5824.96 | 5826.61 |
| 3 | 16 | 5'-A*CCGA*GGA*GGA*TCA*TGTCGTA*CGC-3' | 6947.9 | 6947.28 |

TABLE 4

Oligonucleotides synthesized with 2'-O-methyleneiminooxyethyl adenosine

| SEQ ID NO: | Sequence | Mass Exp. | Mass Obs. |
|---|---|---|---|
| 7 | 5'-CTCGTACCA*TTCCGGTCC-3' | 5470.20 | 5472.50 |
| 17 | 5'-A*CCGA*GGA*TCA*TGTCGTA*CGC-3' | 6866.42 | 6865.88 |
| 8 | 5'-GGA*CCGGA*A*GGTA*CGA*G-3' | 5743.12 | 5743.82 |

TABLE 5

Oligonucleotides synthesized with 2'-O-methyleneiminooxyethyl thymidine

| | SEQ ID NO: | Sequence | Mass Exp. | Mass Obs. |
|---|---|---|---|---|
| 1 | 5 | 5'-CTCGTACCT*TTCCGGTCC-3' | 5466.21 | 5462.25 |
| 2 | 15 | 5'-T*CCAGGT*GT*CCGCAT*C-3' | 5179.44 | 5178.96 |
| 3 | 14 | 5'-TTTTTTTTTTTTTTT*T*T*T*T-3' | 6369.45 | 6367.79 |

TABLE 6

Tm advantage of 2'-DMAOE modification over 2'-deoxy phosphodiesters and phosphorothioates

| SEQ. ID NO: | SEQUENCE | Tm | ΔTm/mod against RNA compared to unmodified DNA | ΔTm/mod against RNA compared to unmodified deoxy-phosphorothioate |
|---|---|---|---|---|
| 5 | 5'-CTCGTAC-CT*T-TCCGGTCC-3' | 65.44 | 0.24 | 1.04 |
| 15 | 5'-T*CCAGGT*GT*C-CGCAT*C-3' | 67.90 | 1.12 | 2.20 |
| 3 | 5'-GCGT*T*T*T*T*T*T*T*T*GCG-3' | 62.90 | 1.46 | 2.36 |

ΔTm is based on reported literature values for DNA and phosphorothioate oligonucleotides.

Procedure 2
Ras-Luciferase Reporter Gene Assembly

The ras-luciferase reporter genes described in this study are assembled using PCR technology. Oligonucleotide primers are synthesized for use as primers for PCR cloning of the 5'-regions of exon 1 of both the mutant (codon 12) and non-mutant (wild-type) human H-ras genes. H-ras gene templates are purchased from the American Type Culture Collection (ATCC numbers 41000 and 41001) in Bethesda, Md. The oligonucleotide PCR primers 5'-ACA-TTA-TGC-TAG-CTT-TTT-GAG-TAA-ACT-TGT-GGG-GCA-GGA-GAC-CCT-GT-3' (sense) (SEQ ID NO:10), and 5'-GAG-ATC-TGA-AGC-TTC-TGG-ATG-GTC-AGC-GC-3' (antisense) (SEQ ID NO:11), are used in standard PCR reactions using mutant and non-mutant H-ras genes as templates. These primers are expected to produce a DNA product of 145 base pairs corresponding to sequences −53 to +65 (relative to the translational initiation site) of normal and mutant H-ras, flanked by NheI and HindIII restriction endonuclease sites. The PCR product is gel purified, precipitated, washed and resuspended in water using standard procedures.

PCR primers for the cloning of the *P. pyralis* (firefly) luciferase gene were designed such that the PCR product would code for the full-length luciferase protein with the exception of the amino-terminal methionine residue, which would be replaced with two amino acids, an amino-terminal lysine residue followed by a leucine residue. The oligonucleotide PCR primers used for the cloning of the luciferase gene are 5'-GAG-ATC-TGA-AGC-TTG-AAG-ACG-CCA-AAA-ACA-TAA-AG-3' (sense) (SEQ ID NO:12), and 5'-ACG-CAT-CTG-GCG-CGC-CGA-TAC-CGT-CGA-CCT-CGA-3' (antisense) (SEQ ID NO:13), are used in standard PCR reactions using a commercially available plasmid (pT3/T7-Luc) (Clontech), containing the luciferase reporter gene, as a template. These primers are expected to yield a product of approximately 1.9 kb corresponding to the luciferase gene, flanked by HindIII and BssHII restriction endonuclease sites. This fragment is gel purified, precipitated, washed and resuspended in water using standard procedures.

To complete the assembly of the ras-luciferase fusion reporter gene, the ras and luciferase PCR products are digested with the appropriate restriction endonucleases and cloned by three-part ligation into an expression vector containing the steroid-inducible mouse mammary tumor virus promotor MMTV using the restriction endonucleases NheI, HindIII and BssHII. The resulting clone results in the insertion of H-ras 5' sequences (−53 to +65) fused in frame with the firefly luciferase gene. The resulting expression vector encodes a ras-luciferase fusion product which is expressed under control of the steroid-inducible MMTV promoter.

Procedure 3
Transfection of Cells with Plasmid DNA

Transfections are performed as described by Greenberg in *Current Protocols in Molecular Biology,* Ausubel et al., Eds., John Wiley and Sons, New York, with the following modifications: HeLa cells are plated on 60 mm dishes at $5\times10^5$ cells/dish. A total of 10 μg of DNA is added to each dish, of which 9 μg is ras-luciferase reporter plasmid and 1 μg is a vector expressing the rat glucocorticoid receptor under control of the constitutive Rous sarcoma virus (RSV) promoter. Calcium phosphate-DNA coprecipitates are removed after 16–20 hours by washing with Tris-buffered saline (50 Mm Tris-Cl (pH 7.5), 150 mM NaCl) containing 3 mM EGTA. Fresh medium supplemented with 10% fetal bovine serum is then added to the cells. At this time, cells are pre-treated with antisense oligonucleotides prior to activation of reporter gene expression by dexamethasone.

Procedure 4
Oligonucleotide Treatment of Cells

Immediately following plasmid transfection, cells are thrice washed with OptiMEM (GIBCO), and prewarmed to 37° C. 2 ML of OptiMEM containing 10 μg/ML N-[1-(2,3-diolethyloxy)propyl]-N,N,N,-trimethylammonium chloride (DOTMA) (Bethesda Research Labs, Gaithersburg, Md.) is added to each dish and oligonucleotides are added directly and incubated for 4 hours at 37° C. OptiMEM is then removed and replaced with the appropriate cell growth medium containing oligonucleotide. At this time, reporter gene expression is activated by treatment of cells with dexamethasone to a final concentration of 0.2 μM. Cells are harvested 12–16 hours following steroid treatment.

Procedure 5
Luciferase Assays

Luciferase is extracted from cells by lysis with the detergent Triton X-100, as described by Greenberg in *Current Protocols in Molecular Biology,* Ausubel et al., Eds., John Wiley and Sons, New York. A Dynatech ML1000 luminometer is used to measure peak luminescence upon addition of luciferin (Sigma) to 625 μM. For each extract, luciferase assays are performed multiple times, using differing amounts of extract to ensure that the data are gathered in the linear range of the assay.

Procedure 6
Antisense Oligonucleotide Inhibition of ras-Luciferase Gene Expression A series of antisense phosphorothioate oligonucleotide analogs targeted to the codon-12 point mutation of activated H-ras are tested using the ras-luciferase reporter gene system described in the foregoing examples. This series comprised a basic sequence and analogs of that basic sequence. The basic sequence is of known activity as reported in International Publication Number WO 92/22651 identified above. In both the basic sequence and its analogs, each of the nucleotide subunits incorporated phosphorothioate linkages to provide nuclease resistance. Each of the analogs incorporated nucleotide subunits that contained 2'-O-substitutions and 2'-deoxy-erythro-pentofuranosyl sugars. In the analogs, a subsequence of the 2'-deoxy-erythro-pentofuranosyl sugar-containing subunits is flanked on both ends by subsequences of 2'-O-substituted subunits. The analogs differed from one another with respect to the length of the subsequence of the 2'-deoxy-erythro-pentofuranosyl sugar containing nucleotides. The length of these subsequences are varied by 2 nucleotides between 1 and 9 total nucleotides. The 2'-deoxy-erythro-pentofuranosyl nucleotide sub-sequences are centered at the point mutation of the codon-12 point mutation of the activated ras.

Procedure 7
Diagnostic Assay for the Detection of mRNA Overexpression

Oligonucleotides are radiolabeled after synthesis by $^{32}$P labeling at the 5' end with polynucleotide kinase. Sambrook et al. (*"Molecular Cloning. A Laboratory Manual,"* Cold Spring Harbor Laboratory Press, 1989, Volume 2, pg. 11.31–11.32). Radiolabeled oligonucleotide is contacted with tissue or cell samples suspected of mRNA overexpression, such as a sample from a patient, under conditions in which specific hybridization can occur, and the sample is washed to remove unbound oligonucleotide. A similar control is maintained wherein the radiolabeled oligonucleotide is contacted with normal cell or tissue sample under conditions that allow specific hybridization, and the sample is washed to remove unbound oligonucleotide. Radioactivity remaining in the sample indicates bound oligonucleotide and is quantitated using a scintillation counter or other routine means. Comparison of the radioactivity remaining in the samples from normal and diseased cells indicates overexpression of the mRNA of interest.

Radiolabeled oligonucleotides of the invention are also useful in autoradiography. Tissue sections are treated with radiolabeled oligonucleotide and washed as described above, then exposed to photographic emulsion according to standard autoradiography procedures. A control with normal cell or tissue sample is also maintained. The emulsion, when developed, yields an image of silver grains over the regions overexpressing the mRNA, which is quantitated. The extent of mRNA overexpression is determined by comparison of the silver grains observed with normal and diseased cells.

Analogous assays for fluorescent detection of mRNA expression use oligonucleotides of the invention which are labeled with fluorescein or other fluorescent tags. Labeled DNA oligonucleotides are synthesized on an automated DNA synthesizer (Applied Biosystems model 380B) using standard phosphoramidite chemistry with oxidation by iodine. β-cyanoethyldiisopropyl phosphoramidites are purchased from Applied Biosystems (Foster City, Calif.). Fluorescein-labeled amidites are purchased from Glen Research (Sterling, Va.). Incubation of oligonucleotide and biological sample is carried out as described for radiolabeled oligonucleotides except that instead of a scintillation counter, a fluorescence microscope is used to detect the fluorescence. Comparison of the fluorescence observed in samples from normal and diseased cells enables detection of mRNA overexpression.

Procedure 8
Detection of Abnormal mRNA Expression

Tissue or cell samples suspected of expressing abnormal mRNA are incubated with a first $^{32}$P or fluorescein-labeled oligonucleotide which is targeted to the wild-type (normal) mRNA. An identical sample of cells or tissues is incubated with a second labeled oligonucleotide which is targeted to the abnormal mRNA, under conditions in which specific hybridization can occur, and the sample is washed to remove unbound oligonucleotide. Label remaining in the sample indicates bound oligonucleotide and can be quantitated using a scintillation counter, fluorimeter, or other routine means. The presence of abnormal mRNA is indicated if binding is observed in the case of the second but not the first sample.

Double labeling can also be used with the oligonucleotides and methods of the invention to specifically detect expression of abnormal mRNA. A single tissue sample is incubated with a first $^{32}$P-labeled oligonucleotide which is targeted to wild-type mRNA, and a second fluorescein-labeled oligonucleotide which is targeted to the abnormal mRNA, under conditions in which specific hybridization can occur. The sample is washed to remove unbound oligonucleotide and the labels are detected by scintillation counting and fluorimetry. The presence of abnormal mRNA is indicated if the sample does not bind the $^{32}$P-labeled oligonucleotide (i.e., is not radioactive) but does retain the fluorescent label (i.e., is fluorescent).

Procedure 9
Binding Affinity of DMAOE Vs. 2'-deoxyphosphorothioate

The binding affinities of oligonucleotides having either 4 or 10 DMAOE modifications (SEQ ID NO's: 15 and 2) versus each of 3 complementary sequences was determined. The complementary sequences were a) MOE phosphodiesters with each MOE oligonucleotide substituted at the same positions as the DMAOE oligonucleotides; b) a uniform 2'-deoxy phosphodiester; and c) a uniform 2'-deoxyphosphorothioate. The DMAOE modified oligonucleotides show nearly 2.5° C. increase in Tm for each modification compared to the uniform 2'-deoxy phosphorothioate. Compared to the unmodified uniform 2'-deoxy phosphodiester the DMAOE oligonucleotides showed about a 1.6° C. increase in Tm. This will translate into 2.5° C./modification compared to the P=S uniform 2'-deoxyphosphorothioate DNA. More importantly, this increase is even higher than the 2'-MOE by 0.4° C./modification, which is surprising in view of the larger size of DMAOE compared to MOE oligonucleotides.

TABLE 7

Binding Affinity Advantage of 2'-DMAOE over 2'-MOE
(P = O), 2'-deoxyphosphodiester and 2'-deoxyphosphorothioate

| SEQ ID NO: | Tm vs. MOE, ° C. | Tm vs. 2'-H (P = O), ° C. | Tm vs. 2'-H (P = S), ° C. | number of mods |
|---|---|---|---|---|
| 15 | 0.4 | 1.6 | 2.4 | 4 |
| 2 | 0.4 | 1.7 | 2.5 | 10 |

Procedure 10
Procedure A
ICAM-1 Expression

Oligonucleotide Treatment of HUVECs. Cells were washed three times with Opti-MEM (Life Technologies, Inc.) prewarmed to 37° C. Oligonucleotides were premixed with 10 μg/ML Lipofectin (Life Technologies, Inc.) in Opti-MEM, serially diluted to the desired concentrations, and applied to washed cells. Basal and untreated (no oligonucleotide) control cells were also treated with Lipofectin. Cells were incubated for 4 h at 37° C., at which time the medium was removed and replaced with standard growth medium with or without 5 mg/ML TNF-a (R&D Systems). Incubation at 37° C. was continued until the indicated times.

Quantitation of ICAM-1 Protein Expression by Fluorescence-activated Cell Sorter. Cells were removed from plate surface by brief trypsinization with 0.25% trypsin in PBS. Trypsin activity was quenched with a solution of 2% bovine serum albumin and 0.2% sodium azide in PBS (+Mg/Ca). Cells were pelleted by centrifugation (1000 rpm, Beckman GPR centrifuge), resuspended in PBS, and stained with 3 μL/10$^5$ cells of the ICAM-1 specific antibody, CD54-PE (Pharmingin). Antibodies were incubated with the cells for 30 min at 4° C. in the dark, under gentle agitation. Cells were washed by centrifugation procedures and then resuspended in 0.3 ML of FacsFlow buffer (Becton Dickinson) with 0.5% formaldehyde (Polysciences). Expression of cell surface ICAM-1 was then determined by flow cytometry using a Becton Dickinson FACScan. Percentage of the control ICAM-1 expression was calculated as follows: [(oligonucleotide-treated ICAM-1 value)-(basal ICAM-1 value)/(non-treated ICAM-1 value)-(basal ICAM-1 value))]. In one study, 2'-O-(2-methoxy)ethyl-modified anti-intercellular adhesion molecule 1 (ICAM-1) oligonucleotides were shown to selectively increase the ICAM-1 mRNA level and inhibit formation of the ICAM-1 translation initiation complex in human umbilical vein endothelial cells (Baker, et al., *The Journal of Biological Chemistry,* 1997, 272, 11994–12000).

ICAM-1 expression data reveal that the DMAOE oligomers SEQ ID NO: 21 (uniform DMAOE, P=S) and SEQ ID NO: 18 (uniform DMAOE, P=O) are efficacious in HUVEC cells in controlling ICAM-1 expression. The oligomers are presumably working by a direct binding RNase H independent mechanism. The MOE oligomers having SEQ ID NO: 21 (P=S) and SEQ ID NO: 21 (P=O) stand as controls. They have the same sequence composition as SEQ ID NO: 21 and SEQ ID NO: 18.

Both compounds SEQ ID NO: 21 and SEQ ID NO: 18 display dose response in inhibiting ICAM-1 expression between 3 and 100 nM range.

Procedure B

PKC-a mRNA Expression in A549 Cells

This assay was carried out according to a reported procedure (Dean, N. et al., *Journal of Biology and Chemistry*, 269, 16416–16424, 1994). Human A549 lung carcinoma cells were obtained from the American Type Tissue Collection. These were grown in Dulbecco's modified Eagle's medium containing 1 g of glucose/liter (DMEM) and 10% FCS and routinely passaged when 90–95% confluent.

Assay for Oligonucleotide Inhibition of PKC-a Protein Synthesis. A549 cells were plated in 6-well plates (Falcon Labware, Lincoln Park, N.J.) and 24–48 h later (when 80–90% confluent) treated with 1 µM phorbol 12,13-dibutyrate (PDBu) for 18 h. This procedure removes greater than 75% of immunoreactive PKC-a protein from the cells (see "Results"). Cells were then washed three times with 3 ML of DMEM (to remove PDBu), and 1 ML of DMEM containing 20 µg/ML DOTMA/DOPE solution (Lipofectin®) (Bethesda Research Laboratories) was added. Oligonucleotide was then added to the required concentration (for our initial screen, 1 µM) from a 10 µM stock solution, and the two solutions were mixed by swirling of the dish. The cells were incubated at 37° C. for 4 h, washed once with DMEM +10% FCS to remove the DOTMA/DOPE solution, and then an additional 3 ML of DMEM+ 10% FCS was added and the cells were allowed to recover for another 10 h. More prolonged incubation times with DOTMA/DOPE solution resulted in increased cellular toxicity. At this time, cells were washed once in PBS and then extracted in 200 µL of lysis buffer consisting of 20 mM Tris (pH 7.4), 1% Triton X100, 5 mM EGTA, 2 mM dithiothreitol, 50 mM sodium fluoride, 10 mM sodium phosphate, leupeptin (2 µg/ML), and aprotinin (1 µg/ML) (at 4° C.). PKC-a protein levels were determined by immunoblotting with a PKC-a specific monoclonal antibody. Results: DMAOE oligonucleotide gapmers SEQ ID NO: 19 (P=S/P=S/P=S gapmer) and SEQ ID NO: 19 (P=O/P=S/P=O gapmers) inhibit PKC-a mRNA expression in A549 cells in a dose dependent manner between 50–400 nM range. The uniform P=S gapmer is more efficacious than the mixed backbone gapmer. In this experiment the corresponding MOE oligomers were used as the control compounds. The DMAOE oligomers and the MOE oligomers exhibit similar activity in reducing PKC-α mRNA levels.

It is intended that each of the patents, applications, printed publications, and other published documents mentioned or referred to in this specification be herein incorporated by reference in their entirety.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A compound of the structure:

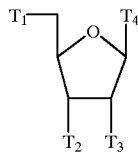

wherein:
- $T_4$ is Bx or Bx—L where Bx is a heterocyclic base moiety;
- one of $T_1$, $T_2$ and $T_3$ is L, hydrogen, hydroxyl, a protected hydroxyl or a sugar substituent group;
- another one of $T_1$, $T_2$ and $T_3$ is L, hydroxyl, a protected hydroxyl, a connection to a solid support or an activated phosphorus-containing substituent group;
- the remaining one of $T_1$, $T_2$ and $T_3$ is L, hydrogen, hydroxyl or a sugar substituent group provided that at least one of $T_1$, $T_2$, or $T_3$ is L or Bx—L;
- said group L having one of the formulas;

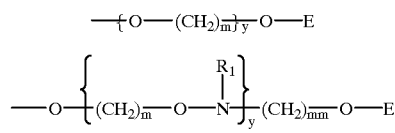

wherein:
- each m and mm is, independently, from 1 to 10;
- y is from 1 to 10;
- E is $N(R_1)(R_2)$ or $N=C(R_1)(R_2)$;
- each $R_1$ and $R_2$ is, independently, H, a nitrogen protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein said substitution is $OR_3$, $SR_3$, $NH_3^+$, $N(R_3)(R_4)$, guanidino or acyl where said acyl is —C(=O)N($R_3$)($R_4$), —C(=O)$R_3$, or —C(=O)O$R_3$;
- provided that when $T_4$ is Bx-L, $R_1$ and $R_2$ are not both H;
- or $R_1$ and $R_2$, together, are a nitrogen protecting group or are joined in a ring structure that optionally includes an additional heteroatom selected from N and O; and
- each $R_3$ and $R_4$ is, independently, H, $C_1$–$C_{10}$ alkyl, a nitrogen protecting group, or $R_3$ and $R_4$, together, are a nitrogen protecting group;
- or $R_3$ and $R_4$ are joined in a ring structure that optionally includes an additional heteroatom selected from N and O.

2. The compound of claim 1 wherein one of $T_1$, $T_2$ or $T_3$ is L.

3. The compound of claim 2 wherein $T_3$ is L.

4. The compound of claim 1 wherein $T_4$ is Bx—L.

5. The compound of claim 1 wherein L is —O—($CH_2$)$_2$—O—N($R_1$)($R_2$).

6. The compound of claim 2 wherein $R_1$ is H or $C_1$–$C_{10}$ alkyl or $C_1$–$C_{10}$ substituted alkyl and $R_2$ is $C_1$–$C_{10}$ substituted alkyl.

7. The compound of claim 6 wherein $R_1$ is $C_1$–$C_{10}$ alkyl.

8. The compound of claim 6 wherein $R_2$ is $NH_3^+$ or $N(R_3)(R_4)$ substituted $C_1$–$C_{10}$ alkyl.

9. The compound of claim 6 wherein $R_1$ and $R_2$ are both $C_1$–$C_{10}$ substituted alkyl.

10. The compound of claim 9 wherein the substituents on the $C_1$–$C_{10}$ substituted alkyls are, independently, $NH_3^+$ or $N(R_3)(R_4)$.

11. The compound of claim 1 wherein Bx is adeninyl, guaninyl, hypoxanthinyl, uracilyl, thyminyl, cytosinyl, 2-aminoadeninyl or 5-methylcytosinyl.

12. The compound of claim 1 wherein $R_1$ and $R_2$ are joined in a ring structure that can include at least one heteroatom selected from N and O.

13. The compound of claim 12 wherein said ring structure is imidazolyl, piperidinyl, morpholino or a substituted piperazinyl.

14. The compound of claim 13 wherein said substituted piperazinyl is substituted with a $C_1$–$C_{12}$ alkyl.

15. The compound of claim 1 wherein $T_1$ is a protected hydroxyl.

16. The compound of claim 1 wherein $T_2$ is an activated phosphorus-containing substituent group or a connection to a solid support.

17. The compound of claim 16 wherein said solid support material is microparticles.

18. The compound of claim 16 wherein said solid support material is controlled pore glass (CPG).

19. The compound of claim 4 wherein L is bound to an exocyclic amino functionality of Bx.

20. The compound of claim 4 wherein L is bound to a cyclic carbon atom of Bx.

21. The compound of claim 4 wherein Bx is adeninyl, 2-aminoadeninyl or guaninyl.

22. The compound of claim 4 wherein Bx is a pyrimidine heterocyclic base and L is covalently bound to said base.

23. The compound of claim 4 wherein Bx is a purine heterocyclic base and L is covalently bound to said base.

24. An oligomeric compound comprising a plurality of nucleoside units of the structure:

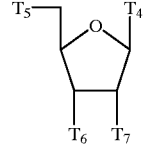

wherein:
- $T_4$ of each nucleoside unit is, independently, Bx or Bx—L where Bx is a heterocyclic base moiety;
- one of $T_5$, $T_6$ and $T_7$ of each nucleoside unit is, independently, L, hydroxyl, a protected hydroxyl, a sugar substituent group, an activated phosphorus-containing substituent group, a connection to a solid support, a nucleoside, a nucleotide, an oligonucleoside or an oligonucleotide;
- another of $T_5$, $T_6$ and $T_7$ of each nucleoside unit is, independently, a nucleoside, a nucleotide, an oligonucleoside or an oligonucleotide;
- the remaining one of $T_5$, $T_6$ and $T_7$ of each nucleoside unit is, independently, is L, hydrogen, hydroxyl, a protected hydroxyl, or a sugar substituent group;
- provided that on at least one of said nucleoside units $T_4$ is Bx—L or at least one of $T_5$, $T_6$ and $T_7$ is L;
- said group L having one of the formulas;

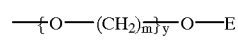

-continued

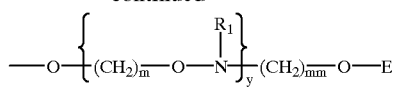

wherein:
each m and mm is, independently, from 1 to 10;
y is from 1 to 10;
E is $N(R_1)(R_2)$ or $N=C(R_1)(R_2)$;
each $R_1$ and $R_2$ is, independently, H, a nitrogen protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein said substitution is $OR_3$, $SR_3$, $NH_3^+$, $N(R_3)(R_4)$, guanidino or acyl where said acyl is —$C(=O)N(R_3)(R_4)$, —$C(=O)R_3$, or —$C(=O)OR_3$,
or $R_1$ and $R_2$, together, are a nitrogen protecting group or are joined in a ring structure that optionally includes an additional heteroatom selected from N and O; and
each $R_3$ and $R_4$ is, independently, H, $C_1$–$C_{10}$ alkyl, a nitrogen protecting group, or $R_3$ and $R_4$, together, are a nitrogen protecting group or wherein $R_3$ and $R_4$ are joined in a ring structure that optionally includes an additional heteroatom selected from N and O.

25. The oligomeric compound of claim 24 having 8 to 30 nucleoside units.

26. The oligomeric compound of claim 24 having 15 to 25 nucleoside units.

27. The oligomeric compound of claim 24 wherein at least one of $T_5$, $T_6$ and $T_7$ is L.

28. The oligomeric compound of claim 24 wherein at least one $T_3$ is L.

29. The oligomeric compound of claim 24 wherein at least one $T_4$ is Bx—L.

30. The oligomeric compound of claim 24 wherein L of one of said nucleoside units is —O—$(CH_2)_2$—O—$N(R_1)(R_2)$.

31. The oligomeric compound of claim 24 wherein $R_1$ is H, $C_1$–$C_{10}$ alkyl or $C_1$–$C_{10}$ substituted alkyl and $R_2$ is $C_1$–$C_{10}$ substituted alkyl.

32. The oligomeric compound of claim 31 wherein $R_1$ is $C_1$–$C_{10}$ alkyl.

33. The oligomeric compound of claim 31 wherein $R_2$ is $NH_3^+$ or $N(R_3)(R_4)$ substituted $C_1$–$C_{10}$ alkyl.

34. The oligomeric compound of claim 31 wherein $R_1$ and $R_2$ are both $C_1$–$C_{10}$ substituted alkyl.

35. The oligomeric compound of claim 34 wherein the substituents on the $C_1$–$C_{10}$ substituted alkyls are, independently, $NH_3^+$ or $N(R_3)(R_4)$.

36. The oligomeric compound of claim 24 wherein Bx is adeninyl, guaninyl, hypoxanthinyl, uracilyl, thyminyl, cytosinyl, 2-aminoadeninyl or 5-methylcytosinyl.

37. The oligomeric compound of claim 24 wherein $R_1$ and $R_2$ are joined in a ring structure that can include at least one heteroatom selected from N and O.

38. The oligomeric compound of claim 37 wherein said ring structure is imidazolyl piperidinyl, morpholino or a substituted piperazinyl.

39. The oligomeric compound of claim 38 wherein said substituted piperazinyl is substituted with a $C_1$–$C_{12}$ alkyl.

40. The oligomeric compound of claim 24 wherein $T_5$ is a protected hydroxyl.

41. The oligomeric compound of claim 24 wherein $T_6$ is an activated phosphorus-containing substituent group or a connection to a solid support.

42. The oligomeric compound of claim 41 wherein said solid support material is microparticles.

43. The oligomeric compound of claim 41 wherein said solid support material is controlled pore glass (CPG).

44. The oligomeric compound of claim 29 wherein L is bound to an exocyclic amino functionality of Bx.

45. The oligomeric compound of claim 29 wherein L is bound to a cyclic carbon atom of Bx.

46. The oligomeric compound of claim 29 wherein Bx is adeninyl, 2-aminoadeninyl or guaninyl.

47. The oligomeric compound of claim 29 wherein Bx is a pyrimidine heterocyclic base and L is covalently bound to said base.

48. The oligomeric compound of claim 29 wherein Bx is a purine heterocyclic base and L is covalently bound to said base.

49. The oligomeric compound of claim 24 having 5 to 50 nucleoside units.

50. An oligomeric compound specifically hybridizable with DNA or RNA comprising a sequence of linked nucleoside units, wherein:
said sequence is divided into a first region having linked nucleoside units and a second region being composed of linked nucleoside units having 2'-deoxy sugar moieties;
said linked nucleoside units of at least one of said first or second regions are connected by phosphorothioate linkages;
at least one of said linked nucleoside units of said first region bearing a group L that is covalently attached to the heterocyclic base or the 2',3' or 5' position of the sugar moiety; said group L having one of the formulas:

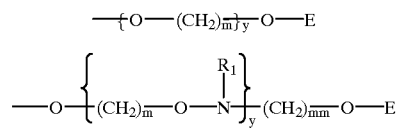

wherein:
each m and mm is, independently, from 1 to 10;
y is from 1 to 10;
E is $N(R_1)(R_2)$ or $N=C(R_1)(R_2)$;
each $R_1$ and $R_2$ is, independently, H, a nitrogen protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein said substitution is $OR_3$, $SR_3$, $NH_3^+$, $N(R_3)(R_4)$, guanidino or acyl where said acyl is —$C(=O)N(R_3)(R_4)$, —$C(=O)R_3$, or —$C(=O)OR_3$;
or $R_1$ and $R_2$, together, are a nitrogen protecting group or are joined in a ring structure that optionally includes an additional heteroatom selected from N and O; and
each $R_3$ and $R_4$ is, independently, H, $C_1$–$C_{10}$ alkyl, a nitrogen protecting group, or $R_3$ and $R_4$, together, are a nitrogen protecting group; and
or $R_3$ and $R_4$ are joined in a ring structure that optionally includes an additional heteroatom selected from N and O.

51. The oligomeric compound of claim 50 wherein Bx is adeninyl, guaninyl, hypoxanthinyl, uracilyl, thyminyl, cytosinyl, 2-aminoadeninyl or 5-methylcytosinyl.

52. The oligomeric compound of claim 50 wherein L is —O—$(CH_2)_2$—O—$N(R_1)(R_2)$.

53. The oligomeric compound of claim 50 wherein at least one of said linked nucleosides of said first region having said group L covalently attached to the 2', 3' or 5'-position of the sugar moiety.

54. The oligomeric compound of claim 53 wherein said group L is covalently attached to the 2'-position of the sugar moiety.

55. The oligomeric compound of claim 50 wherein said nucleoside units of said first and second regions are connected by phosphorothioate internucleoside linkages.

56. The oligomeric compound of claim 50 wherein said nucleoside units of said first region are connected by phosphodiester internucleoside linkages and said nucleoside units of said second region are connected by phosphorothioate internucleoside linkages.

57. The oligomeric compound of claim 50 wherein said nucleoside units of said first region are connected by phosphorothioate internucleoside linkages and said nucleoside units of said second region are connected by phosphodiester internucleoside linkages.

58. The oligomeric compound of claim 50 wherein said second region has at least three nucleoside units.

59. The oligomeric compound of claim 50 wherein said second region has at least five nucleoside units.

60. The oligomeric compound of claim 50 having 5 to 50 nucleoside units.

61. The oligomeric compound of claim 50 having 8 to 30 nucleoside units.

62. The oligomeric compound of claim 50 having 15 to 25 nucleoside units.

63. The oligomeric compound of claim 50 wherein at least one of said linked nucleosides of said first region having said group L covalently attached to the heterocyclic base.

64. The oligomeric compound of claim 63 wherein L is bound to an exocyclic amino functionality of the heterocyclic base.

65. The oligomeric compound of claim 63 wherein L is bound to a cyclic carbon atom of the heterocyclic base.

66. The oligomeric compound of claim 63 wherein the heterocyclic base is adeninyl, 2-aminoadeninyl or guaninyl.

67. The oligomeric compound of claim 63 wherein the heterocyclic base is a pyrimidine and L is covalently bound to said base.

68. The oligomeric compound of claim 63 wherein the heterocyclic base is a purine and L is covalently bound to said base.

69. The oligomeric compound of claim 50 wherein $R_1$ is H, $C_1$–$C_{10}$ alkyl or $C_1$–$C_{10}$ substituted alkyl and $R_2$ is $C_1$–$C_{10}$ substituted alkyl.

70. The oligomeric compound of claim 69 wherein $R_1$ and $R_2$ are both $C_1$–$C_{10}$ substituted alkyl.

71. The oligomeric compound of claim 70 wherein the substituents on the $C_1$–$C_{10}$ substituted alkyls are, independently, $NH_3^+$ or $N(R_3)(R_4)$.

72. The oligomeric compound of claim 69 wherein $R_2$ is $NH_3^+$ or $N(R_3)(R_4)$ substituted $C_1$–$C_{10}$ alkyl.

73. The oligomeric compound of claim 69 wherein $R_1$ is $C_1$–$C_{10}$ alkyl.

74. The oligomeric compound of claim 50 wherein $R_1$ and $R_2$ are joined in a ring structure that can include at least one heteroatom selected from N and O.

75. The oligomeric compound of claim 74 wherein said ring structure is imidazolyl, piperidinyl, morpholino or a substituted piperazinyl.

76. The oligomeric compound of claim 75 wherein said substituted piperazinyl is substituted with a $C_1$–$C_{12}$ alkyl.

77. The oligomeric compound of claim 50 further comprising a third region, said third region having substituted or unsubstituted 2'-O-alkyl nucleoside units, said substituted 2'-O-alkyl nucleoside units bearing a group L, wherein said second region is positioned between said first and third regions.

78. The oligomeric compound of claim 77 wherein said nucleoside units of said first, second and third regions are connected by phosphorothioate linkages.

79. The oligomeric compound of claim 77 wherein said nucleoside units of said first and third regions are connected by phosphodiester linkages and said nucleoside units of said second region are connected by phosphorothioate linkages.

80. The oligomeric compound of claim 77 wherein said nucleoside units of said first and third regions are connected by phosphorothioate linkages and said nucleoside units of said second region are connected by phosphodiester linkages.

81. The oligomeric compound of claim 77 wherein said second region has at least three nucleoside units.

82. The oligomeric compound of claim 77 wherein said second region has at least five nucleoside units.

83. The oligomeric compound of claim 77 wherein at least one of said 2'-O-alkyl nucleoside units of said third region bears a 2'-aminooxy group having one of the formulas:

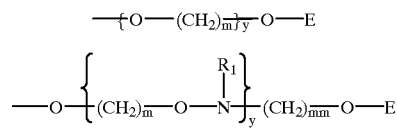

wherein:

each m and mm is, independently, from 1 to 10;

y is from 1 to 10;

E is $N(R_1)(R_2)$ for $N=C(R_1)(R_2)$;

each $R_1$ and $R_2$ is, independently, H, a nitrogen protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein said substitution is $OR_3$, $SR_3$, $NH_3^+$, $N(R_3)(R_4)$, guanidino or acyl where said acyl is $-C(=O)N(R_3)(R_4)$, $-C(=O)R_3$, or $-C(=O)OR_3$;

or $R_1$ and $R_2$, together, are a nitrogen protecting group or are joined in a ring structure that optionally includes an additional heteroatom selected from N and O; and each $R_3$ and $R_4$ is, independently, H, $C_1$–$C_{10}$ alkyl, a nitrogen protecting group, or $R_3$ and $R_4$, together, are a nitrogen protecting group; and or $R_3$ and $R_4$ are joined in a ring structure that optionally includes and additional heteroatom selected from N and O.

* * * * *

SEQUENCE LISTING

```
<160> NUMBER OF SEQ ID NOS: 21

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: antisense
      sequence

<400> SEQUENCE: 1
tttttttttt                                                              10

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: antisense
      sequence

<400> SEQUENCE: 2
tgcatccccc aggccaccat ttttt                                             25

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: antisense
      sequence

<400> SEQUENCE: 3
```

-continued gcgttttttt tttgcg                                                 16

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: antisense
      sequence

<400> SEQUENCE: 4
cgcaaaaaaa aaaaaacgc                                              19

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: antisense
      sequence

<400> SEQUENCE: 5
ctcgtacctt tccggtcc                                               18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: antisense
      sequence

<400> SEQUENCE: 6
ctcgtacttt tccggtcc                                               18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: antisense
      sequence

<400> SEQUENCE: 7
ctcgtaccat tccggtcc                                               18

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: antisense
      sequence

<400> SEQUENCE: 8
ggaccggaag gtacgag                                                17

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: antisense
      sequence

<400> SEQUENCE: 9
accgaggatc atgtcgtacg c                                           21

-continued

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: antisense
      sequence

<400> SEQUENCE: 10
acattatgct agctttttga gtaaacttg                                    29

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: antisense
      sequence

<400> SEQUENCE: 11
gagatctgaa gcttctggat ggtcagcgc                                    29

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: antisense
      sequence

<400> SEQUENCE: 12
gagatctgaa gcttgaagac gccaaaaaca taaag                             35

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: antisense
      sequence

<400> SEQUENCE: 13
acgcatctgg cgcgccgata ccgtcgacct cga                               33

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: antisense
      sequence

<400> SEQUENCE: 14
tttttttttt tttttttt                                                18

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence: antisense
      sequence

<400> SEQUENCE: 15
tccaggtgtc cgcatc                                                  16

```
<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: antisense
      sequence

<400> SEQUENCE: 16
accgaggagg atcatgtcgt acgc                                          24

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: antisense
      sequence

<400> SEQUENCE: 17
accgaggatc atgtcgtacg c                                             21

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 18
tctgagtagc agaggagctc                                               20

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: antisense
      sequence

<400> SEQUENCE: 19
ttctcgctgg tgagtttca                                                19

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 20
ttctcgcccg ctcctcctcc                                               20

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: antisense
      sequence

<400> SEQUENCE: 21
ttgagtagca gaggagctc                                                19
```